US008906682B2

(12) United States Patent
June et al.

(10) Patent No.: US 8,906,682 B2
(45) Date of Patent: *Dec. 9, 2014

(54) METHODS FOR TREATMENT OF CANCER

(71) Applicant: The Trustees of the University of Pennsylvania, Philadelphia, PA (US)

(72) Inventors: Carl H. June, Merion Station, PA (US); Bruce L. Levine, Cherry Hill, NJ (US); David L. Porter, Springfield, PA (US); Michael D. Kalos, Philadelphia, PA (US); Michael C. Milone, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/938,947

(22) Filed: Jul. 10, 2013

(65) Prior Publication Data

US 2013/0309258 A1    Nov. 21, 2013

Related U.S. Application Data

(63) Continuation of application No. 13/992,622, filed as application No. PCT/US2011/064191 on Dec. 9, 2011.

(60) Provisional application No. 61/502,649, filed on Jun. 29, 2011, provisional application No. 61/421,470, filed on Dec. 9, 2010.

(51) Int. Cl.
| | |
|---|---|
| *C12N 5/071* | (2010.01) |
| *C12N 5/0783* | (2010.01) |
| *C12N 5/22* | (2006.01) |
| *A61K 35/14* | (2006.01) |
| *A61K 39/00* | (2006.01) |
| *A61K 39/395* | (2006.01) |

(52) U.S. Cl.
CPC .............. *A61K 35/17* (2013.01); *A61K 39/0011* (2013.01); *A61K 39/39558* (2013.01); *C12N 5/0636* (2013.01); *A61K 2039/5156* (2013.01); *A61K 2039/5158* (2013.01); *C12N 2501/515* (2013.01); *C12N 2510/00* (2013.01)
USPC .......................... 435/372.3; 435/328; 435/330

(58) Field of Classification Search
None
See application file for complete search history.

(56) References Cited

U.S. PATENT DOCUMENTS

| | | | |
|---|---|---|---|
| 5,359,046 A | 10/1994 | Capon et al. | |
| 5,686,281 A | 11/1997 | Roberts | |
| 5,712,149 A | 1/1998 | Roberts | |
| 5,874,240 A | 2/1999 | Ni et al. | |
| 5,906,936 A | 5/1999 | Eshhar et al. | |
| 6,103,521 A | 8/2000 | Capon et al. | |
| 6,319,494 B1 | 11/2001 | Capon et al. | |
| 6,355,779 B1 | 3/2002 | Goodwin et al. | |
| 6,410,319 B1 | 6/2002 | Raubitschek et al. | |
| 6,569,997 B1 | 5/2003 | Kwon | |
| 7,049,136 B2 | 5/2006 | Seed et al. | |
| 7,052,906 B1 | 5/2006 | Lawson et al. | |
| 7,070,995 B2 | 7/2006 | Jensen | |
| 7,265,209 B2 | 9/2007 | Jensen | |
| 7,319,143 B2 | 1/2008 | Gross et al. | |
| 7,320,787 B2 | 1/2008 | Seed et al. | |
| 7,446,190 B2 | 11/2008 | Sadelain et al. | |
| 7,446,191 B2 | 11/2008 | Jensen | |
| 7,514,537 B2 | 4/2009 | Jensen | |
| 7,741,465 B1 | 6/2010 | Eshhar et al. | |
| 7,994,298 B2 | 8/2011 | Zhang et al. | |
| 8,211,422 B2 | 7/2012 | Eshhar et al. | |
| 8,252,914 B2 | 8/2012 | Zhang et al. | |
| 8,389,282 B2 | 3/2013 | Sadelain et al. | |
| 8,399,645 B2 | 3/2013 | Campana et al. | |
| 8,465,743 B2 * | 6/2013 | Rosenberg et al. | ........ 424/134.1 |
| 2003/0060444 A1 | 3/2003 | Finney et al. | |
| 2003/0077249 A1 | 4/2003 | Bebbington et al. | |
| 2003/0148982 A1 | 8/2003 | Brenner et al. | |
| 2004/0038886 A1 | 2/2004 | Finney et al. | |
| 2004/0043401 A1 | 3/2004 | Sadelain et al. | |
| 2005/0113564 A1 | 5/2005 | Campana et al. | |
| 2005/0129671 A1 | 6/2005 | Cooper et al. | |
| 2008/0131415 A1 | 6/2008 | Riddell et al. | |
| 2009/0257994 A1 | 10/2009 | Jensen | |
| 2011/0052554 A1 | 3/2011 | Zakrzewski et al. | |
| 2012/0148552 A1 | 6/2012 | Jensen | |
| 2013/0071414 A1 | 3/2013 | Dotti et al. | |
| 2013/0149337 A1 | 6/2013 | Cooper et al. | |

FOREIGN PATENT DOCUMENTS

| | | |
|---|---|---|
| EP | 0574512 B1 | 2/2003 |
| EP | 1226244 | 7/2004 |
| EP | 871495 | 6/2005 |
| WO | WO92/15322 | 9/1992 |

(Continued)

OTHER PUBLICATIONS

Brentjens, R. et al., "A Phase I Clinical Trial for the Treatment of Chemo-Refractory Chronic Lymphocytic Leukemia with CD19-Targeted Autologous T cells", Mol. Therapy, May 2008, vol. S; pp. 15.*

(Continued)

*Primary Examiner* — Michael Burkhart
(74) *Attorney, Agent, or Firm* — Saul Ewing, LLP; Kathryn Doyle

(57) ABSTRACT

The present invention provides compositions and methods for treating cancer in a human. The invention includes relates to administering a genetically modified T cell to express a CAR wherein the CAR comprises an antigen binding domain, a transmembrane domain, a costimulatory signaling region, and a CD3 zeta signaling domain.

30 Claims, 26 Drawing Sheets

(56) References Cited

FOREIGN PATENT DOCUMENTS

| WO | WO/95/30014 | 11/1995 |
|----|----|----|
| WO | WO96/23814 | 8/1996 |
| WO | WO96/24671 | 8/1996 |
| WO | WO97/15669 | 5/1997 |
| WO | WO/97/23613 | 7/1997 |
| WO | WO98/18809 | 5/1998 |
| WO | WO99/00494 | 1/1999 |
| WO | WO99/57268 | 11/1999 |
| WO | WO/00/14257 | 3/2000 |
| WO | WO/02/33101 | 4/2002 |
| WO | WO/02/077029 | 10/2002 |
| WO | WO/02/088334 | 11/2002 |
| WO | WO2005/019429 | 3/2005 |
| WO | WO2006/060878 | 6/2006 |
| WO | WO2008/045437 | 4/2008 |
| WO | WO/2010/025177 | 3/2010 |
| WO | WO/2010/085660 | 7/2010 |
| WO | WO2011/059836 | 5/2011 |
| WO | WO2012/033885 | 3/2012 |
| WO | WO2012/058460 | 5/2012 |
| WO | WO2012/082841 | 6/2012 |
| WO | WO2012/127464 | 9/2012 |
| WO | WO2012/135854 | 10/2012 |
| WO | WO2012138858 | 10/2012 |
| WO | WO2013/033626 | 3/2013 |
| WO | WO2013/040371 | 3/2013 |
| WO | WO 2013059593 A1 * | 4/2013 |

OTHER PUBLICATIONS

Hollyman, C. et al., "Manufacturing validation of biologically functional T cells targeted to CD19 antigen for autologous adoptive cell theerapy", J. Immunother., Feb. 2010, vol. 32: pp. 169-180.*

Baeksgaard et al., "Acute tumor lysis syndrome in solid tumors—a case report and review of the literature." 2003, Cancer Chemother Pharmacol., 51:187-92.

Bondanza et al., "Suicide gene therapy of graft-versus-host disease induced by central memory human T lymphocytes." 2006, Blood 107:1828-1836.

Brentjens et al., "Genetically targeted T cells eradicate systemic acute lymphoblastic leukemia xenografts." 2007, Clin Cancer Res 13:5426-5435.

Brentjens et al., "Treatment of chronic lymphocytic leukemia with genetically targeted autologous T cells: case report of an unforeseen adverse event in a phase I clinical trial." 2010, Mol Ther, 18: 666-8.

Brentjens et al., "Eradication of systemic B-cell tumors by genetically targeted human T lymphocytes co-stimulated by CD80 and interleukin-15." 2003, Nature Medicine, 9(3): 279-286.

Brocker and Karjalainen, "Signals through T cell receptor-ζchain alone are insufficient to prime resting T lymphocytes." 1995, J. Exp. Med., 181:1653-1659.

Call, et al., "The T cell receptor: critical role of the membrane environment in receptor assembly and function." 2005, Annu Rev Immunol. 2005, 23:101-125.

Campana et al., "T-Cell Immunotherapy for B-Lineage Acute Lymphoblastic Leukemia Using Chimeric Antigen Receptors That Deliver 4-1BB-Mediated Costimulatory Signals" 2003 Blood 102(11); abstract #223.

Carpenito et al., "Control of large, established tumor xenografts with genetically retargeted human T cells containing CD28 and CD137 domains." 2009, Proc Natl Acad Sci U S A 106:3360-3365.

Dohner et al., "p53 gene deletion predicts for poor survival and non-response to therapy with purine analogs in chronic B-cell leukemias." 1995, Blood, 85: 1580-9.

Dropulic et al., "Gene-based immunotherapy for human immunodeficiency virus infection and acquired immunodeficiency syndrome." 2006, Human Gene Therapy, 17: 577-88.

Dull et al., "A third-generation lentivirus vector with a conditional packaging system." 1998, J Virol, 72: 8463-71.

Eshhar et al., "Specific activation and targeting of cytotoxic lymphocytes through chimeric single chains consisting of antibody-binding domains and the γ or ζ subunits of immunoglobulin and T-Cell receptors." 1993, Proc Natl Acad Sci USA 90:720-724.

Finney et al., "Chimeric receptors providing both primary and costimulatory signaling in T cells from a single gene product." 1998, J Immunol 161:2791-2797.

Geiger and Jyothi, "Development and application of receptor-modified T lymphocytes for adoptive immunotherapy." 2001, Transfusion Medicine Reviews, 15(1): 21-34.

Gilham et al., "Primary Polyclonal Human T lymphocytes targeted to carcino-embryonic antigens and neural cell adhesion molecule tumor antigens by CD3ζ-based chimeric immune receptors." 2001, J. Immunology, 25(2): 139-151.

Gong et al., "Cancer patient T cells genetically targeted to prostate-specific membrane antigen specifically lyse prostate cancer cells and release cytokines in response to prostate=specific membrane antigen." 1999, Neoplasia, 1(2): 123-127.

Gribben et al., "Stem cell transplantation for indolent lymphoma and chronic lymphocytic leukemia." 2011, Biol Blood Marrow Transplant, 17: Suppl:S63-S70.

Griffin et al., "Development and application of surface-linked single chain antibodies against T-cell antigens." 2001, J. Immunological Methods, 248: 77-90.

Gross and Eshhar, 1992, "Endowing T cells with antibody specificity using chimeric T cell receptors." 1992, FASEB J. 6: 3370-3378.

Hallek et al., "Guidelines for the diagnosis and treatment of chronic lymphocytic leukemia: a report from the InternationalWorkshop on Chronic Lymphocytic Leukemia updating the National Cancer Institute—Working Group 1996 guidelines." 2008, Blood 111(12):5446-5456.

Hekele et al., "Growth retardation of tumors by adoptive transfer of cytotoxic T lymphocytes reprogrammed by CD44v6-specific scFv:zeta-chimera." 1996, Int J Cancer 68:232-238.

Ho et al., "Adoptive Immunotherapy: Engineering T cell responses as biological weapons for tumor mass destruction." 2003, Cancer Cell 3:431-437.

Imai et al., "Chimeric receptors with 4-1BB signaling capacity provoke potent cytotoxicity against acute lymphoblastic leukemia." 2004, Leukemia 18(4):676-684.

Imai et al., 2005, Genetic modification of primary natural killer cells overcomes inhibitory signals and induces specific killing of leukemic cells, Blood, 106:376-383.

Jena et al., "Redirecting T-cell specificity by introducing a tumor-specific chimeric antigen receptor." 2010, Blood, 116: 1035-44.

Johnson et al., "Gene therapy with human and mouse T-cell receptors mediates cancer regression and targets normal tissues expressing cognate antigen." 2009, Blood, 114: 535-46.

June et al., "Engineering lymphocyte subsets: tools, trials and tribulations." 2009, Nat Rev Immunol, 9: 704-16.

Kershaw et al., "A phase I study on adoptive immunotherapy using gene-modified T cells for ovarian cancer." 2006, Clin Cancer Res 12:6106-6115.

Kim et al., "Human 4-1BB regulates CD28 co-stimulation to promote Th1 cell responses." 1998, Eur J Immunol 28:881-890.

Krause et al., "Antigen-dependent CD28 signaling selectively enhances survival and proliferation in genetically modified activated human primary T lymphocytes." 1998, J. Exp. Med., 188(4): 619-626.

Lamanna et al., "Pentostatin, cyclophosphamide, and rituximab is an active, well-tolerated regimen for patients with previously treated chronic lymphocytic leukemia." 2006, J Clin Oncol, 24: 1575-81.

Lamers et al., "Treatment of metastatic renal cell carcinoma with autologous T-lymphocytes genetically retargeted against carbonic anhydrase IX: first clinical experience." 2006, J Clin Oncol 24:e20-e22.

Laport et al., "Adoptive transfer of costimulated T cells induces lymphocytosis in patients with relapsed/refractory non-Hodgkin lymphoma following CD34+-selected hematopoietic cell transplantation." 2003, Blood 102: 2004-2013.

Lee et al., "In vivo inhibition of human CD19-targeted effector T cells by natural T regulatory cells in a xenotransplant murine model of B cell malignancy." 2011, Cancer Res 71:2871-2881.

(56) References Cited

OTHER PUBLICATIONS

Levine et al., "Gene transfer in humans using a conditionally replicating lentiviral vector." 2006, Proc Natl Acad Sci U S A 103:17372-17377.
Macallan et al., "Measurement and modeling of human T cell kinetics." 2003, Eur J Immunol, 33: 2316-26.
Maher et al., "Human T-lymphocyte cytotoxicity and proliferation directed by a single chimeric TCRzeta /CD28 receptor." 2002, Nat Biotechnol 20(1):70-5.
Milone et al., "Chimeric receptors containing CD137 signal transduction domains mediate enhanced survival of T cells and increased antileukemic efficacy in vivo." 2009, Mol Ther 17(8):1453-64.
Molina, "A decade of rituximab: improving survival outcomes in non-Hodgkin's lymphoma." 2008, Ann Rev Med, 59: 237-50.
Morgan et al., "Case report of a serious adverse event following the administration of T cells transduced with a chimeric antigen receptor recognizing ERBB2." 2010, Mol Ther, 18: 843-51.
Moritz et al., "Cytotoxic T lymphocytes with a grafted recognition specificity for ERBB2-expressing tumor cells" 1994, Proc. Natl. Acad. Sci. 91:4318-4322.
Naldini et al., "In vivo gene delivery and stable transduction of nondividing cells by a lentiviral vector." 1996, Science, 272: 263-7.
Park et al., "Adoptive transfer of chimeric antigen receptor re-directed cytolytic T lymphocyte clones in patients with neuroblastoma." 2007, Mol Ther 15:825-833.
Patel et al., "Impact of chimeric immune receptor extracellular protein domains on T cell function." 1998, Gene Therapy, 6: 412-419.
Porter et al, "A phase 1 trial of donor lymphocyte infusions expanded and activated ex vivo via CD3/CD28 costimulation." 2006, Blood, 107:1325-31.
Pule et al., "Virus-specific T cells engineered to coexpress tumor-specific receptors: persistence and antitumor activity in individuals with neuroblastoma." 2008, Nat Med 14:1264-1270.
Rapoport et al., "Restoration of immunity in lymphopenic individuals with cancer by vaccination and adoptive T-cell transfer." 2005, Nat Med 11:1230-1237.
Roederer, "T-cell dynamics of immunodeficiency." 1995, Nat Med, 1: 621-7.
Sabbagh et al., "TNF family ligands define niches for T cell memory." 2007, Trends Immunol 28:333-339.
Sadelain et al., "The promise and potential pitfalls of chimeric antigen receptors." 2009, Curr Opin Immunol, 21: 215-23.
Sadelain et al., "Targeting tumours with genetically enhanced T lymphocytes." 2003,Nat Rev Cancer 3(1):35-45.
Savoldo et al., "CD28 costimulation improves expansion and persistence of chimeric antigen receptor-modified T cells in lymphoma patients." 2011, J Clin Invest 121(5):1822-6.
Sebestyen, et al., "Human TCR that incorporate CD3zeta induce highly preferred pairing between TCRalpha and beta chains following gene transfer." 2008, J Immunol. 2008, 180(11 ):7736-46.
Sorror et al., "Outcomes after allogeneic hematopoietic cell transplantation with nonmyeloablative or myeloablative conditioning regimens for treatment of lymphoma and chronic lymphocytic leukemia." 2008, Blood, 111: 446-52.
Till et al., "Adoptive immunotherapy for indolent non-Hodgkin lymphoma and mantle cell lymphoma using genetically modified autologous CD20-specific T cells." 2008, Blood, 112, 2261-2271.
Uckun, et al., "Detailed studies on expression and function of CD19 surface determinant by using B43 monoclonal antibody and the clinical potential of anti-CD19 immunotoxins." 1988, Blood, 71:13-29.
Vinay and Kwon, "Role of 4-1BB in immune responses." 1998, Seminars in Immunology, 10:481-489.
Willemsen et al., "Genetic Engineering of T Cell Specificity for Immunotherapy of Cancer." 2003,Human Immunology, 64: 56-68.

Zufferey et al., "Multiply attenuated lentiviral vector achieves efficient gene delivery in vivo." 1997, Nature Biotechnology 15:871-875.
Nicholson, I.C. et al., "Construction and Characterisation of a Functional CD19 Specific Single Chain Fv Fragment for Immunotherapy of B Lineage Leukemia and Lymphoma," Mol. Immunol., 1997, pp. 1157-1165, vol. 34, No. 16-17.
International Search Report for PCT/US2011/064191 dated May 1, 2012.
Till, et al., "Adoptive immunotherapy for indolent non-Hodgkin lymphoma and mantle cell lymphoma using genetically modified autologous CD20-specific T cells." 2008, Blood 112:2261-2271.
U.S. Appl. No. 13/938,923—non-final Office Action dated Sep. 19, 2013.
New Zealand Patent Application No. 612512—First Examination Report dated Nov. 20, 2013.
Finney et al., "Activation of resting human primary T cells with chimeric receptors: costimulation from CD28, inducible costimulator, CD134, and CD137 (4-1BB) in series with signals from the TCR zeta chain." 2004, J. Immunol 172:104-113.
Friedmann-Morvinski et al., "Redirected primary T cells harboring a chimeric receptor require costimulation for their antigen-specific activation." 2005, Blood 105:3087-3093.
Geiger et al., "Integrated src kinase and constimulatory activity enhances signal transduction through single-chain chimeric receptors in T lymphocytes," 2001, Blood 98(8):2364-71.
Hombach et al., "The Recombinant T Cell Receptor Strategy: Insights into Structure and Function of Recombinant Immunoreceptors on the Way Towards an Optimal Receptor Design for Cellular Immunotherapy," 2002 Current Gene Therapy 2:211-226.
Irving & Weiss, "The cytoplasmic domain of the T cell receptor zeta chain is sufficient to couple to receptor-associated signal transduction pathways." 1991, Cell 64:891-901.
Kochenderfer, et al., "Eradication of B-lineage cells and regression of lymphoma in a patient treated with autologous T cells genetically-engineered to recognize CD19." 2010, Blood 116:4099-4102.
Letourneur & Klausner, "T-cell and basophil activation through the cytoplasmic tail of T-cell-receptor zeta family proteins." 1991, Proc Natl Acad Sci U S A 88:8905-8909.
McGuinness, et al., "Anti-tumor activity of human T cells expressing the CC49-zeta chimeric immune receptor." 1999, Hum.Gene Ther 10:165-173.
Moritz & Groner, "A spacer region between the single chain antibody- and the CD3 zeta-chain domain of chimeric T cell receptor components is required for efficient ligand binding and signaling activity," 1995, Gene Therapy, 2:539-546.
Ochoa et al., Immune Defects in T Cells From Cancer Patients, Parallels in Infectious Diseases, from: Cancer Immunotherapy at the Crossroads: how tumors evade immunity and what can be done (current clinical oncology), edited by James H. Finke, Ronald M. Bukowski,, 2004 edition.
Romeo & Seed, "Cellular immunity to HIV activated by CD4 fused to T cell or Fc receptor polypeptides." 1991,Cell 64:1037-1046.
A NCBI Direct Submission NP 000725 dated Nov. 21, 2010.
A NCBI Direct Submission NP 932170.1 dated Nov. 21, 2010.
Colombia Patent Application No. 13-137636—English translation of Office Action of Sep. 5, 2014.
Cuba Patent Application No. 2013/0079 Office Action of Apr. 1, 2014.
Guatemala Patent Application No. A-2013-150—English translation of Observer's comments of Sep. 17, 2014.
Thailand Appl 1301003120—Office Action of Jul. 2014.
U.S. Appl. No. 13/938,923—Final Office Action mailed Mar. 28, 2014.
U.S. Appl. No. 13/938,923—Final Office Action mailed Oct. 8, 2014.
U.S. Appl. No. 14/107,302—non-final Office Action of Sep. 30, 2014.
U.S. Appl. No. 14/466,096—non-final Office Action of Oct. 8, 2014.

* cited by examiner

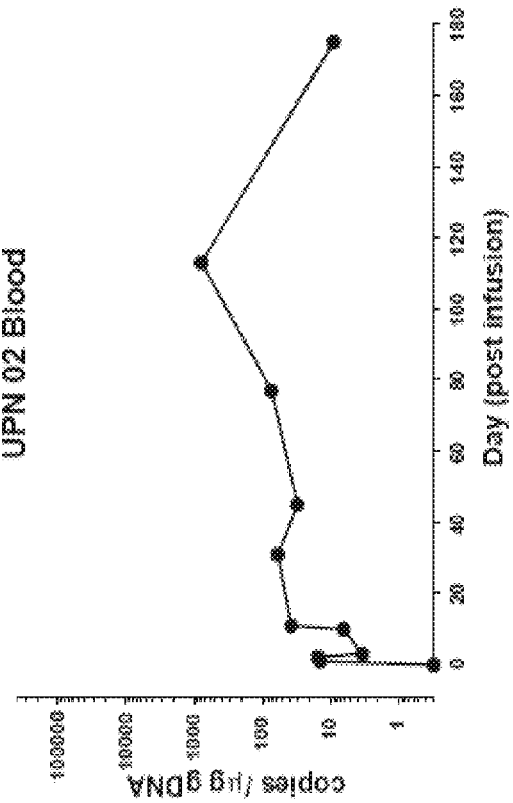
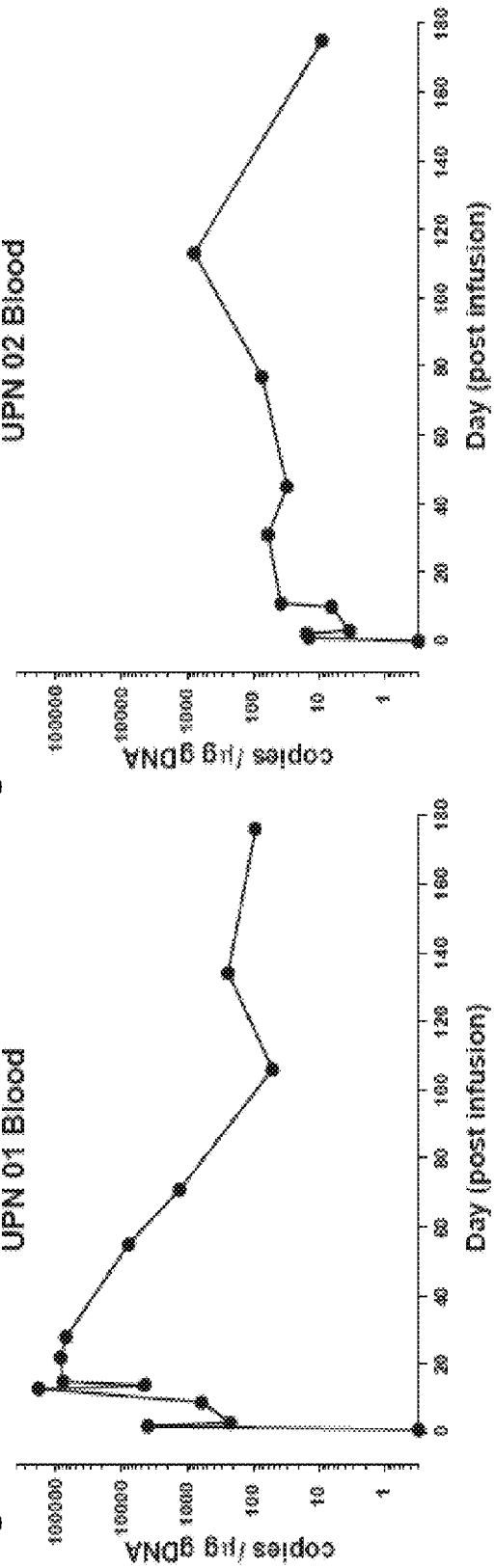
Figure 2B
Figure 2A

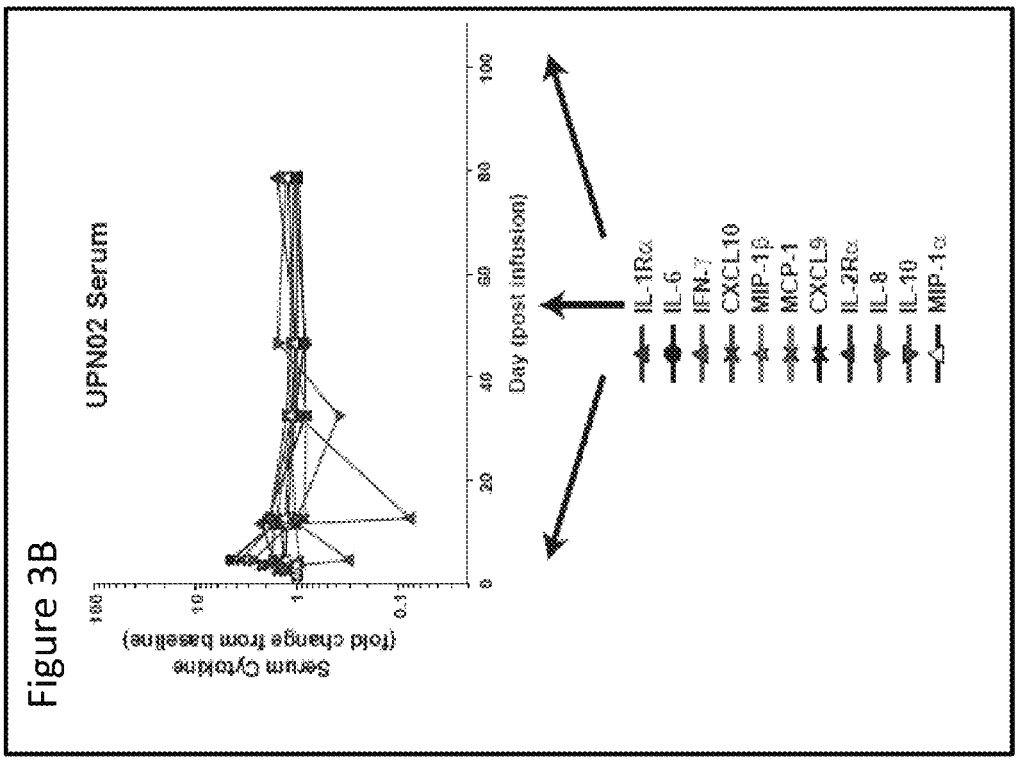
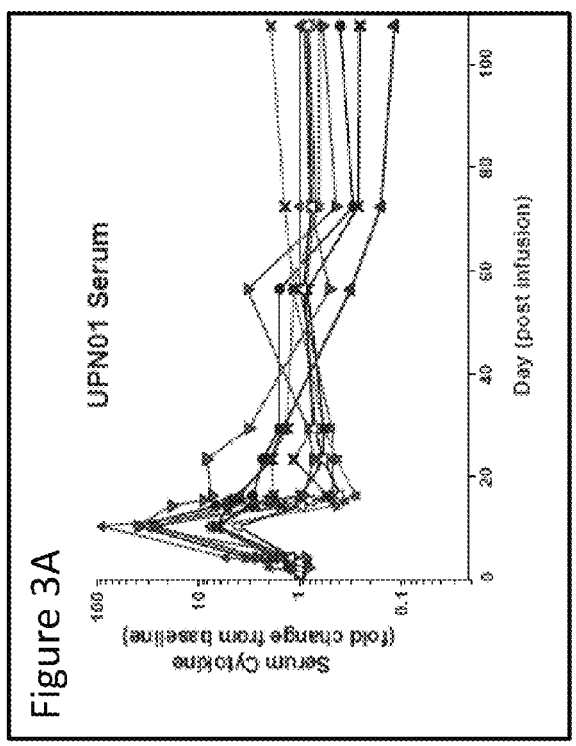
Figure 3A
Figure 3B

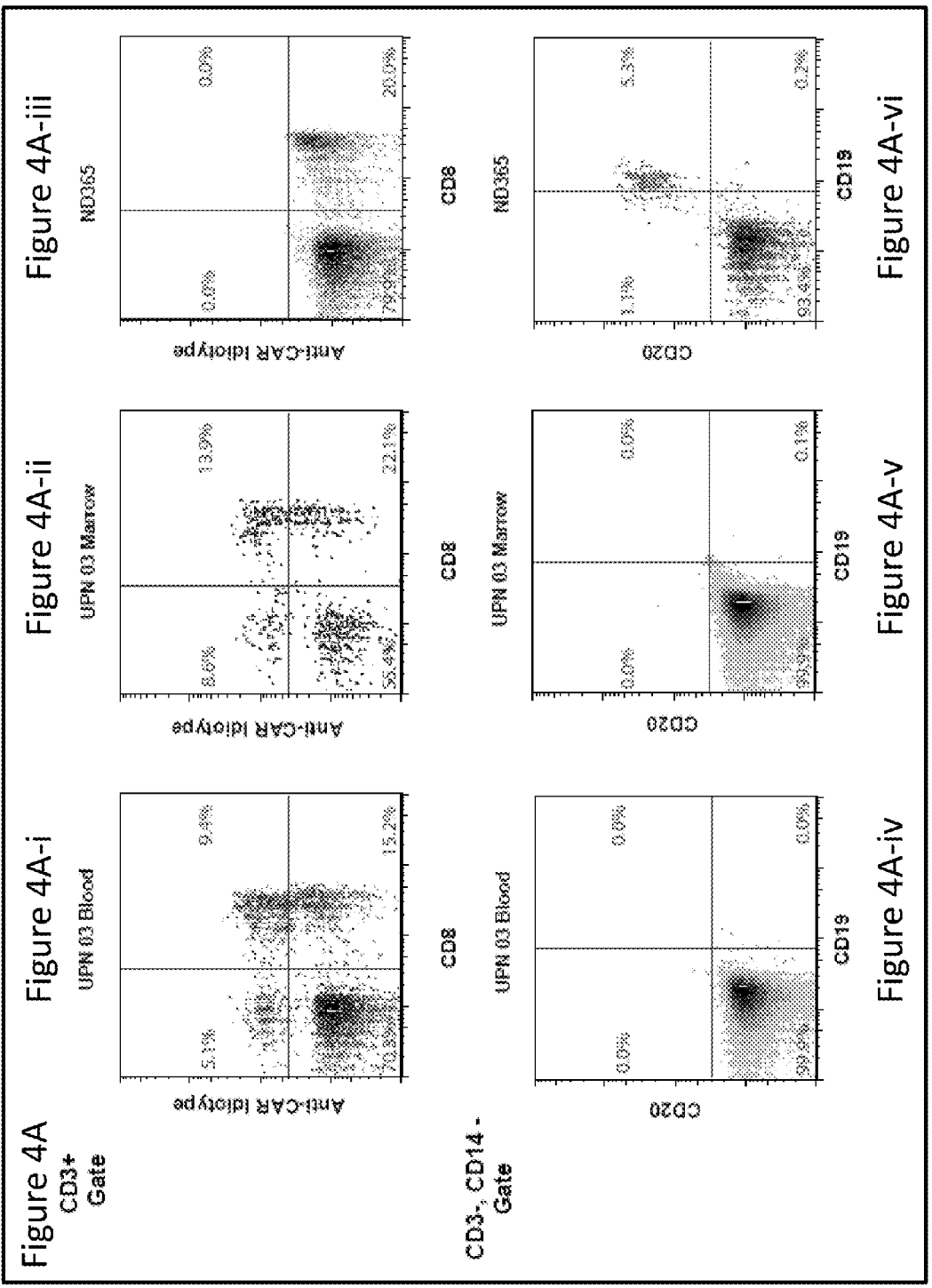

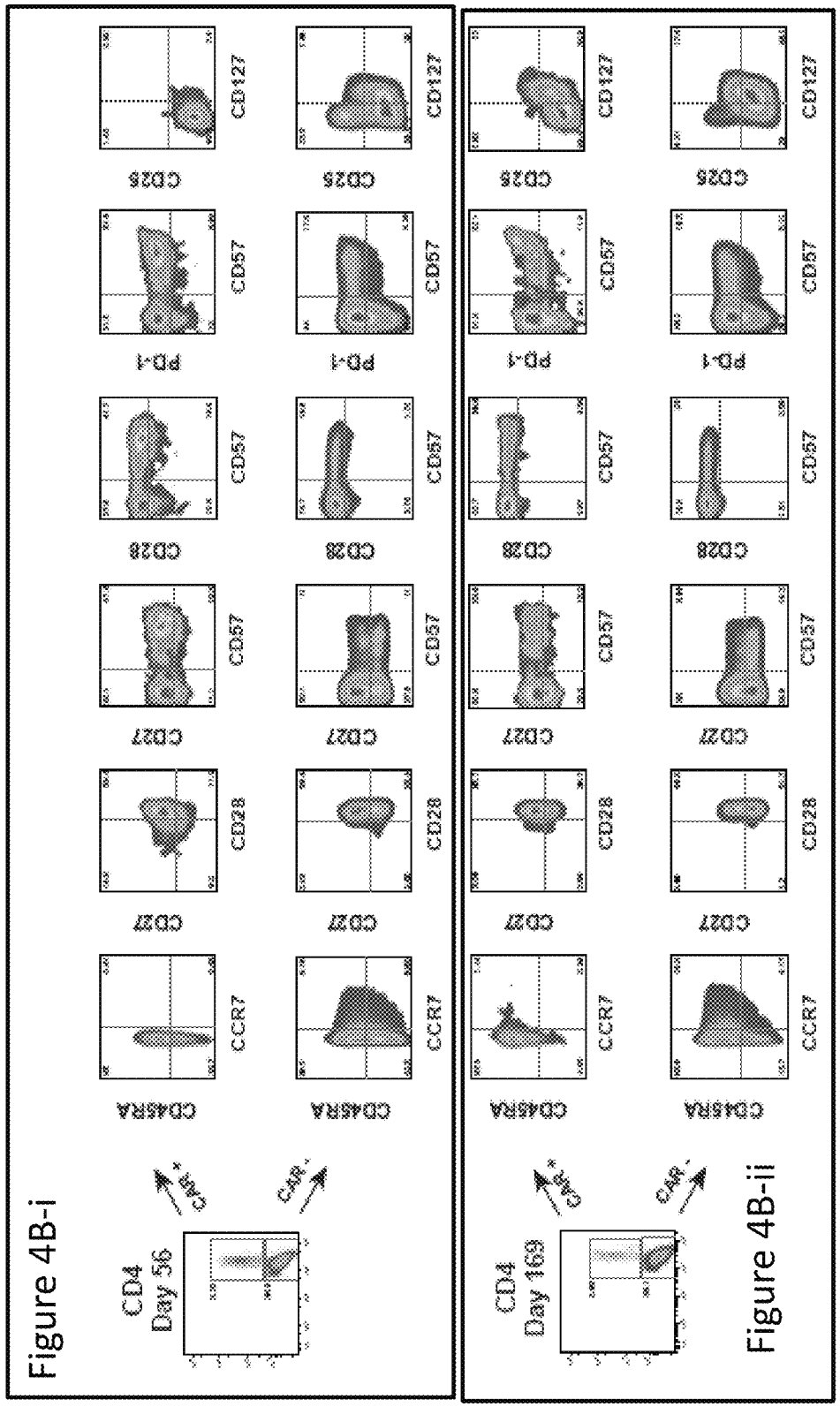
Figure 4B-i
Figure 4B-ii

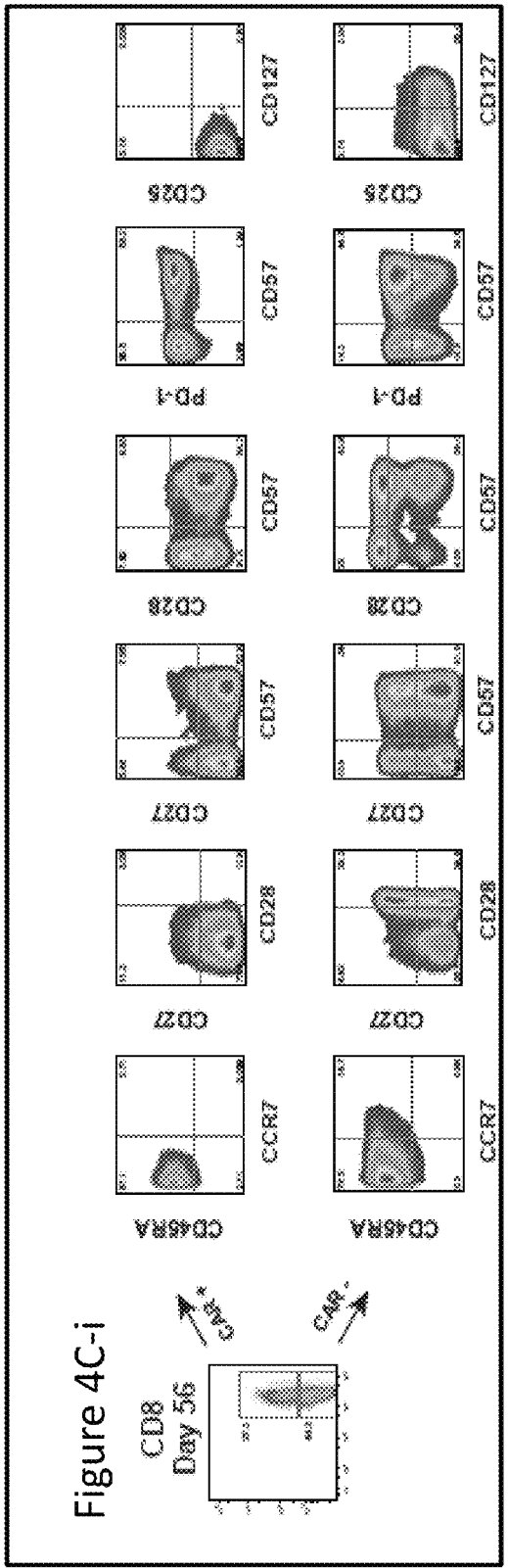
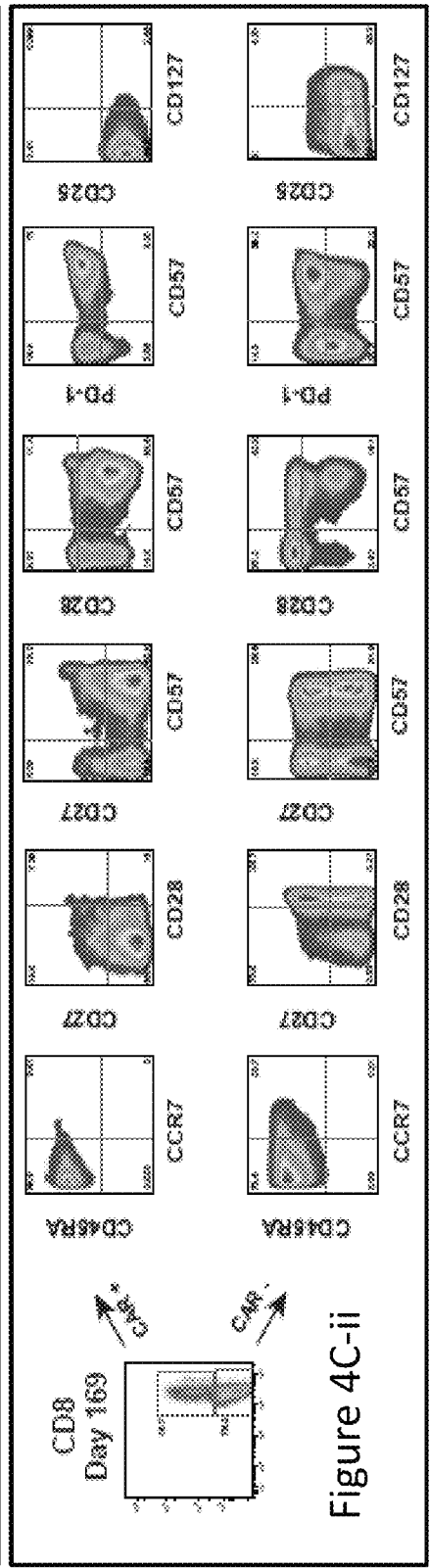
Figure 4C-i
Figure 4C-ii

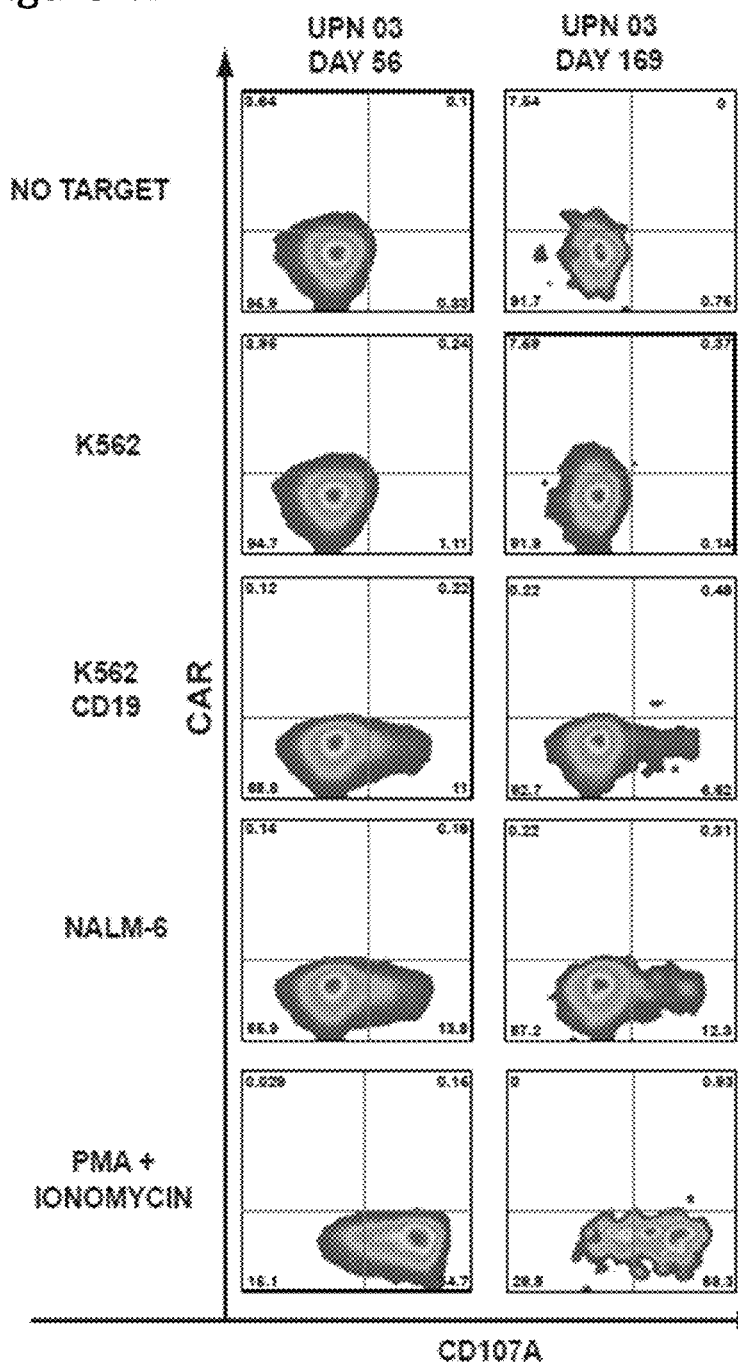

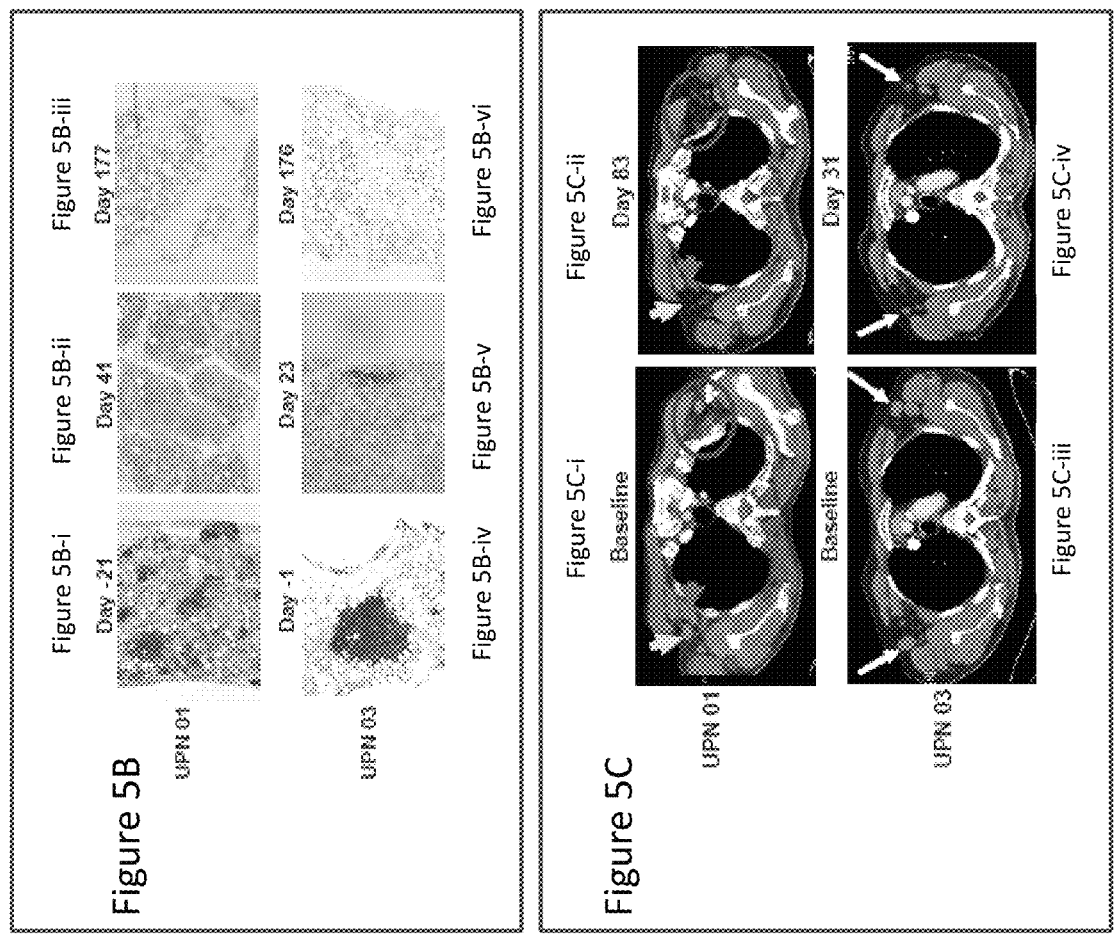

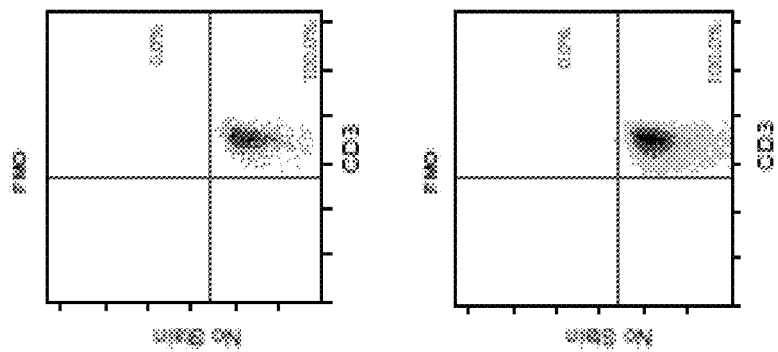
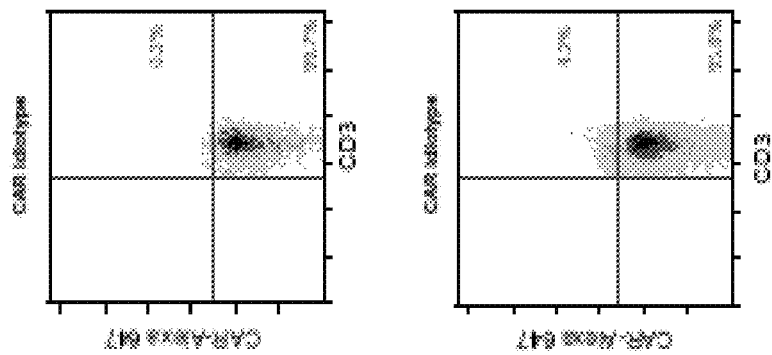
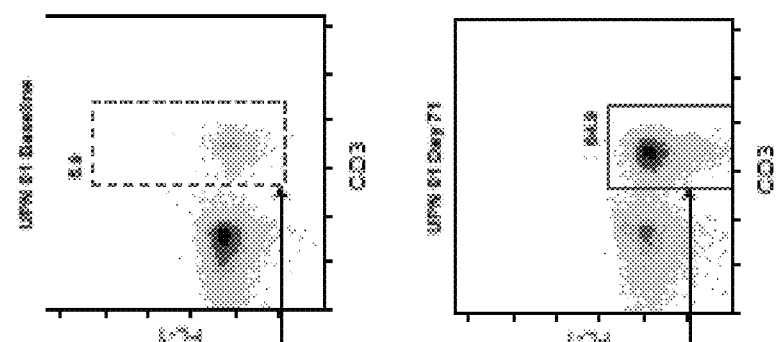
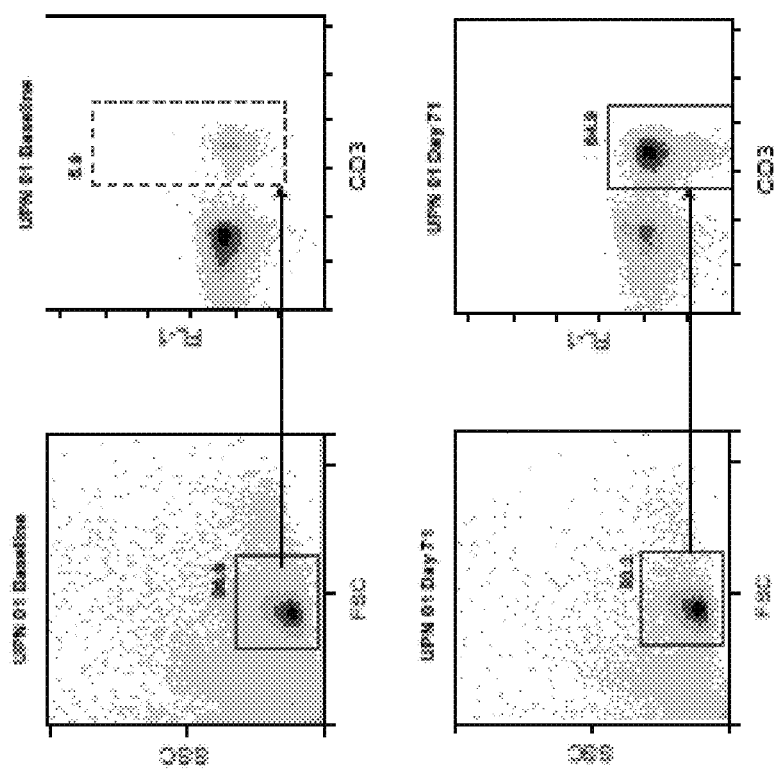

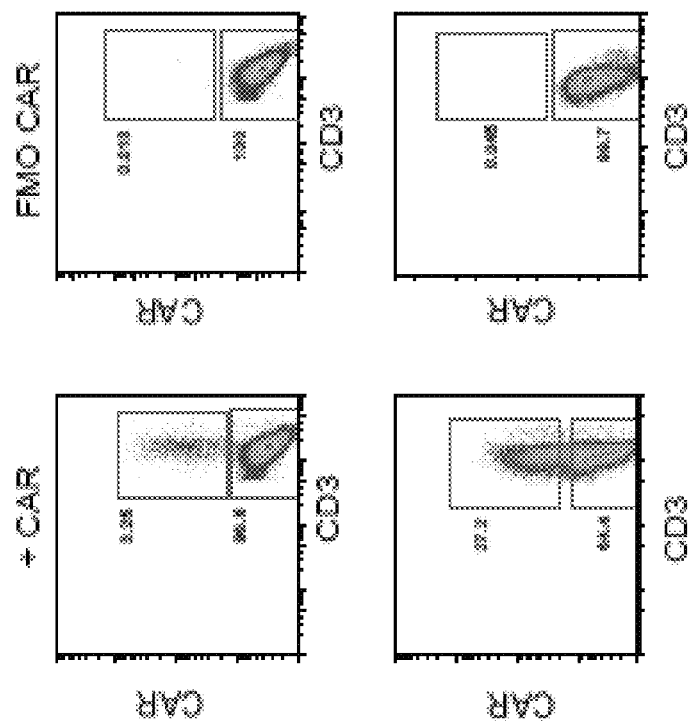
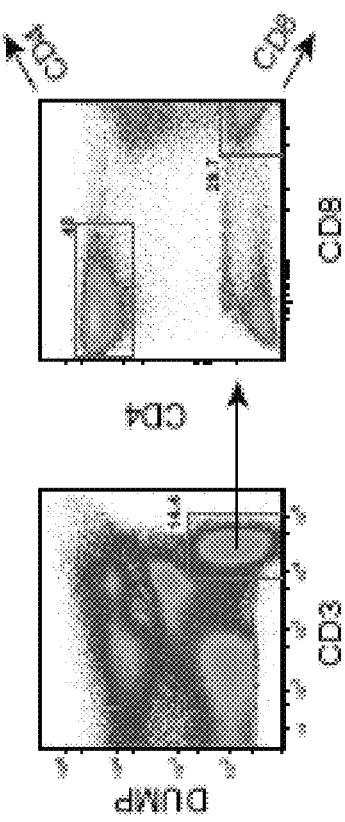
Figure 8A  Figure 8B  Figure 8C

| Subject UPN | Age/sex Karyotype | Previous therapies | CLL Tumor Burden at Baseline | | | Total Dose of CART19 (cells/kg) | Response D +30 (Duration) |
|---|---|---|---|---|---|---|---|
| | | | Bone marrow (Study Day) | Blood (Study Day) | Nodes/spleen (Study Day) | | |
| 01 | 65/M normal | Fludarabine x 4 cycles (2002) Rituximab/Fludarabine x 4 cycles (2006) Alemtuzumab x 12 wks (2008) Rituxan (5 courses 2008-2009) R-CVP x 2 cycles (2009) Lenalidomide (2009) PCR x 2 cycles (6/8L-8/16/2010) Bendamustine x 1 cycle (7/23-8/1/10) pre-CART19 | Hypercellular 70% CLL 2.4x10^9 CLL cells (Day -14) 1.7x10^9 CLL cells (Day -1) | N/A | 8.2x10^9 - 1.0x10^10 CLL cells (Day -37) | 1.1x10^9 (1.5x10^7/kg) | CR (6+ months) |
| 02 | 77/M del(17p13) | Alemtuzumab x 18 wks (6/07) Alemtuzumab x 16 wks (2009) Bendamustine/Rituxan 7/2010 (cycle 1) 7/2010 R2 (cycle 2) 8/2010 (cycle 3) pre-CART19 | Hypercellular >95% CLL 3.2x10^11 CLL cells (Day -4) | 2.7x10^9 CLL Cells Day -1 | 1.9x10^9 - 2.2x10^9 CLL cells (Day -34) | 5.8x10^8 (1.0x10^7/kg) | PR (5 months) |
| 03 | 64/M del(17p13) | R-Fludarabine x 2 cycles (2009) R-Fludarabine x 4 cycles (2009) Alemtuzumab x 3 cycles (3-5/09) Alemtuzumab x 11 wks Rituximab/Cyclophosphamide 6/20/10) pre-CART19 | Hypercellular 40% CLL 6.6x10^10 CLL cells (Day -1) | N/A | 3.3x10^9 - 5.5x10^9 CLL cells (Day -10) | 1.4x10^7 (1.46x10^5/kg) | CR (7+ months) |

1. UPN 02 Karyotype (ISCN Nomenclature): 45,XY,del(1)(q25),+der(1;9)(p13),t(2;20)(p13;q11.3),t(3;5)(p13;q35),add(9)(p23),?del(13)(q14q34),-14,del(17)(p13)[cp24]

2. UPN 03 Karyotype (ISCN Nomenclature): 46,XY,del(17)(p13)[18]/44~46,xx,xx,der(17;18)(17;17)(p11.2;q11.2)[cp4]/46~45,XY,-17[cp3]

3. See Supplementary Materials for methods of tumor burden determination.

Figure 10

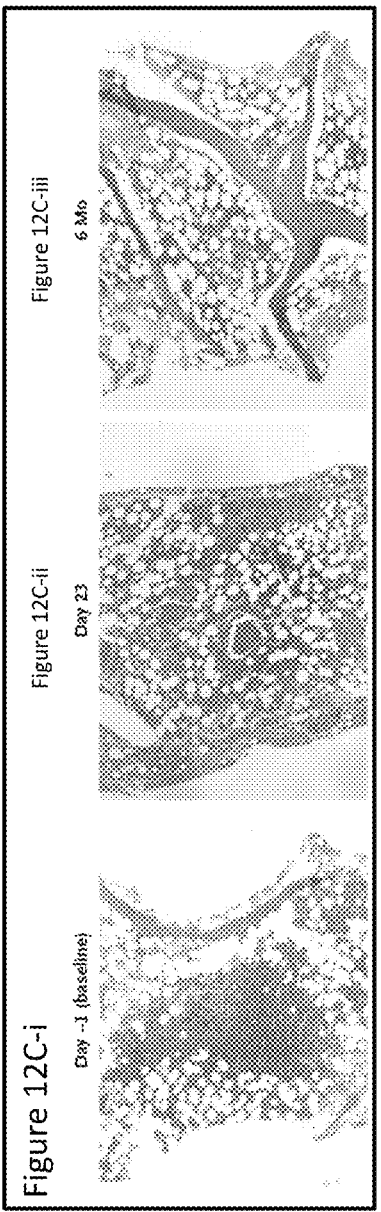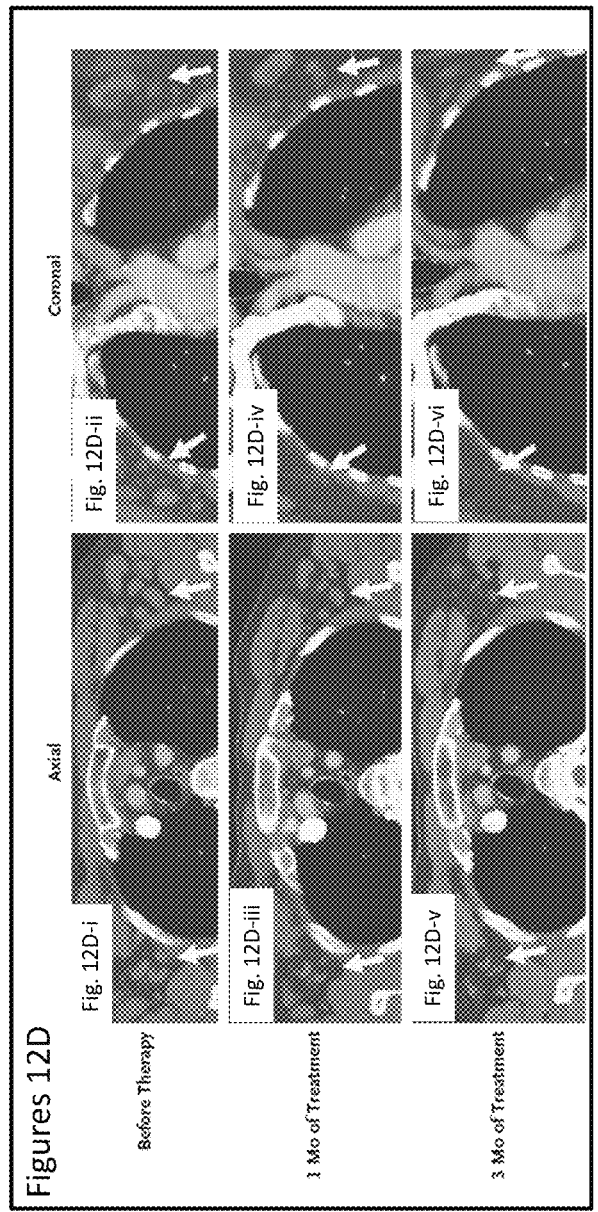

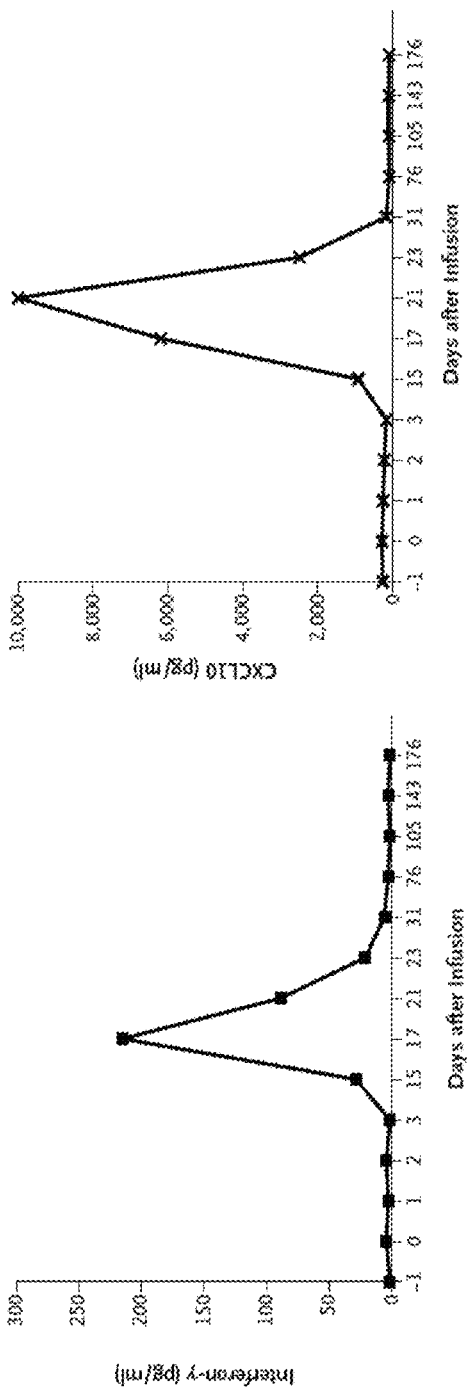
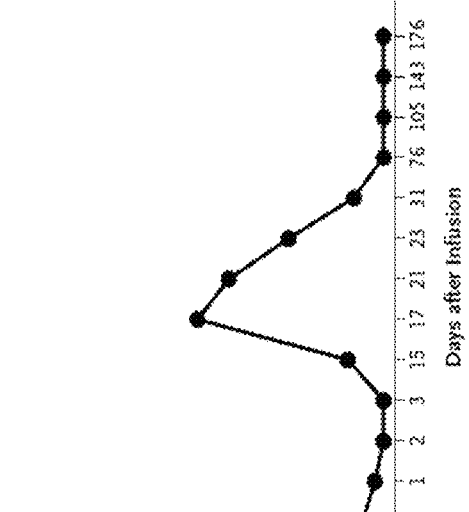
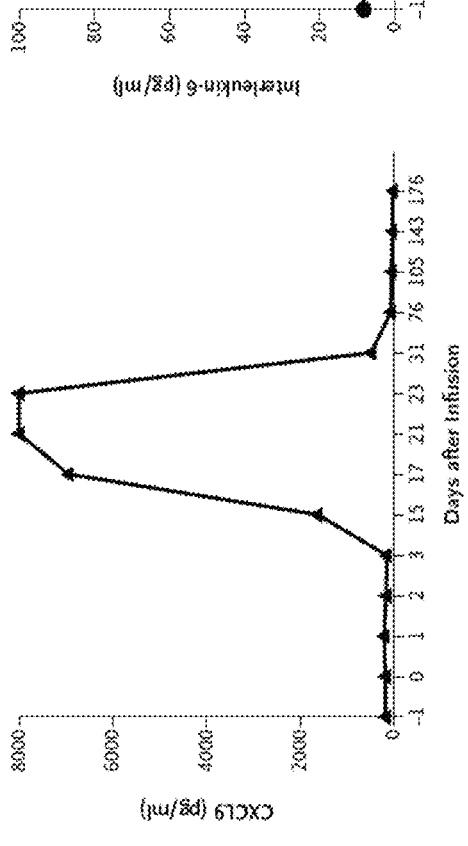
Figures 13A, Figures 13B, Figures 13C, Figures 13D

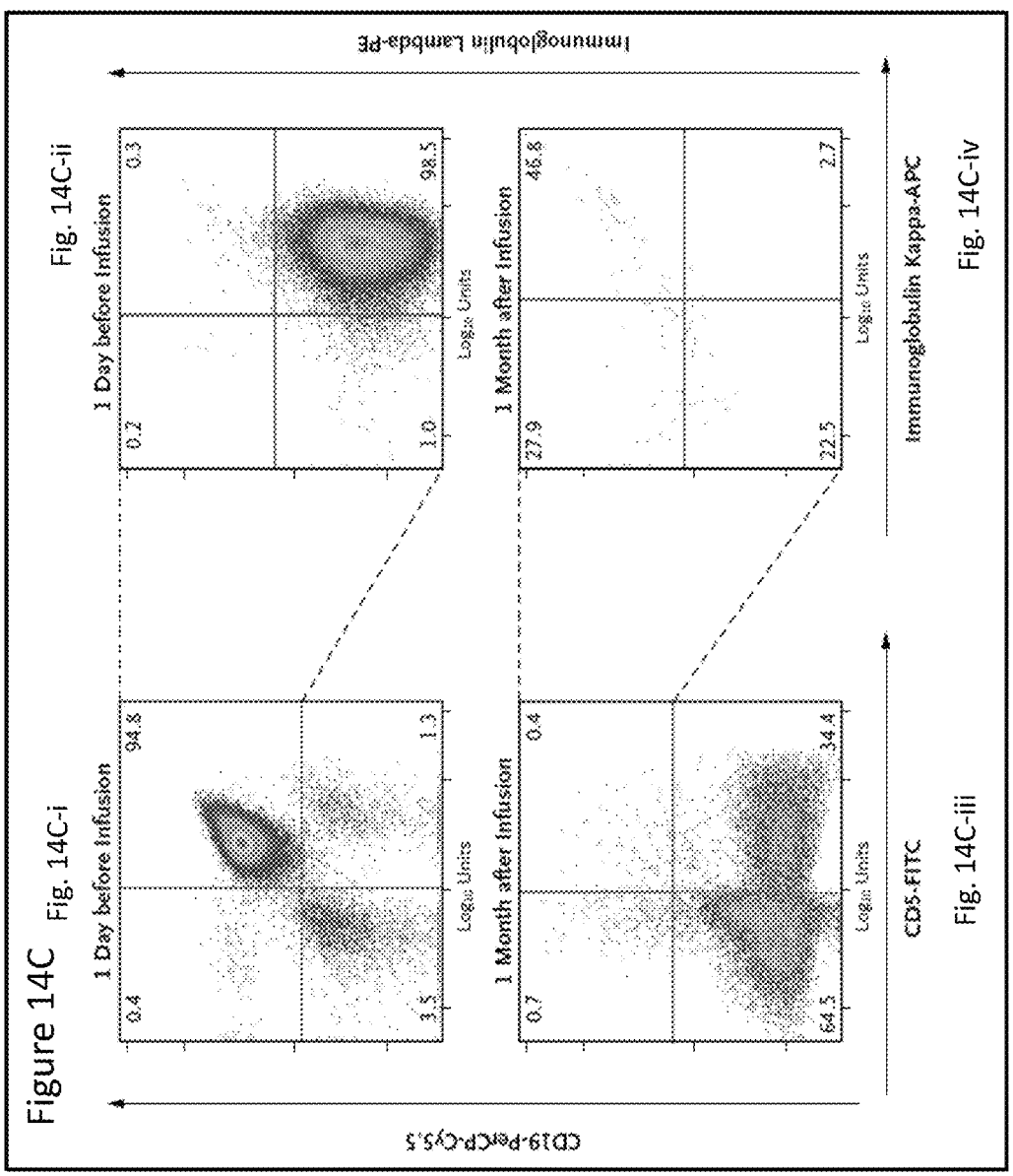

METHODS FOR TREATMENT OF CANCER

CROSS-REFERENCE TO RELATED APPLICATION

This application is a continuation of U.S. patent application Ser. No. 13/992,622, filed Jun. 7, 2013, which is a U.S. national phase application filed under 35 U.S.C. §371 claiming benefit to International Patent Application No. PCT/US2011/064191, filed on Dec. 9, 2011, which is entitled to priority under 35 U.S.C. §119(e) to U.S. Provisional Patent Application No. 61/421,470, filed on Dec. 9, 2010 and U.S. Provisional Patent Application No. 61/502,649, filed on Jun. 29, 2011, each of which application is hereby incorporated herein by reference in its entirety.

STATEMENT REGARDING FEDERALLY SPONSORED RESEARCH OR DEVELOPMENT

This invention was made with government support under grant numbers K24 CA11787901, R01CA120409, 1RO1CA105216, RO1AI057838 and RO11113482 awarded by the National Institutes of Health. The Government therefore has certain rights in the invention.

BACKGROUND OF THE INVENTION

The large majority of patients having B-cell malignancies, including chronic lymphocytic leukemia (CLL), will die from their disease. One approach to treating these patients is to genetically modify T cells to target antigens expressed on tumor cells through the expression of chimeric antigen receptors (CARs). CARs are antigen receptors that are designed to recognize cell surface antigens in a human leukocyte antigen-independent manner. Attempts in using genetically modified cells expressing CARs to treat these types of patients have met with very limited success. See for example, Brentjens et al., 2010, Molecular Therapy, 18:4, 666-668; Morgan et al., 2010, Molecular Therapy, published online Feb. 23, 2010, pages 1-9; and, Till et al., 2008, Blood, 112:2261-2271.

In most cancers, tumor-specific antigens are not yet well defined, but in B cell malignancies, CD19 is an attractive tumor target. Expression of CD19 is restricted to normal and malignant B cells (Uckun, et al. *Blood,* 1988, 71:13-29), so that CD19 is a widely accepted target to safely test CARs. While CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity (Jena, et al., *Blood,* 2010, 116:1035-1044; Uckun, et al. Blood, 1988, 71:13-29).

Thus, there is an urgent need in the art for compositions and methods for treatment of cancer using CARs that can expand in vivo. The present invention addresses this need.

SUMMARY OF THE INVENTION

The present invention provides an isolated nucleic acid sequence encoding a chimeric antigen receptor (CAR), wherein the CAR comprises an antigen binding domain, a transmembrane domain, a costimulatory signaling region, and a CD3 zeta signaling domain, wherein the CD3 zeta signaling domain comprises the amino acid sequence of SEQ ID NO: 24.

In one embodiment, the nucleic acid sequence encodes a CAR comprising the amino acid sequence of SEQ ID NO: 12.

In one embodiment, the nucleic acid sequence encoding a CAR comprises the nucleic acid sequence of SEQ ID NO: 8.

In one embodiment, the antigen binding domain in the CAR is an antibody or an antigen-binding fragment thereof. Preferably, the antigen-binding fragment is a Fab or a scFv.

In one embodiment, the antigen binding domain in the CAR binds to a tumor antigen. In one embodiment, the tumor antigen is associated with a hematologic malignancy. In another embodiment, the tumor antigen is associated with a solid tumor. In yet another embodiment, the tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, and any combination thereof.

In one embodiment, the costimulatory signaling region in the CAR comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In one embodiment, the CD3 zeta signaling domain in the CAR is encoded by the nucleic acid sequence of SEQ ID NO: 18.

The invention also provides an isolated CAR comprising an antigen binding domain, a transmembrane domain, a costimulatory signaling region, and a CD3 zeta signaling domain, wherein the CD3 zeta signaling domain comprises the amino acid sequence of SEQ ID NO: 24.

The invention also provides a cell comprising a nucleic acid sequence encoding a CAR, wherein the CAR comprises an antigen binding domain, a transmembrane domain, a costimulatory signaling region, and a CD3 zeta signaling domain comprising the amino acid sequence of SEQ ID NO: 24.

In one embodiment, the cell comprising the CAR is selected from the group consisting of a T cell, a Natural Killer (NK) cell, a cytotoxic T lymphocyte (CTL), and a regulatory T cell.

In one embodiment, the cell comprising the CAR exhibits an anti-tumor immunity when the antigen binding domain of the CAR binds to its corresponding antigen.

The invention also provides a vector comprising a nucleic acid sequence encoding a CAR, wherein the CAR comprises an antigen binding domain, a costimulatory signaling region, and a CD3 zeta signaling domain, wherein the CD3 zeta signaling domain comprises the amino acid sequence of SEQ ID NO: 24.

The invention also provides a method for stimulating a T cell-mediated immune response to a target cell population or tissue in a mammal. In one embodiment, the method comprises administering to a mammal an effective amount of a cell genetically modified to express a CAR wherein the CAR comprises an antigen binding domain, a costimulatory signaling region, and a CD3 zeta signaling domain comprising the amino acid sequence of SEQ ID NO: 24, wherein the antigen binding domain is selected to specifically recognize the target cell population or tissue.

The invention also provides a method of providing an anti-tumor immunity in a mammal. In one embodiment, the method comprises administering to a mammal an effective amount of a cell genetically modified to express a CAR wherein the CAR comprises an antigen binding domain, a costimulatory signaling region, and a CD3 zeta signaling domain comprising the amino acid sequence of SEQ ID NO: 24, thereby providing an anti-tumor immunity in the mammal.

The invention also includes a method of treating a mammal having a disease, disorder or condition associated with an elevated expression of a tumor antigen. In one embodiment, the method comprises administering to a mammal an effective amount of a cell genetically modified to express a CAR wherein the CAR comprises an antigen binding domain, a costimulatory signaling region, and a CD3 zeta signaling domain comprising the amino acid sequence of SEQ ID NO: 24, thereby treating the mammal.

In one embodiment, the cell is an autologous T cell.

In one embodiment, the tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, and any combination thereof.

The invention also provides a method of treating a human with chronic lymphocytic leukemia. In one embodiment, the method comprises administering to a human a T cell genetically engineered to express a CAR wherein the CAR comprises an antigen binding domain, a costimulatory signaling region, and a CD3 zeta signaling domain comprising the amino acid sequence of SEQ ID NO: 24.

In one embodiment, the human is resistant to at least one chemotherapeutic agent In one embodiment, the chronic lymphocytic leukemia is refractory CD19+ leukemia and lymphoma.

The invention also includes a method of generating a persisting population of genetically engineered T cells in a human diagnosed with cancer. In one embodiment, the method comprises administering to a human a T cell genetically engineered to express a CAR wherein the CAR comprises an antigen binding domain, a costimulatory signaling region, and a CD3 zeta signaling domain comprising the amino acid sequence of SEQ ID NO: 24, wherein the persisting population of genetically engineered T cells persists in the human for at least one month after administration.

In one embodiment, the persisting population of genetically engineered T cells comprises at least one cell selected from the group consisting of a T cell that was administered to the human, a progeny of a T cell that was administered to the human, and a combination thereof.

In one embodiment, the persisting population of genetically engineered T cells comprises a memory T cell.

In one embodiment, the persisting population of genetically engineered T cells persists in the human for at least three months after administration. In another embodiment, the persisting population of genetically engineered T cells persists in the human for at least four months, five months, six months, seven months, eight months, nine months, ten months, eleven months, twelve months, two years, or three years after administration.

In one embodiment, the chronic lymphocytic leukemia is treated.

The invention also provides a method of expanding a population of genetically engineered T cells in a human diagnosed with cancer. In one embodiment, the method comprises administering to a human a T cell genetically engineered to express a CAR wherein the CAR comprises an antigen binding domain, a costimulatory signaling region, and a CD3 zeta signaling domain comprising the amino acid sequence of SEQ ID NO: 24, wherein the administered genetically engineered T cell produces a population of progeny T cells in the human.

In one embodiment, the progeny T cells in the human comprise a memory T cell.

In one embodiment, the T cell is an autologous T cell.

In another embodiment, the human is resistant to at least one chemotherapeutic agent.

In one embodiment, the cancer is chronic lymphocytic leukemia. In another embodiment, the chronic lymphocytic leukemia is refractory CD19+ leukemia and lymphoma.

In one embodiment, the population of progeny T cells persists in the human for at least three months after administration. In another embodiment, the population of progeny T cells persist in the human for at least four months, five months, six months, seven months, eight months, nine months, ten months, eleven months, twelve months, two years, or three years after administration.

In one embodiment, the cancer is treated.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts the lentiviral vectors and transgene that show the major functional elements. A vesicular stomatitis virus protein G pseudotyped clinical grade lentiviral vector (designated pELPs 19BBz) directing expression of anti-CD19 scFv derived from FMC63 murine monoclonal antibody, human CD8α hinge and transmembrane domain, and human 4-1BB and CD3zeta signaling domains was produced. Constitutive expression of the transgene was directed by inclusion of an EF-1α (elongation factor-1α promoter); LTR, long terminal repeat; RRE, rev response element. (cPPT) and the central termination sequence (CTS). Figure is not to scale. FIG. 1B depicts T cell manufacturing. Autologous cells were obtained via an apheresis, and T cells were enriched by mononuclear cell elutriation, washed and residual leukemia cells depleted by addition of anti-CD3/CD28 coated paramagnetic beads for positive selection and activation of T cells. Lentiviral vector was added at the time of cell activation and was washed out on day 3 post culture initiation. Cells were expanded on a rocking platform device (WAVE Bioreactor System) for 8-12 days. On the final day of culture the beads were removed by passage over a magnetic field and the CART19 T cells harvested and cryopreserved in infusible medium. FIG. 1C depicts the clinical protocol design. Patients were given lymphodepleting chemotherapy as described, followed by CART19 infusion #1 by i.v. gravity flow drip over a period of 15-20 minutes. The infusion was given using a split dose approach over 3 days (10%, 30%, 60%) beginning 1 to 5 days after completion of chemotherapy. Endpoint assays were conducted on study week 4. At the conclusion of active monitoring, subjects were transferred to a destination protocol for long term follow up as per FDA guidance.

FIG. 2, comprising FIGS. 2A through 2F, is a series of images demonstrating sustained in vivo expansion and persistence in blood and marrow of CART19 cells. DNA isolated from whole blood as depicted in FIG. 2A through 2C or marrow as depicted in FIG. 2D through 2F, samples obtained from UPN 01 as depicted in FIGS. 2A and 2D, UPN 02 as depicted in FIGS. 2B and 2E and UPN 03 as depicted in FIGS. 2C and 2F was subjected in bulk to Q-PCR analysis using a qualified assay to detect and quantify CART19 sequences. Each data point represents the average of triplicate measurements on 100-200 ng genomic DNA, with maximal % CV less than 1.56%. Pass/fail parameters for the assay included pre-established ranges for slope and efficiency of amplification, and amplification of a reference sample. The lower limit of quantification for the assay established by the standard curve range was 2 copies transgene/microgram genomic DNA; sample values below that number are considered estimates and presented if at least ⅔ replicates generated a Ct value with % CV for the values 15%. CART19 cells were infused at day 0, 1, and 2 for UPN 01 and UPN 03, and days 0, 1, 2 and 11 for UPN 02.

FIG. 3, comprising FIGS. 3A through 3D, is a series of images demonstrating serum and bone marrow cytokines before and after CAR T cell infusion; longitudinal measurements of changes in serum cytokines, chemokines and cytokine receptors in UPN 01 as depicted in FIG. 3A, UPN 02 as depicted in FIG. 3B and UPN 03 as depicted in FIG. 3C, on the indicated day after CART19 cell infusion and serial assessments of the same analytes in the bone marrow from UPN 03 as depicted in FIG. 3D. Samples were subjected multiplex analysis using Luminex bead array technology and pre-assembled and validated multiplex kits. Analytes with a >=3 fold change are indicated, and plotted as relative change from baseline as depicted in FIG. 3A through 3C or as absolute values as depicted in FIG. 3D. Absolute values for each analyte at each time-point were derived from a recombinant protein-based standard curve over a 3-fold 8-point dilution series, with upper and lower limits of quantification (ULOQ, LLOQ) determined by the 80-120% observed/expected cutoff values for the standard curves. Each sample was evaluated in duplicate with average values calculated and % CV in most cases less than 10%. To accommodate consolidated data presentation in the context of the wide range for the absolute values, data are presented as fold-change over the baseline value for each analyte. In cases where baseline values were not detectable, half of the lowest standard curve value was used as the baseline value. Standard curve ranges for analytes and baseline (day 0) values (listed in parentheses sequentially for UPN01, 02 and 03), all in pg/ml: IL1-Rα: 35.5-29,318 (689, 301, 287); IL-6: 2.7-4,572 (7, 10.1, 8.7); IFN-γ: 11.2-23,972 (2.8, ND, 4.2); CXCL10: 2.1-5,319 (481, 115, 287); MIP-1β: 3.3-7,233 (99.7, 371, 174); MCP-1: 4.8-3,600 (403, 560, 828); CXCL9: 48.2-3,700 (1,412, 126, 177); IL2-Ra: 13.4-34,210 (4,319, 9,477, 610); IL-8: 2.4-5,278 (15.3, 14.5, 14.6); IL-10: 6.7-13,874 (8.5, 5.4, 0.7); MIP-1α: 7.1-13,778 (57.6, 57.3, 48.1).

FIG. 4, comprising FIGS. 4A through 4D, is a series of images depicting prolonged surface CART19 expression and establishment of functional memory CARs in vivo. FIG. 4A, comprising FIGS. 4A-i through 4A-vi, depicts detection of CAR-expressing CD3+ lymphocytes and absence of B cells in periphery and marrow. Freshly processed peripheral blood or marrow mononuclear cells obtained from UPN 03 at day 169 post-CART19 cell infusion were evaluated by flow-cytometry for surface expression of CAR19 (top) or presence of B cells (bottom); as a control, PBMC obtained from a healthy donor ND365 were stained. The gating strategy for the CD3+ and B cell populations is presented in FIG. 9. To evaluate CAR19 expression in CD3+ lymphocytes, samples were co-stained with antibodies to CD14-PE-Cy7 and CD16-PE-Cy7 (dump channel) and CD3-FITC, positively gated on CD3+, and evaluated for CAR19 expression in the CD8+ and CD8-lymphocyte compartments by co-staining with CD8a-PE and the anti-CAR19 idiotype antibody conjugated to Alexa-647. Data in plots are gated on the dump channel-negative/CD3-positive cell population. To evaluate the presence of B cells, samples were co-stained with antibodies to CD14-APC and CD3-FITC (dump channels) and evaluated for the presence of B cells in the dump channel-negative fraction by co-staining with antibodies to CD20-PE and CD19-PE-Cy-7. In all cases, negative gate quadrants were established on no-stain controls as depicted in FIGS. 4B (4B-i and 4B-ii) and 4C (4C-i and 4C-ii). T cell immunophenotyping of CD4+ (FIG. 4B) and CD8+ (FIG. 4C) T cell subsets is shown. Frozen peripheral blood samples from UPN 03 obtained by apheresis at day 56 and 169 post T cell infusion were rested overnight in culture medium with no added factors, washed, and subjected to multi-parametric immunophenotyping for expression of markers of T cell memory, activation, and exhaustion. The gating strategy, as depicted in FIG. 8, involved an initial gating on dump channel (CD14, CD16, Live/Dead Aqua)-negative and CD3-positive cells, followed by positive gates on CD4+ and CD8+ cells. Gates and quadrants were established using FMO controls (CAR, CD45RA, PD-1, CD25, CD127, CCR7) or by gating on positive cell populations (CD3, CD4, CD8) and clearly delineated subsets (CD27, CD28, CD57); data were displayed after bi-exponential transformation for objective visualization of events. FIG. 4D depicts functional competence of persisting CAR cells. Frozen peripheral blood samples from UPN 03 obtained by apheresis at day 56 and 169 post T cell infusion were rested overnight in culture medium with no added factors, washed, and evaluated directly ex-vivo for the ability to recognize CD19-expressing target cells using CD107 degranulation assays. Following a two-hour incubation in the presence of anti-CD28, anti-CD49d, and CD107-FITC, cell mixtures were harvested, washed, and subjected to multi-parametric flow cytometric analysis to evaluate the ability of CART19 cells to de-granulate in response to CD19-expressing targets. The gating strategy involved an initial gate on dump channels (CD14-PE-Cy7, CD16-PE-Cy7, Live/Dead Aqua)-negative and CD3-PE-positive cells, followed by gating on CD8-PE-Texas Red-positive cells; presented data is for the CD8+ gated population. In all cases, negative gate quadrants were established on no-stain controls.

FIG. 5, comprising FIGS. 5A through 5C, is series of images depicting the results of experiments evaluating clinical responses after infusion of CART19 cells. FIG. 5A depicts that UPN 02 was treated with two cycles of rituximab and bendamustine with minimal response (R/B, arrow). CART19 T cells were infused beginning 4 days after bendamustine only (B, arrow). The rituximab and bendamustine-resistant leukemia was rapidly cleared from blood, as indicated by a decrease in the absolute lymphocyte count (ALC) from 60,600/μl to 200/μl within 18 days of the infusion. Corticosteroid treatment was started on day 18 post infusion due to malaise and non-infectious febrile syndrome. The reference line (dotted) indicates upper limit of normal for ALC. FIG. 5B, comprising FIGS. 5B-i through 5B-vi, depicts the results of example experiments staining sequential bone marrow biopsy or clot specimens from patient UPN 01 and 03 for CD20. Pretreatment infiltration with leukemia present in both patients was absent on post treatment specimens accompanied by normalization of cellularity and trilineage hematopoiesis. UPN 01 has not had any CLL cells detected as assessed by flow cytometry, cytogenetics and fluorescence in-situ hybridization or normal B cells detected by flow cytometry in bone marrow or blood. UPN 03 had 5% residual normal CD5-negative B cells confirmed by flow cytometry on day +23, which also showed them to be polyclonal; no normal B cells were detected at day +176. FIG. 5C, comprising FIGS. 5C-i through 5C-iv depicts the results of experiments using sequential CT imaging to assess the rapid resolution of chemotherapy-resistant generalized lymphadenopathy. Bilateral axillary masses resolved by 83 (UPN 01) and 31 (UPN 03) days post infusion, as indicated by arrows and circle.

FIG. 6, comprising

FIG. 7, comprising FIGS. 7A through 7D is a series of images depicting experiments involving the direct ex vivo detection of CART19-positive cells in UPN-01 PBMC 71 days post-T cell infusion. UPN-01 PBMC collected either fresh post-apheresis on day 71 day post infusion, or frozen at the time of apheresis for manufacture of the T cell product (baseline) and viably thawed prior to the staining, were subjected to flow-cytometric analysis to detect the presence of CART19 cells that express the CAR19 moiety on the surface. To evaluate the expression of CAR19 in lymphocytes, samples were co-stained with CD3-PE and the anti-CAR19 idiotype antibody conjugated to Alexa-647, or co-stained with CD3-PE alone (FMO for CAR19). FIG. 7A depicts that an initial lymphocyte gate was established based on forward and side scatter (FSC vs SSC), followed by gating on CD3+ cells. FIG. 7B depicts CD3+ lymphocyte gate; FIG. 7C depicts CAR idiotype stain; FIG. 7D depicts CAR idiotype FMO. The CAR19-positive gate was established on the CAR19FMO samples.

FIG. 8, comprising FIGS. 8A through 8C, is a series of images depicting the gating strategy to identify CART19 expression by using polychromatic flow cytometry in UPN 03 blood specimens. The gating strategy for FIG. 8C is shown for the UPN 03 Day 56 sample and is representative of the strategy used on the UPN 03 Day 169 sample. FIG. 8A depicts primary gate: Dump (CD14, CD16, LIVE/dead Aqua) negative, CD3-positive. FIG. 8B depicts secondary gates: CD4-positive, CD8positive. FIG. 8C depicts tertiary gates: CAR19-positive and CAR19-negative, established on CAR FMO samples (right-most panels).

FIG. 10 is an image summarizing the patient demographics and response.

FIG. 12, comprising FIGS. 12A through 12D, is a series of images depicting the clinical response in a patient. FIG. 12A shows the lentiviral vector used to infect T cells from the patient. A pseudotyped, clinical-grade lentiviral vector of vesicular stomatitis virus protein G (pELPs 19-BB-z) directing expression of anti-CD19 scFv derived from FMC63 murine monoclonal antibody, human CD8α hinge and transmembrane domain, and human 4-1BB and CD3 signaling domains was produced. Details of the CAR19 transgene, at the bottom of FIG. 12A, show the major functional elements. The figure is not to scale. 3'LTR denotes 3' long terminal repeat; 5'LTR, 5' long terminal repeat; Amp R, ampicillin resistance gene; Bovine GH Poly A, bovine growth hormone with polyadenylation tail; cPPT/CTS, central polypurine tract with central termination sequence; EF-1α, elongation factor 1-alpha; env, envelope; gag, group-specific antigen; pol, HIV gene encoding polymerase and reverse transcriptase; R, repeat; RRE, rev response element; scFv, single-chain variable fragment; TM, transmembrane; and WPRE, woodchuck hepatitis virus post-transcriptional regulatory element. FIG. 12B shows serum creatinine, uric acid, and lactate dehydrogenase (LDH) levels from day 1 to day 28 after the first CART19-cell infusion. The peak levels coincided with hospitalization for the tumor lysis syndrome. FIG. 12C, comprising FIGS. 12C-i through 12C-iii, shows bone marrow-biopsy specimens obtained 3 days after chemotherapy (day −1, before CART19-cell infusion) and 23 days and 6 months after CART19-cell infusion (hematoxylin and eosin). The baseline specimen shows hypercellular bone marrow (60%) with trilineage hematopoiesis, infiltrated by predominantly interstitial aggregates of small, mature lymphocytes that account for 40% of total cellularity. The specimen obtained on day 23 shows residual lymphoid aggregates (10%) that were negative for chronic lymphoid leukemia (CLL), with a mixture of T cells and CD5-negative B cells. The specimen obtained 6 months after infusion shows trilineage hematopoiesis, without lymphoid aggregates and continued absence of CLL. FIG. 12D, comprising FIGS. 12D-i through 12D-vi, shows contrast-enhanced CT scans obtained before the patient was enrolled in the study and 31 days and 104 days after the first infusion. The preinfusion CT scan reveals 1-to-3-cm bilateral masses. Regression of axillary lymphadenopathy occurred within 1 month after infusion and was sustained. Arrows highlight various enlarged lymph nodes before therapy and lymph-node responses on comparable CT scans after therapy.

FIG. 13, comprising FIGS. 13A through 13E, is a series of images depicting serum and bone marrow cytokines before and after chimeric antigen receptor T-cell infusion. Serial measurements of the cytokine interferon-γ (FIG. 13A), the interferon-γ stimulated chemokines C—X—C motif chemokine 10 (CXCL10) (FIG. 13B) and C—X—C motif ligand 9 (CXCL9) (FIG. 13C), and interleukin-6 (FIG. 13D) were measured at the indicated time points. The increases in these inflammatory cytokines and chemokines coincided with the onset of the tumor lysis syndrome. Low levels of interleukin-6 were detected at baseline, whereas interferon-γ, CXCL9, and CXCL10 were below the limits of detection at baseline. Standard-curve ranges for the analytes and baseline values in the patient, given in parentheses, were as follows: interferon-γ, 11.2 to 23,972 pg per milliliter (1.4 pg per milliliter); CXCL10, 2.1 to 5319 pg per milliliter (274 pg per milliliter); CXCL9, 48.2 to 3700 pg per milliliter (177 pg per milliliter); interleukin-6, 2.7 to 4572 pg per milliliter (8.3 pg per milliliter); tumor necrosis factor α (TNF-α), 1.9 to 4005 pg per milliliter (not detectable); and soluble interleukin-2 receptor, 13.4 to 34,210 pg per milliliter (644 pg per milliliter). FIG. 13E, comprising FIGS. 13E-i through 13E-ii, shows the induction of the immune response in bone marrow. The cytokines TNF-α, interleukin-6, interferon-γ, chemokine CXCL9, and soluble interleukin-2 receptor were measured in supernatant fluids obtained from bone marrow aspirates on the indicated days before and after CART19-cell infusion. The increases in levels of interleukin-6, interferon-γ, CXCL9, and soluble interleukin-2 receptor coincided with the tumor lysis syndrome, peak chimeric antigen receptor T-cell infiltration, and eradication of the leukemic infiltrate.

FIG. 14, comprising FIGS. 14A through 14C, is a series of images depicting expansion and persistence of chimeric antigen receptor T cells in vivo. Genomic DNA (gDNA) was isolated from samples of the patient's whole blood (FIG. 14A) and bone marrow aspirates (FIG. 14B) collected at serial time points before and after chimeric antigen receptor T-cell infusion and used for quantitative real-time polymerase-chain-reaction (PCR) analysis. As assessed on the basis of transgenic DNA and the percentage of lymphocytes expressing CAR19, the chimeric antigen receptor T cells expanded to levels that were more than 1000 times as high as initial engraftment levels in the peripheral blood and bone marrow. Peak levels of chimeric antigen receptor T cells were temporally correlated with the tumor lysis syndrome. A blood sample obtained on day 0 and a bone marrow sample obtained on day 1 had no PCR signal at baseline. Flow-cytometric analysis of bone marrow aspirates at baseline (FIG. 14C; FIGS. 14C-i through 14C-iv) shows predominant infiltration with CD19+ CD5+ cells that were clonal, as assessed by means of immunoglobulin kappa light-chain staining, with a paucity of T cells. On day 31 after infusion, CD5+ T cells were present, and no normal or malignant B cells were detected. The numbers indicate the relative frequency of cells in each quadrant. Both the x axis and the y axis show a log 10 scale. The gating strategy involved an initial gating on CD19+ and CD5+ cells in the boxes on the left, and the subsequent identification of immunoglobulin kappa and lambda expression on the CD19+ CD5+ subset (boxes on the right)

DETAILED DESCRIPTION

Figure 1A:
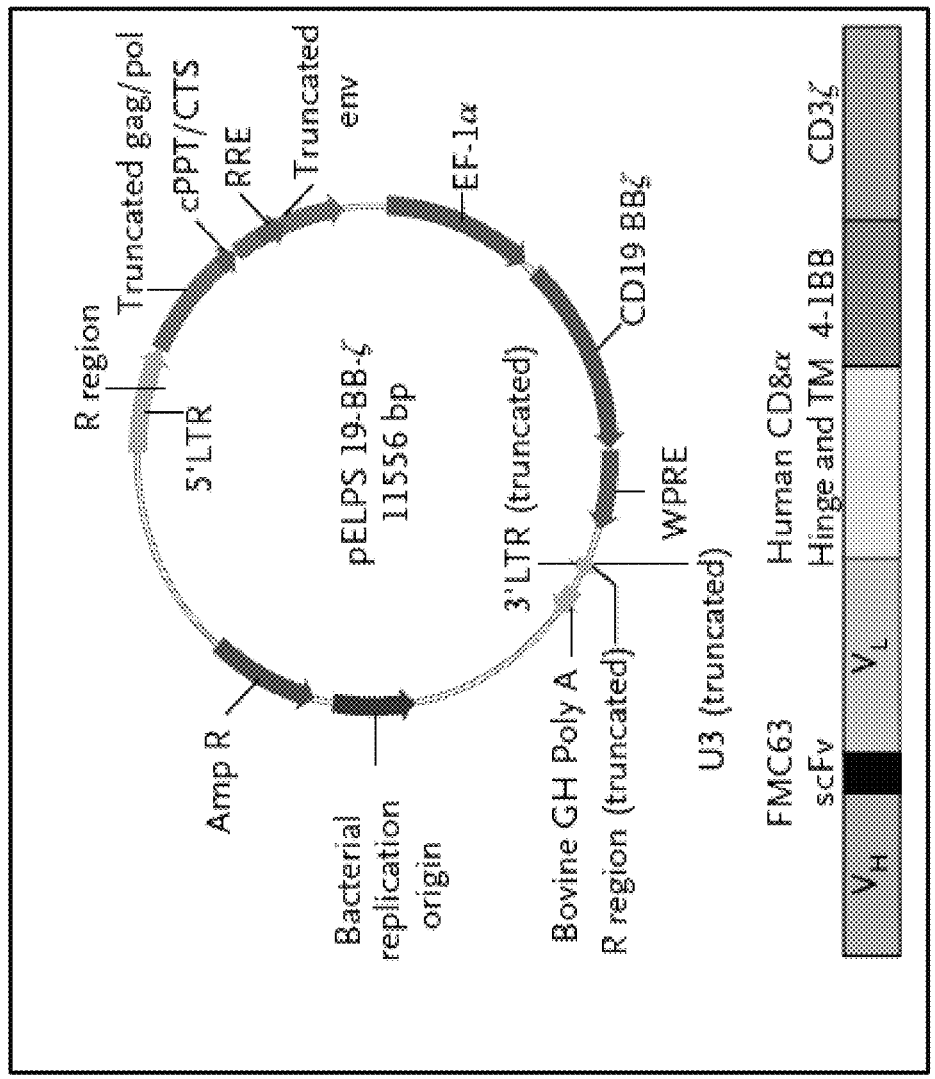
FIGS. 1A through 1C, is a series of images of the schematic representations of the gene-transfer vector and transgene, gene modified T cell manufacturing and clinical protocol design.

The invention relates to compositions and methods for treating cancer including but not limited to hematologic malignancies and solid tumors. The present invention relates to a strategy of adoptive cell transfer of T cells transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity.

The present invention relates generally to the use of T cells genetically modified to stably express a desired CAR. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular domain of the CD3-zeta chain or FcγRI protein into a single chimeric protein.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. Preferably, the transmembrane domain is the CD8α hinge domain.

With respect to the cytoplasmic domain, the CAR of the invention can be designed to comprise the CD28 and/or 4-1BB signaling domain by itself or be combined with any other desired cytoplasmic domain(s) useful in the context of the CAR of the invention. In one embodiment, the cytoplasmic domain of the CAR can be designed to further comprise the signaling domain of CD3-zeta. For example, the cytoplasmic domain of the CAR can include but is not limited to CD3-zeta, 4-1BB and CD28 signaling modules and combinations thereof. Accordingly, the invention provides CART cells and methods of their use for adoptive therapy.

In one embodiment, the CAR T cells of the invention can be generated by introducing a lentiviral vector comprising a desired CAR, for example a CAR comprising anti-CD19, CD8α hinge and transmembrane domain, and human 4-1BB and CD3zeta signaling domains, into the cells. The CAR T cells of the invention are able to replicate in vivo resulting in long-term persistence that can lead to sustained tumor control.

In one embodiment the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

In yet another embodiment, the invention relates generally to the treatment of a patient at risk of developing CLL. The invention also includes treating a malignancy or an autoimmune disease in which chemotherapy and/or immunotherapy in a patient results in significant immunosuppression in the patient, thereby increasing the risk of the patient of developing CLL.

The invention includes using T cells expressing an anti-CD19 CAR including both CD3-zeta and the 4-1BB costimulatory domain (also referred to as CART19 T cells). The CART19 T cells of the invention can undergo robust in vivo T cell expansion and can establish CD19-specific memory cells that persist at high levels for an extended amount of time in blood and bone marrow. In some instances, the CART19 T cells of the invention infused into a patient can eliminate leukemia cells in vivo in patients with advanced chemotherapy-resistant CLL. However, the invention is not limited to CART19 T cells. Rather, the invention includes any antigen binding moiety fused with one or more intracellular domains selected from the group of a CD137 (4-1BB) signaling domain, a CD28 signaling domain, a CD3zeta signal domain, and any combination thereof.

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class 1 molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class 1 molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for treating cancer among other diseases. The cancer may be a hematological malignancy, a solid tumor, a primary or a metastatizing tumor. Preferably, the cancer is a hematological malignancy, and more preferably, the cancer is Chronic Lymphocytic Leukemia (CLL). Other diseases treatable using the compositions and methods of the invention include viral, bacterial and parasitic infections as well as autoimmune diseases.

In one embodiment, the invention provides a cell (e.g., T cell) engineered to express a CAR wherein the CAR T cell exhibits an antitumor property. The CAR of the invention can be engineered to comprise an extracellular domain having an antigen binding domain fused to an intracellular signaling domain of the T cell antigen receptor complex zeta chain (e.g., CD3 zeta). The CAR of the invention when expressed in a T cell is able to redirect antigen recognition based on the antigen binding specificity. An exemplary antigen is CD19 because this antigen is expressed on malignant B cells. However, the invention is not limited to targeting CD19. Rather, the invention includes any antigen binding moiety that when bound to its cognate antigen, affects a tumor cell so that the tumor cell fails to grow, is prompted to die, or otherwise is affected so that the tumor burden in a patient is diminished or eliminated. The antigen binding moiety is preferably fused with an intracellular domain from one or more of a costimulatory molecule and a zeta chain. Preferably, the antigen binding moiety is fused with one or more intracellular domains selected from the group of a CD137 (4-1BB) signaling domain, a CD28 signaling domain, a CD3zeta signal domain, and any combination thereof.

In one embodiment, the CAR of the invention comprises a CD137 (4-1BB) signaling domain. This is because the present invention is partly based on the discovery that CAR-mediated T-cell responses can be further enhanced with the addition of costimulatory domains. For example, inclusion of the CD137 (4-1BB) signaling domain significantly increased anti-tumor activity and in vivo persistence of CAR T cells compared to an otherwise identical CAR T cell not engineered to express CD137 (4-1BB).

Composition

The present invention provides chimeric antigen receptor (CAR) comprising an extracellular and intracellular domain. The extracellular domain comprises a target-specific binding element otherwise referred to as an antigen binding moiety. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding moiety that specifically binds to an antigen on a tumor cell. In the context of the present invention, "tumor antigen" or "hyperporoliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RUL RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding moiety portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, and the like.

Depending on the desired antigen to be targeted, the CAR of the invention can be engineered to include the appropriate antigen bind moiety that is specific to the desired antigen target. For example, if CD19 is the desired antigen that is to be targeted, an antibody for CD19 can be used as the antigen bind moiety for incorporation into the CAR of the invention.

In one embodiment, the antigen binding moiety portion of the CAR of the invention targets CD19. Preferably, the antigen binding moiety portion in the CAR of the invention is anti-CD19 scFV, wherein the nucleic acid sequence of the anti-CD19 scFV comprises the sequence set forth in SEQ ID: 14. In one embodiment, the anti-CD19 scFV comprise the nucleic acid sequence that encodes the amino acid sequence of SEQ ID NO: 20. In another embodiment, the anti-CD19 scFV portion of the CAR of the invention comprises the amino acid sequence set forth in SEQ ID NO: 20.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Preferably, the transmembrane domain in the CAR of the invention is the CD8 transmembrane domain. In one embodiment, the CD8 transmembrane domain comprises the nucleic acid sequence of SEQ ID NO: 16. In one embodiment, the CD8 transmembrane domain comprises the nucleic acid sequence that encodes the amino acid sequence of SEQ ID NO: 22. In another embodiment, the CD8 transmembrane domain comprises the amino acid sequence of SEQ ID NO: 22.

In some instances, the transmembrane domain of the CAR of the invention comprises the CD8α hinge domain. In one embodiment, the CD8 hinge domain comprises the nucleic acid sequence of SEQ ID NO: 15. In one embodiment, the CD8 hinge domain comprises the nucleic acid sequence that encodes the amino acid sequence of SEQ ID NO: 21. In another embodiment, the CD8 hinge domain comprises the amino acid sequence of SEQ ID NO: 21.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.

In one embodiment, the cytoplasmic domain in the CAR of the invention is designed to comprise the signaling domain of 4-1BB and the signaling domain of CD3-zeta, wherein the signaling domain of 4-1BB comprises the nucleic acid sequence set forth in SEQ ID NO: 17 and the signaling domain of CD3-zeta comprises the nucleic acid sequence set forth in SEQ ID NO: 18.

In one embodiment, the cytoplasmic domain in the CAR of the invention is designed to comprise the signaling domain of 4-1BB and the signaling domain of CD3-zeta, wherein the signaling domain of 4-1BB comprises the nucleic acid sequence that encodes the amino acid sequence of SEQ ID NO: 23 and the signaling domain of CD3-zeta comprises the nucleic acid sequence that encodes the amino acid sequence of SEQ ID NO: 24.

In one embodiment, the cytoplasmic domain in the CAR of the invention is designed to comprise the signaling domain of 4-1BB and the signaling domain of CD3-zeta, wherein the signaling domain of 4-1BB comprises the amino acid sequence set forth in SEQ ID NO: 23 and the signaling domain of CD3-zeta comprises the amino acid sequence set forth in SEQ ID NO: 24.

Vectors

The present invention encompasses a DNA construct comprising sequences of a CAR, wherein the sequence comprises the nucleic acid sequence of an antigen binding moiety operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the invention comprises anti-CD19 scFv, human CD8 hinge and transmembrane domain, and human 4-1BB and CD3zeta signaling domains. In one embodiment, the CAR of the invention comprises the nucleic acid sequence set forth in SEQ ID NO: 8. In another embodiment, the CAR of the invention comprises the nucleic acid sequence that encodes the amino acid sequence of SEQ ID NO: 12. In another embodiment, the CAR of the invention comprises the amino acid sequence set forth in SEQ ID NO: 12.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399, 346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_c$ cells. Accordingly, depending on the purpose of treatment, infusing a subject with a T cell population comprising predominately of $T_H$ cells may be advantageous. Similarly, if an antigen-specific subset of $T_c$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) transduced with a lentiviral vector (LV). For example, the LV encodes a CAR that combines an antigen recognition domain of a specific antibody with an intracellular domain of CD3-zeta, CD28, 4-1BB, or any combinations thereof. Therefore, in some instances, the transduced T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, it was unexpected that the CART19 cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, a CART19 cells elicits an immune response specific against cells expressing CD19.

While the data disclosed herein specifically disclose lentiviral vector comprising anti-CD19 scFv derived from FMC63 murine monoclonal antibody, human CD8α hinge and transmembrane domain, and human 4-1BB and CD3zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen bind moiety portion of the CAR of the invention is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR can be designed to target mesothelin to treat mesothelioma, pancreatic cancer, ovarian cancer, and the like.

In one embodiment, the CAR can be designed to target CD33/IL3Ra to treat acute myelogenous leukemia and the like.

In one embodiment, the CAR can be designed to target c-Met to treat triple negative breast cancer, non-small cell lung cancer, and the like.

In one embodiment, the CAR can be designed to target PSMA to treat prostate cancer and the like.

In one embodiment, the CAR can be designed to target Glycolipid F77 to treat prostate cancer and the like.

In one embodiment, the CAR can be designed to target EGFRvIII to treat gliobastoma and the like.

In one embodiment, the CAR can be designed to target GD-2 to treat neuroblastoma, melanoma, and the like.

In one embodiment, the CAR can be designed to target NY-ESO-1 TCR to treat myeloma, sarcoma, melanoma, and the like.

In one embodiment, the CAR can be designed to target MAGE A3 TCR to treat myeloma, sarcoma, melanoma, and the like.

However, the invention should not be construed to be limited to solely to the antigen targets and diseases disclosed herein. Rather, the invention should be construed to include any antigenic target that is associated with a disease where a CAR can be used to treat the disease.

The CAR-modified T cells of the invention may also serve as a type of vaccine for ex vivo immunization and/or in vivo therapy in a mammal Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of CCL. In certain embodiments, the cells of the invention are used in the treatment of patients at risk for developing CCL. Thus, the present invention provides methods for the treatment or prevention of CCL comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

T Cells Expressing Chimeric Receptors Establish Memory and Potent Antitumor Effects in Patients with Advanced Leukemia Lymphocytes engineered to express chimeric antigen receptors (CARs) have demonstrated minimal in vivo expansion and antitumor effects in previous clinical trials. The results presented herein demonstrate that that CAR T cells containing CD137 have potent non-cross resistant clinical activity following infusion in three of three patients treated with advanced chronic lymphocytic leukemia (CLL). The engineered T cells expanded more than a thousand-fold in vivo, trafficked to bone marrow and continued to express functional CARs at high levels for at least 6 months. On average, each infused CAR+ T cell eradicated at least 1000 CLL cells. A CD19 specific immune response was demonstrated in the blood and bone marrow, accompanied by complete remission in two of three patients. A portion of the cells persist as memory CAR+ T cells, indicating the potential of this non-MHC restricted approach for the effective treatment of B cell malignancies.

The materials and methods employed in these experiments are now described.

Materials and Methods

General Laboratory Statement

Research sample processing, freezing, and laboratory analyses were performed in the Translational and Correlative Studies Laboratory at the University of Pennsylvania which operates under principles of Good Laboratory Practice with established SOP and/or protocols for sample receipt, processing, freezing, and analysis. Assay performance and data reporting conforms with MIATA guidelines (Janetzki et al., 2009, Immunity 31:527-528).

Protocol Design

Figure 1B:
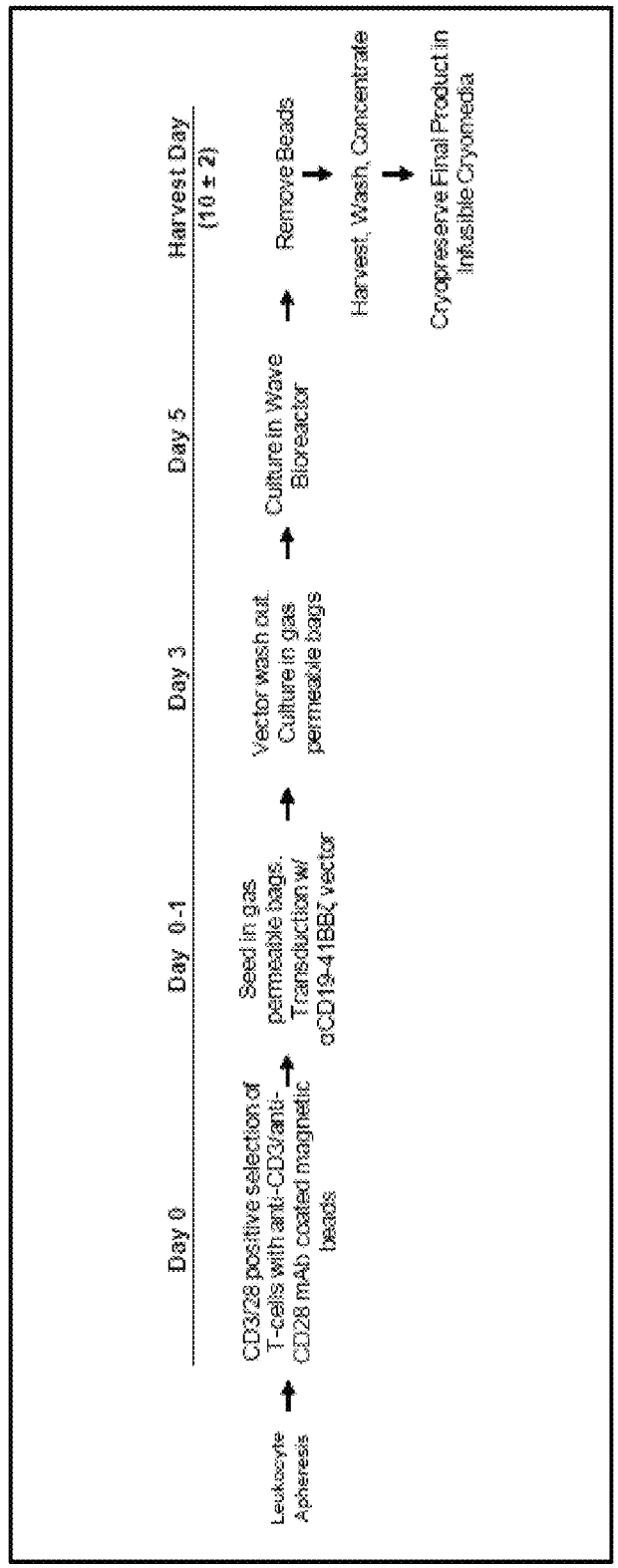
Figure 1C:
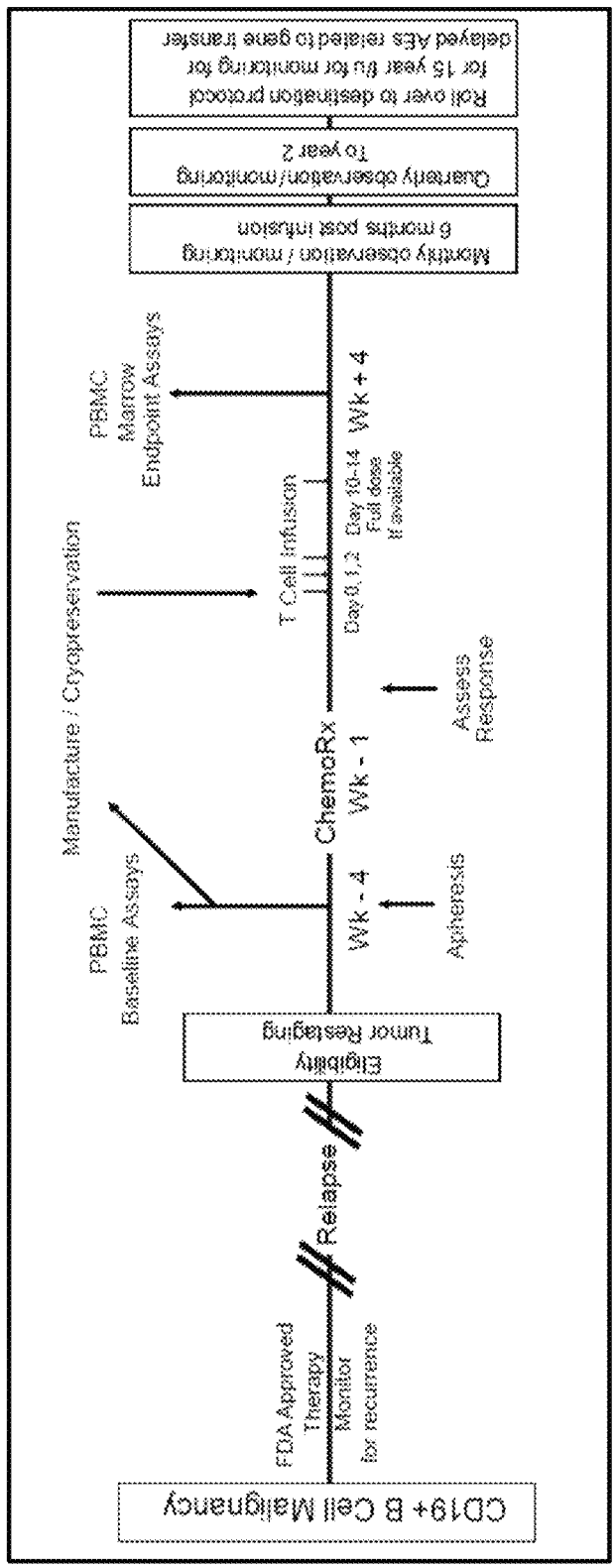

The clinical trial (NCT01029366) was conducted as diagramed in FIG. 1. Patients with CD19 positive hematologic malignancy with persistent disease following at least two prior treatment regimens and who were not eligible for allogeneic stem cell transplantation were eligible for the trial. Following tumor restaging, peripheral blood T cells for CART19 manufacturing were collected by apheresis and the subjects given a single course of chemotherapy as specified in FIG. 10 during the week before infusion. CART19 cells were administered by intravenous infusion using a 3 day split dose regimen (10%, 30% and 60%) at the dose indicated in FIG. 10 and if available, a second dose was administered on day 10; only patient UPN 02 had sufficient cells for a second infusion. Subjects were assessed for toxicity and response at frequent intervals for at least 6 months. The protocol was approved by the US Food and Drug Administration, the Recombinant DNA Advisory Committee and the Institutional Review Board of the University of Pennsylvania. The first day of infusion was set as study Day 0.

Subjects: Clinical Summary

The clinical summaries are outlined in FIG. 10 and detailed histories are provided elsewhere herein. Patient UPN 01 was first diagnosed with stage II B cell CLL at age 55. The patient was asymptomatic and observed for approximately 1½ years until requiring therapy for progressive lymphocytosis, thrombocytopenia, adenopathy, and splenomegaly. Over the course of time, the patient received prior lines of therapy. The most recent therapy was 2 cycles of pentostatin, cyclophosphamide and rituximab 2 months prior to CART19 cell infusion with a minimal response. The patient then received one cycle of bendamustine as lymphodepleting chemotherapy prior to CART-19 cell infusion.

Figure 5A:
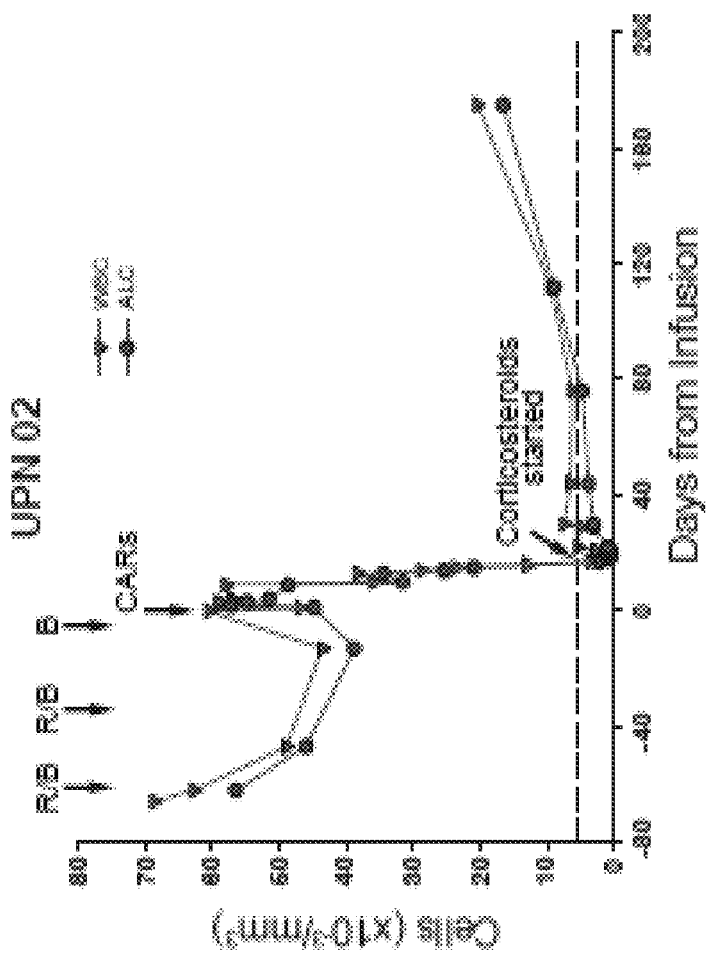

Patient UPN 02 was first diagnosed with CLL at age 68 when the patient was presented with fatigue and leukocytosis. The patient was relatively stable for 4 years when the patient developed progressive leukocytosis (195,000/µl), anemia and thrombocytopenia requiring therapy. Karyotypic analysis showed that the CLL cells had deletion of chromosome 17p. Because of progressive disease, the patient was treated with alemtuzumab with a partial response but within one and a half years the patient had progressive disease. The patient was retreated with alemtuzumab for 18 weeks with a partial response and a 1 year progression free interval. The patient then received 2 cycles of bendamustine with rituximab without a significant response (FIG. 5A). The patient received single agent bendamustine as lymphodepleting chemotherapy prior to CART-19 cell infusion.

Patient UPN 03 presented at age 50 with asymptomatic stage I CLL and was followed with observation for years. The patient had progressive leukocytosis (white blood count 92,000/µl) and progressive adenopathy requiring therapy. The patient received 2 cycles of rituximab with fludarabine that resulted in normalization of blood counts and significant improvement though not complete resolution in adenopathy. The patient had an approximately 3 year progression free interval. Karyotypic testing showed cells to contain deletion of chromosome 17p with FISH demonstrating a TP53 deletion in 170 of 200 cells. Over the next years the patient required 3 different lines of therapy (FIG. 10) for progressive leukocytosis and adenopathy, last receiving alemtuzumab with a partial response 6 months prior CART19 cell infusion. The patient received pentostatin and cyclophosphamide as lymphodepleting chemotherapy prior to CART-19 cell infusion.

Vector Production

The CD19-BB-z transgene (GeMCRIS 0607-793) was designed and constructed as described (Milone et al., 2009, Mol Ther. 17:1453-1464). Lentiviral vector was produced according to current good manufacturing practices using a three-plasmid production approach at Lentigen Corporation as described (Zufferey et al., 1997, Nature biotechnol 15:871-875).

Preparation of CART19 Cell Product

Methods of T cell preparation using paramagnetic polystyrene beads coated with anti-CD3 and anti-CD28 monoclonal antibodies have been described (Laport et al., 2003, Blood 102: 2004-2013). Lentiviral transduction was performed as described (Levine et al., 2006, Proc Natl Acad Sci USA 103:17372-17377).

Methods for Tumor Burden Calculation

CLL burden at baseline was estimated as shown in FIG. 10. The amount of CLL cells were calculated in bone marrow, blood, and secondary lymphoid tissues as described below.

Bone marrow:

In healthy adults, the bone marrow represents approximately 5% of total body weight (Woodard et al., 1960, Phys Med Biol, 5:57-59; Bigler et al., 1976, Health Phys 31:213-218). The bone marrow in iliac crest samples has an increasing percentage of inactive (fatty) marrow with age, rising from 20% of the total marrow at age 5 to about 50% by age 35, when it remains stable until age 65, and then rises to about 67% inactive marrow by age 75 (Hartsock et al., 1965, Am J Clin Path 43:326-331). The international reference value for the total skeletal weight of active (red) and inactive (fatty) marrow for males at age 35 is currently set at 1170 g and 2480 g, respectively (Basic anatomical and physiological data for use in radiological protection: The Skeleton in Annals of the ICRP, Vol. 25 (ed. Smith, H.) 58-68 (A report of a Task Group of Committee 2 of the International Commission on Radiological Protection, Oxford, 1995)). Adult males between ages 35 to 65 have marrow that represents 5.0% total of body weight, comprised of 1.6% as active (red) marrow and 3.4% as inactive (fatty) marrow (Basic anatomical and physiological data for use in radiological protection: The Skeleton in Annals of the ICRP, Vol. 25 (ed. Smith, H.) 58-68 (A report of a Task Group of Committee 2 of the International Commission on Radiological Protection, Oxford, 1995)). Based on the bone marrow biopsy and aspirate specimens, the weight of CLL cells for the three patients at baseline was calculated as shown in the Table 1. These estimates of total CLL marrow mass were then converted to total CLL cell number in the marrow using 1 Kg=$10^{12}$ cells, and the resulting numbers are shown in FIG. 10. These calculations are based on the assumption that the CLL has a uniform distribution in the bone marrow. For patient UPN 01, calculations are shown for a marrow biopsy that was obtained before bendamustine chemotherapy, and for an aspirate obtained after bendamustine and pre-CART19 infusion. The numbers are less precise for the day-1 aspirate compared to the day −14 biopsy specimen due to technical limitations of the day-1 aspirate. Patient UPN 02 had a single pre-treatment biopsy specimen showing complete replacement of marrow by CLL. This patient had an unchanged specimen on day 30 post CART19. The marrow burden for patient UPN 03 was calculated based on a post-chemotherapy and pre-CART19 biopsy.

TABLE 1

Marrow Mass

|  | Wt of Active Marrow (kg) | Wt of Inactive Morrow (kg) | Total marrow (kg) |
|---|---|---|---|
| Normal males (ICRP reference standard) | 1.17 | 2.48 | 3.65 |
| UPN 01 day −14 (95% cellular) | 3.47 | 0.18 | 3.65 |
| UPN 02 day −47 (95% cellular) | 3.47 | 0.18 | 3.65 |
| UPN 03 day −1 (60% cellular) | 2.19 | 1.46 | 3.65 |

| | Wt of CLL (kg) |
|---|---|
| UPN 01 day −14 (70% CLL) | 2.43 |
| UPN 01 day −1 (50% CLL by clot) | 1.73 |
| UPN 02 day −47 (>95% CLL) | 3.29 |
| UPN 03 day −1 (40% CLL) | 0.88 |

Blood:

Only patient UPN 02 had substantial CLL tumor burden in the blood pre-CART19 infusion. Flow cytometry showed that the cells had a typical phenotype as a clonal population with a dim surface kappa-restricted CD5+ CD10−CD19+ CD20(dim)+ CD23(variable)+ IgM-B cell population. Approximately 35% of the CLL cells coexpressed CD38. The CLL burden did not clear with 3 cycles of bendamustine chemotherapy and was present at the time of CART19 infusions. At the time of CART19 infusion, the CLL count in blood was 55,000 cells/μL. Assuming a blood volume of 5.0 L, patient UPN 02 had 2.75×$10^{11}$ CLL cells in blood on day 0. Given the normal overall WBC in patients UPN 01 and 03, the circulating disease burden in these patients was not calculated, which would lead to a slight underestimate of total body burden.

Secondary lymphoid tissues:

The volume of lymphadenopathy and splenomegaly was quantified on axial CT scans using FDA-approved software. The volumes are for chest, abdomen and pelvis only. Masses from the T1 vertebral body to the level of the bifurcation of the common femoral artery were measured in all patients, and in some, the nodes in the inguinal area were also included. Nodes in the head/neck and extremities were excluded from analysis and excluded from the baseline CLL target cell number, which would also lead to a slight underestimate of total body burden. Patients UPN 01 and 03 have had sustained complete remissions beyond 6 months, and thus the formula (baseline volume-month 3 volume) was used to determine the reduction in tumor burden from baseline; patient UPN 02 had stable disease in adenopathy, and thus the baseline tumor mass is estimated by subtracting the reference splenic volume from age matched healthy males (Harris et al., 2010, Eur J Radiol 75:e97-e101). Baseline tumor mass was converted to CLL cells using a density approach (1 Kg/L density, and 1 Kg=1012 cells) cells or a volume approach (CLL cells are 10 μM diameter or 600 fL, assuming spherical shape), and both values presented in FIG. 10. The tumor volumes in secondary lymphoid tissues in the three patients are shown below in Table 2 as calculated from the available CT scans.

TABLE 2

Tumor Volumes

| Patient | Study Day | LN volume (mm3) | Spleen volume (mm3) | Total volume (mm3) |
|---|---|---|---|---|
| UPN 01 | −37 | 239655 | 1619180 | 1858835 |
| | 1 month | 105005 | 1258575 | 1363580 |
| | 3 month | 65060 | 1176625 | 1241685 |
| UPN 02 | −24 | 115990 | 1166800 | 1282790 |
| | 1 month | 111755 | 940960 | 1052715 |
| UPN 03 | −10 | 239160 | 435825 | 674985 |
| | 1 month | 111525 | 371200 | 482725 |
| | 3 month | 47245 | 299860 | 347105 |

The baseline CT scan for patient UPN 01 was performed 8 days after 2 cycles of pentostatin/cyclophosphamide/rituximab, and showed no response to this chemotherapy regimen compared to the previous CT scan. The patient had one cycle of bendamustine before CART19, and thus, the change in tumor volume from Day −37 to Day +31 for UPN 01 cannot exclude the potential contribution of the bendamustine as well as CART19. Similarly, the change in tumor volume for UPN 03 reflects the combined effect of 1 cycle of pentastatin/cyclophosphamide and CART19.

Method for Estimating Effective In Vivo E:T Ratio in Patients

Figure 6A:
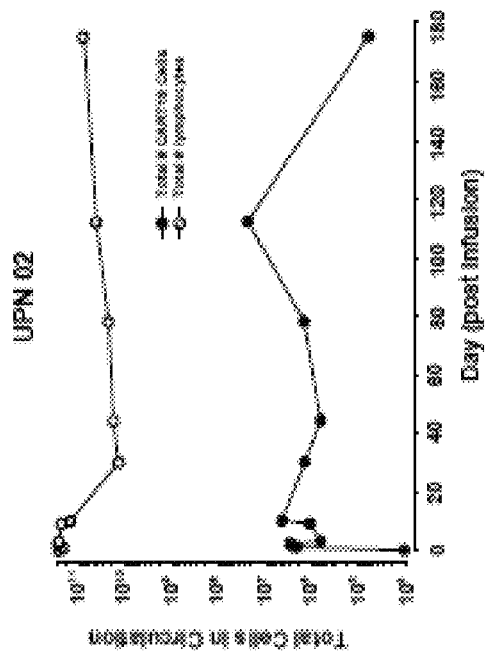
FIGS. 6A through 6C, is a series of images depicting absolute lymphocyte counts and total CART19+ cells in circulation for UPN 01, 02, 03. The total number of lymphocytes (Total normal and CLL cells) vs. Total CART19+ cells in circulation is plotted for all 3 subjects using the absolute lymphocyte count from CBC values, and assuming a 5.0 L volume of blood. The total number of CART19 cells in circulation was calculated by using the tandem CBC values with absolute lymphocyte counts and the Q-PCR marking values as depicted in FIG. 2, converting copies/μg DNA to average % marking as described elsewhere herein. The Q-PCR % marking was found to correlate closely (<2 fold variation) with the flow cytometric characterization of the infusion products and with data from samples where concomitant flow cytometry data was available to directly enumerate CART19 cells by staining.
Figure 6B:
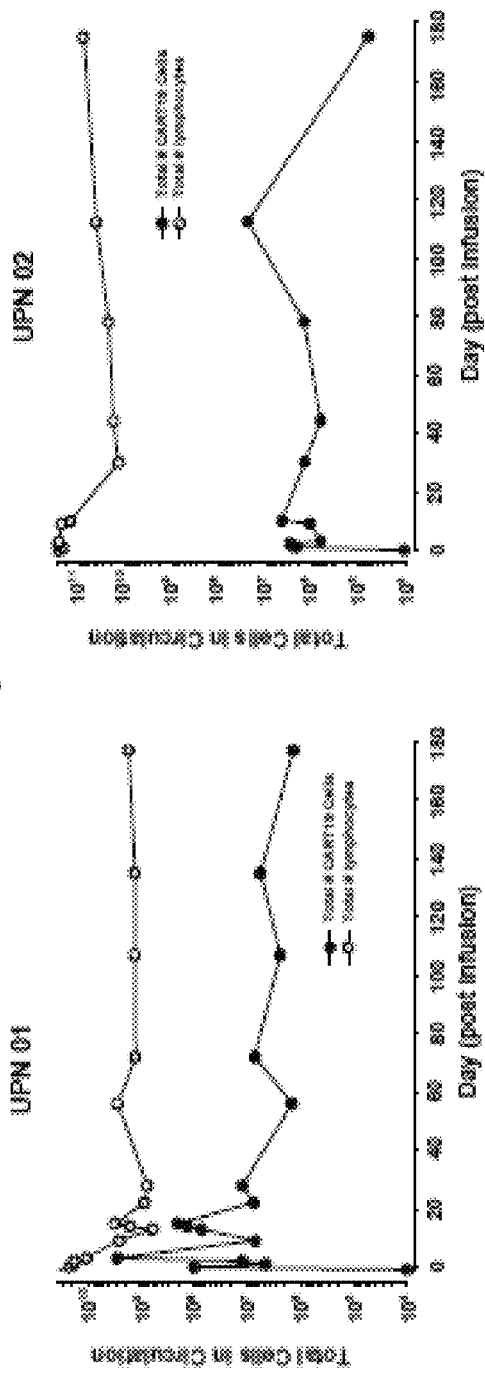
Figure 6C:
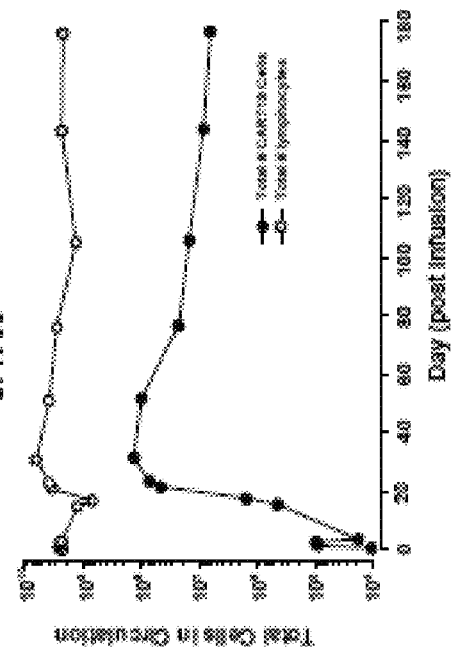
Figure 9:
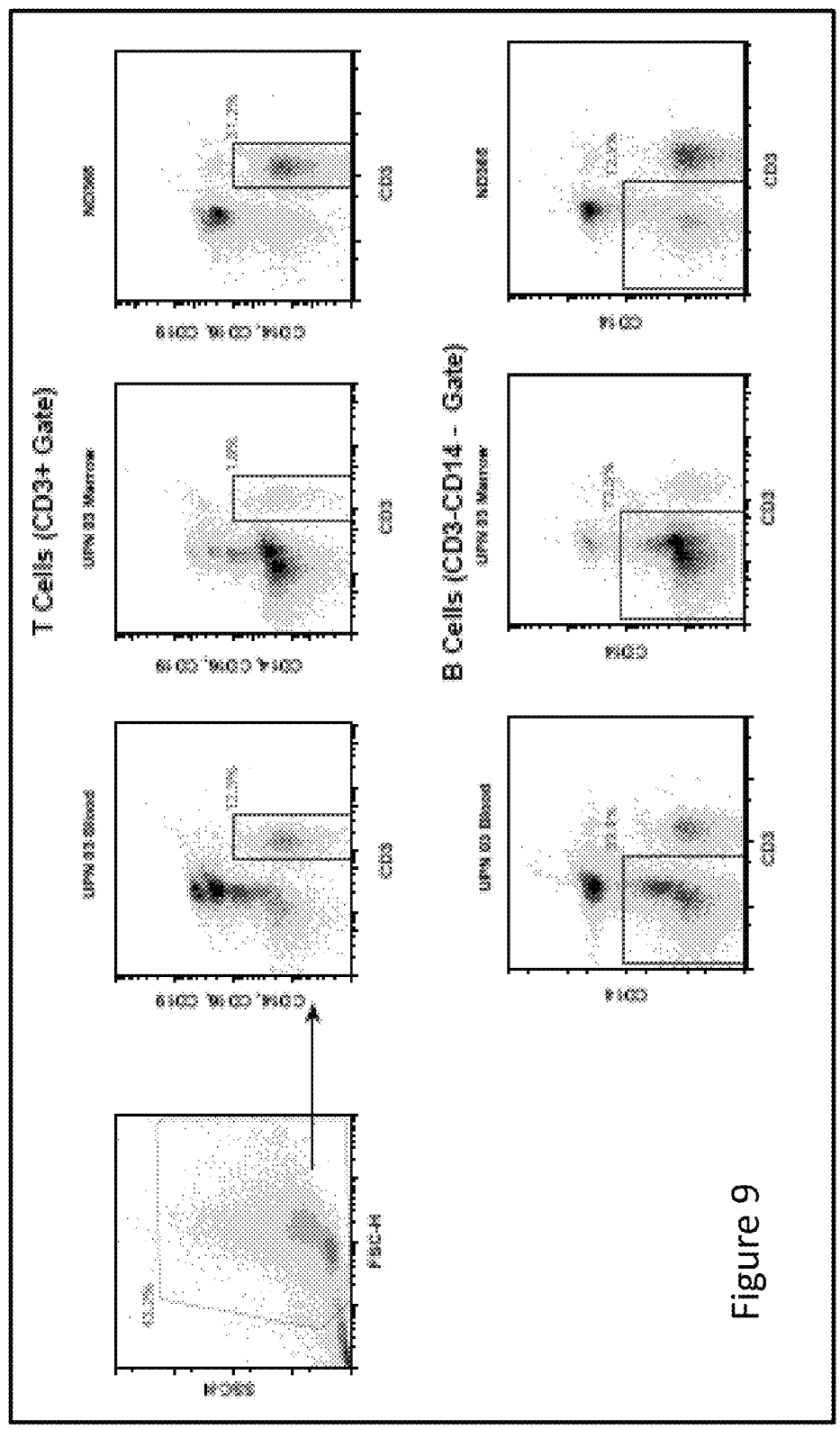
FIG. 9 depicts the gating strategy to directly identify CART19 expression and B cells in blood and marrow specimens. The gating strategy for FIG. 4A, which shows detection of CAR-expressing CD3+ lymphocytes and absence of B cells in periphery and marrow: Leftplot: Cell gate; Upper panel: positive gate for CD3+ cells, Lower panel: negative gate (CD14-negative, CD3-negative) for B cells. NC365, peripheral blood control cells from a healthy donor

The E:T ratio of infused CAR T cells to the number of tumor cells killed was calculated using the number of tumor cells present at the time of CAR T cell injection and the number of CAR T cells injected (Carpenito et al., 2009, Proc Natl Acad Sci USA 106:3360-3365). For the present invention, the number of CART19+ T cells injected as shown on FIG. 10 was used because it is not possible to determine the absolute number of CART19+ T cells present in vivo with sufficient accuracy or precision. The available data on CART19 expansion in blood and marrow is robust as depicted in FIG. 2 and FIG. 6. However it was not possible to determine the trafficking of CART19 to other sites such as secondary lymphoid tissues, creating substantial uncertainty on the total number of CART19 cells achieved in vivo at the time of maximal tumor reduction. The calculated values from Table 3 were used to derive the effective E:T ratios.

TABLE 3

Calculated CART19 E:T ratios achieved in vivo

| Patient | Tumor Burden (Baseline and Delta) | | | | CART19+ cells Infused | In Vivo E:T |
|---|---|---|---|---|---|---|
| | Bone marrow Baseline | Blood Baseline | Nodes/Spleen[1] Baseline | Total Change in CLL Burden | | |
| UPN 01 | 1.70E+12 | N/A | 8.1E+11 | 2.51E+12 | 1.13E+09 | 1:2200 |
| UPN 02 | 3.20E+12 | 2.75E+11 | 1.6E+12 | 2.74E+11[2] | 5.80E+08 | 1:1000 |
| UPN 03 | 8.60E+11 | N/A | 4.4E+11 | 1.32E+12 | 1.42E+07 | 1:93,000 |
| | | | | | Range | 1000-93,000 |

[1] = average of density and volume method
[2] = Patient UPN02 did not respond in bone marrow and had a partial reduction in adenopathy (3.1E+11 cells) in the tumor masses measured by CT in spleen and lymph nodes. See FIG. 5A for response in blood.

Sample Processing and Freezing

Samples (peripheral blood, marrow) were collected in lavender top (K2EDTA,) or red top (no additive) vacutainer tubes (Becton Dickinson) and delivered to the TCSL within 2 hours of draw. Samples were processed within 30 minutes of receipt according to established laboratory SOP. Peripheral blood and marrow mononuclear cells were purified via Ficoll density gradient centrifugation using Ficoll-Paque (GE Health care, 17-1440-03) and frozen in RPMI (Gibco 11875-135) supplemented with 4% human serum albumin (Gemini Bio-Products, 800-120), 2% Hetastarch (Novaplus, NDC0409-7248-49), and 10% DMSO (Sigma, D2650) using 5100 Cryo 1° freezing containers; after 24-72 hours at −80° C., cells were transferred to liquid Nitrogen for long-term storage. Apheresis samples were obtained through the Hospital of the University of Pennsylvania Blood Bank and processed in the CVPF by Ficoll gradient purification and frozen as above. Viability immediately post-thaw was greater than 85% when assessed. For serum isolation, samples were allowed to coagulate for 1.5-2 hours at room temperature; serum isolated by centrifugation, and single use 100 µl aliquots frozen at −80° C.

Cell Lines

K562 (CML, CD19-negative) was obtained from ATCC (CCL-243). K562/CD19, a generous gift of Carmine Carpenito, and is K562 lentivirally transduced at 100% frequency to express the CD19 molecule. NALM-6, a CD19-positive non-T, non-B ALL precursor B cell line (Hurwitz et al., 1979, Int J Cancer 23:174-180), and confirmed to express the CD19 antigen was a generous gift of Laurence Cooper. The above cell lines were maintained in R10 medium (RPMI 1640 (Gibco, 11875) supplemented with 10% fetal bovine serum (Hyclone), and 1% Pen-Strep (Gibco, 15140-122). Peripheral mononuclear cells (ND365) from a healthy donor were obtained by apheresis from the Human Immunology Core at the University of Pennsylvania, processed, and frozen as above.

DNA Isolation and Q-PCR Analysis

Whole-blood or marrow samples were collected in lavender top (K3EDTA) BD vacutainer tubes (Becton Dickinson). Genomic DNA was isolated directly from whole-blood using QTAamp DNA blood midi kits (Qiagen) and established laboratory SOP, quantified by spectrophotometer, and stored at −80° C. Q-PCR analysis on genomic DNA samples was performed in bulk using 123-200 ng genomic DNA/timepoint, ABI Taqman technology and a validated assay to detect the integrated CD19 CAR transgene sequence. Pass/fail parameter ranges, including standard curve slope and $r^2$ values, ability to accurately quantify a reference sample (1000 copies/plasmid spike) and no amplification in healthy donor DNA sample were calculated from the qualification studies and pre-established acceptance ranges. Primer/probes for the CD19 CAR transgene were as described (Milone et al., 2009, Mol Ther 17:1453-1464). To determine copy number/unit DNA an 8-point standard curve was generated consisting of $10^6$-5 copies lentivirus plasmid spiked into 100 ng non-transduced control genomic DNA. Each data-point (samples, standard curve, reference samples) was evaluated in triplicate with average values reported. For patient UPN 01, all reported values were derived from a positive Ct value in 3/3 replicates with % CV less than 0.46%. For patient UPN 02, with the exception of the day +177 sample (⅔ replicates positive, high % CV), all reported values were derived from a positive Ct value in 3/3 replicates with % CV less than 0.72%. For patient UPN 03, with the exception of the day +1 sample (⅔ replicates positive, 0.8% CV) and the day +3 sample (⅔ replicates positive, 0.67% CV), all reported values were derived from a positive Ct value in 3/3 replicates with % CV less than 1.56%. The lower limit of quantification (LLOQ) for the assay was determined from the standard curve at 2 copies/microgram DNA (10 copies/200 ng input DNA); average values below LLOQ (i.e. reportable not quantifiable) are considered approximate. A parallel amplification reaction to control for the quality of interrogated DNA was performed using 12-20 ng input genomic DNA, a primer/probe combination specific for non-transcribed genomic sequence upstream of the CDKN1A gene (GENEBANK: Z85996) (sense primer: GAAAGCTGACTGCCCCTATTTG; SEQ ID NO. 25, antisense primer: GAGAGGAAGTGCTGGGAACAAT; SEQ ID NO. 26, probe: VIC-CTC CCC AGT CTC TTT; SEQ ID NO. 27), and an 8 point standard curve created by dilution of control genomic DNA; these amplification reactions produced a correction factor (CF) (ng detected/ng input). Copies transgene/microgram DNA were calculated according to the formula: copies calculated from CD19 standard curve/input DNA (ng)×CF×1000 ng. Accuracy of this assay was determined by the ability to quantify marking of the infused cell product by Q-PCR according to the formula: Average marking=detected copies/input DNA×6.3 pg DNA/male somatic cell x CF versus transgene positivity by flow cytometry using CAR-specific detection reagents. These blinded determinations generated 22.68% marking for the UPN 01 infusion product (22.6% by flow cytometry), 32.33% marking for UPN 02 infusion product (23% by flow cytometry), and 4.3% marking for the UPN 03 infusion product (4.7% marking by flow cytometry).

Cytokine Analyses

Quantification of soluble cytokine factors was performed using Luminex bead array technology and kits purchased from Life technologies (Invitrogen). Assays were performed as per the manufacturer protocol with an 8 point standard curve generated using a 3-fold dilution series. Each standard point and sample was evaluated in duplicate at 1:3 dilution; calculated % CV for the duplicate measures were less than 15%. Data were acquired on a Bioplex 200 and analyzed with Bioplex Manager version 5.0 software using 5-parameter logistic regression analysis. Standard curve quantification ranges were determined by the 80-120% (observed/expected value) range. Individual analyte quantification ranges are reported in the Figure legends.

Cellular Assay to Detect CAR Function

Cells were evaluated for functionality after thaw and overnight rest in TCM by measuring CD107 degranulation in response to target cells. Degranulation assays were performed using $1\times10^6$ PBMC and $0.25\times10^6$ target cells in a final volume of 500 µl in 48-well plates for 2 hours at 37° C. in the presence of CD49d (Becton Dickinson), anti-CD28, monensin (e-Bioscience) and CD107a-FITC antibody (eBiosciences) essentially as described (Betts et al., 2003, J Immunol Methods 281:6578).

Antibody Reagents

The following antibodies were used for these studies: MDA-CAR, a murine anti CD19 CAR antibody conjugated to Alexa647 was a generous gift of Drs. Bipulendu Jena and Laurence Cooper (MD Anderson Cancer Center). For multiparametric immunophenotyping and functional assays: anti-CD3-A700, anti-CD8-PE-Cy7, anti-PD-1-FITC anti-CD25-AF488, anti-CD28-PercP-Cy5.5, anti-CD57-eF450, anti-CD27-APC-eF780, anti-CD17-APC-eF780, anti-CD45RA-eF605NC, CD107a-FITC (all from e-Bioscience), anti-CD4-PE-Texas Red and Live/Dead Aqua (from Life Technologies) and anti-CD14-V500, anti-CD16-V500 (from Becton Dickinson). For general immunophenotyping: CD3-PE, CD14-APC, CD14-PE-Cy7, CD16-FITC, CD16PE-Cy7, CD19-PE-Cy7, CD20-PE, all from Becton Dickinson.

Multi-Parameter Flow Cytometry

Cells were evaluated by flow cytometry either fresh after Ficoll-Paque processing or, if frozen, after overnight rest at a density of $2\times10^6$ cells/ml in T cell medium (TCM) (X-vivo 15 (Lonza, 04-418Q) supplemented with 5% human AB serum (GemCall, 100-512), 1% Hepes (Gibco, 15630-080), 1% Pen-Strep (Gibco, 15140-122), 1% Glutamax (Gibco, 35050-061), and 0.2% N-Acetyl Cysteine (American Regent, NDC0517-7610-03). Multi-parametric immunophenotyping was performed on $4\times10^6$ total cells/condition, using FMO stains as described in the text. Cells were stained at a density of $1\times10^6$ cells/100 µl PBS for 30 minutes on ice using antibody and reagent concentrations recommended by the manufacturer, washed, re-suspended in 0.5% paraformaldehyde and acquired using a modified LSR11 (BD Immunocytometry systems) equipped with Blue (488 nm) Violet (405 nm), Green (532), and Red (633 nm) lasers and appropriate filter sets for the detection and separation of the above antibody combinations. A minimum of 100,000 CD3+ cells were acquired) for each stain. For functional assays, cells were washed, stained for surface markers, re-suspended in 0.5% paraformaldehyde and acquired as above; a minimum of 50,000 CD3+ events were collected for each staining condition. Compensation values were established using single antibody stains and BD compensation beads (Becton Dickinson) and were calculated and applied automatically by the instrument. Data were analyzed using FlowJo software (Version 8.8.4, Treestar). For general immunophenotyping cells were acquired using an Accuri C6 cytometer equipped with a Blue (488) and Red (633 nm) laser. Compensation values were established using single antibody stains and BD compensation beads (Becton Dickinson) and were calculated manually. Data were analyzed using C-Flow software analysis package (version 1.0.264.9, Accuri cytometers).

Patient Past Medical Histories and Response to Therapy

The clinical treatment summaries are outlined in FIG. 10. Patient UPN 01 was first diagnosed with stage II B cell CLL at age 55. The patient was asymptomatic and observed for approximately 1½ years until requiring therapy for progressive lymphocytosis, thrombocytopenia, adenopathy, and splenomegaly. After 4 cycles of fludarabine the patient had complete normalization of blood counts and a complete response by CT scans. Progression was noted within 5 months with asymptomatic lymphocytosis, thrombocytopenia, and increasing adenopathy. The patient was observed without symptoms for approximately 3 years, and later required treatment with Rituximab and fludarabine for progressive leukocytosis, anemia, and thrombocytopenia. The patient was treated with 4 cycles of rituximab with fludarabine with partial improvement in blood counts. The patient again had progression within one year requiring therapy manifested by leukocytosis (WBC 150,000/µl) and thrombocytopenia (platelets 30,000/µl) and was treated with alemtuzumab with normalization of blood counts. Progression was noted within 13 months. The patient then received single agent rituximab without a significant response and followed by rituximab, cyclophosphamide, vincristine, and prednisone (R-CVP) for 2 cycles with minimal response and followed by lenalidomide. Lenalidomide was discontinued because of toxicity. The patient received 2 cycles of pentostatin, cyclophosphamide and rituximab with a minimal response.

Later, the patient received bendamustine as lymphodepleting chemotherapy 4 days prior to CART19 cell infusion. Prior to therapy, WBC was 14,200/µl, hemoglobin 11.4 gm/dl, platelet count 78,000/µl and ALC was 8000/µl. The CT scan showed diffuse adenopathy and bone marrow was extensively infiltrated with CLL (67% of cells). The patient received $1.6\times10^7$ CART-19 cells/kg ($1.13\times10^9$ total CART19 cells as assessed by FACS). There were no infusional toxicities. The patient became neutropenic approximately 10 days after bendamustine and 6 days after CART19 cell infusions, and beginning 10 days after the first CART19 infusion, the patient developed fevers, rigors and transient hypotension. At the same time, a chest X-ray and CT scan demonstrated a left upper lobe pneumonia treated with antibiotics. The fevers persisted for approximately 2 weeks and resolved when there was neutrophil recovery. The patient has had no further infectious or constitutional symptoms.

The patient achieved a rapid and complete response as depicted in FIG. 5. Between 1 and 6 months after infusion no circulating CLL cells have been detected in the blood by flow cytometry. Bone marrow at 1, 3 and 6 months after CART-19 cell infusions shows sustained absence of the lymphocytic infiltrate by morphology and flow cytometry testing. The CT scans at 1 and 3 months after infusion show complete resolution of abnormal adenopathy. The patient has had a persistent leukopenia (WBC 1000-3900/µl) and thrombocytopenia (platelets ~100,000/µl), and mild hypogammaglobulinia (IgG 525 mg/dL, normal 650-2000 mg/dL) but no infectious complications.

Patient UPN 02 was treated with CART19 cells at age 77. The patient had a relevant history of coronary artery disease and was first diagnosed with CLL in 2000 at age 68 when the patient presented with fatigue and leukocytosis. The patient was relatively stable for 4 years when the patient developed progressive leukocytosis (195,000411), anemia and thrombocytopenia requiring therapy. Genetic testing at that time showed that the CLL cells had deletion of chromosome 17p. Because of progressive disease, the patient was treated with a 12 week course of alemtuzumab with a partial response and improvement in blood counts. Within one and a half years the patient had progressive leukocytosis, anemia, thrombocytopenia, and splenomegaly. Karyotypic analysis confirmed deletion of chromosome 17p now with a deletion of chromosome 13q. The patient was retreated with alemtuzumab for 18 weeks with improvement of leukocytosis and stabilization of anemia and splenomegaly. The patient had evidence of progressive leukocytosis, anemia, and thrombocytopenia within one year. Treatment included 2 cycles of bendamustine with rituximab resulting in stable disease but no significant improvement as shown in FIG. 5A.

The patient received bendamustine alone as lymphodepleting chemotherapy prior to CART-19 cell infusion. The patient received $4.3 \times 10^6$ CART19 cells/kg ($4.1 \times 10^8$ total cells) in 3 split infusions complicated by transient fevers as high as 102° degrees for 24 hours. On day 11 after the first infusion, the patient received a boost of $4.1 \times 10^8$ ($4.3 \times 10^6$/kg) CART19 cells and this infusion was complicated by fevers, rigors and shortness of breath without hypoxia requiring a 24 hour hospitalization. There was no evidence for cardiac ischemia, and the symptoms resolved. On day 15 after the first CART-19 infusion and day 4 after the boost CART19 cell infusion the patient was admitted to the hospital with high fevers (up to 104° F.), chills and rigors. Extensive testing with blood and urine cultures and CXR failed to identify a source of infection. The patient complained of shortness of breath but had no hypoxia. An echocardiogram showed severe hypokinesis. Ejection fraction was 20%. The patient received prednisone 1 mg per kilogram for one day and 0.3 mg per kilogram for approximately one week. This resulted in rapid resolution of fevers and cardiac dysfunction.

Coincident with the onset of high fevers, the patient had a rapid drop in lymphocytes from peripheral blood as depicted in FIG. 5A. Although the patient had normalization of white blood count, the patient had persistent circulating CLL, stable moderate anemia and thrombocytopenia. Bone marrow showed persistent extensive infiltration of CLL one month after therapy despite dramatic peripheral blood cytoreduction, and CT scans showed a partial reduction of adenopathy and splenomegaly. Five months after CART19 cell infusions the patient developed progressive lymphocytosis. Nine months after infusions the patient has lymphocytosis (16,500/p1) with stable modest anemia and thrombocytopenia with stable adenopathy. The patient remains asymptomatic and has not had further therapy.

Patient UPN 03 was diagnosed with asymptomatic stage I CLL at age 50 and was followed with observation for 6 years. Later, the patient had progressive leukocytosis (white blood count 92,000/µl) and progressive adenopathy requiring therapy. The patient received 2 cycles of rituximab with fludarabine that resulted in normalization of blood counts and significant improvement though not complete resolution in adenopathy. The patient had approximately a 3 year progression free interval followed over the next 6 months by rapidly progressive leukocytosis (WBC 165,000/µl) and progressive adenopathy requiring therapy. The patient received one cycle of fludarabine and 3 cycles of rituximab with fludarabine with normalization of blood counts and resolution of palpable adenopathy. The patient had an approximate 20 month progression free interval until the patient again developed rapidly progressing leukocytosis and adenopathy. At this time, bone marrow was extensively infiltrated with CLL and karyotypic analysis showed cells to contain deletion of chromosome 17p with FISH demonstrating a TP53 deletion in $^{170}/_{200}$ cells. The patient received one cycle of rituximab with bendamustine followed by 4 cycles of bendamustine only (due to a severe allergic reaction to rituximab). The patient had initial normalization of blood counts but shortly after discontinuation of therapy had progressive leukocytosis and adenopathy.

Autologous T cells were collected by apheresis and cryopreserved from Patient UPN3. The patient was then treated with alemtuzumab for 11 weeks through with an excellent hematologic response. There was improvement though not complete resolution in adenopathy. The patient had active but stable disease over the next 6 months. Later, the patient received pentostatin and cyclophosphamide as lymphodepleting chemotherapy prior to CART19 cell infusion.

Three days after chemotherapy but prior to cell infusion, the bone marrow was hypercellular (60%) with approximately 40% involvement by CLL. Because of manufacturing limitations inherent in apheresis collections from CLL patients as depicted in Table 3 and (Bonyhadi et al., 2005, J Immunol 174:2366-2375), the patient was infused with a total of $1.46 \times 10^5$ CART19+ cells per kg ($1.42 \times 10^7$ total CART19+ cells) over 3 days. There were no infusional toxicities. Fourteen days after the first infusion, the patient began having chills, fevers as high as 102° F., rigors, nausea and diarrhea treated symptomatically. The patient had no respiratory or cardiac symptoms. By day 22 after infusion, a tumor lysis syndrome was diagnosed manifested by an elevated LDH, uric acid, and complicated by renal insufficiency. The patient was hospitalized and treated with fluid resuscitation and rasburicase with rapid normalization of uric acid and renal function. A detailed clinical evaluation with a CXR, blood, urine, and stool cultures were performed and were all negative or normal.

Within 1 month of CART-19 infusions, the patient had clearance of circulating CLL from the blood and bone marrow by morphology, flow cytometry, cytogenetic, and FISH analysis and CT scans showed resolution of abnormal adenopathy (FIG. 5C). The patient's remission has been sustained beyond 8 months from the initial CART19 cell infusion.

The results of the experiments are now described.
Clinical Protocol

Three patients with advanced, chemotherapy-resistant CLL were enrolled on a pilot clinical trial as depicted in FIG. 1. All patients were extensively pretreated with various chemotherapy and biologic regimens as shown in FIG. 10. Two of the patients had p53 deficient CLL, a deletion that portends poor response to conventional therapy and rapid progression (Dohner et al., 1995, Blood, 851580-1589). Each of the patients had large tumor burdens following the preparative chemotherapy, including extensive marrow infiltration (40 to 95%) and lymphadenopathy; patient UPN 02 also had significant peripheral lymphocytosis. The CART19 T cells were prepared as depicted in FIG. 1B and details of the cell manufacturing and product characterization for each patient are shown in Table 4. All patients were pretreated 1-4 days before CART19 T cell infusions with lymphodepleting chemotherapy. A split dose cell infusion schedule was used because the trial testing a CAR incorporating a 4-1BB costimulatory signaling domain as depicted in FIG. 1A.

TABLE 4

Apheresis products and CART19 product release criteria

| | Assay | Specification | UPN 01 | UPN 02 | UPN 03 |
|---|---|---|---|---|---|
| Apheresis Product | Flow Cytometry For CD3+ of CD45+ | N/A | 4.46% | 2.29% | 2.67% |
| CART19 Product | Total Cell Number Infused | ~2-5 × $10^9$ | 5 × $10^9$ | 1.275 × $10^9$<br>1.275 × $10^9$<br>[2.55 × $10^9$ total] | 3 × $10^6$ |
| | Cell Viability | >=70% | 96.2% | 95.3 (90.5)$^8$ | 90.3 |
| | % CD3+ Cells | >=80% | 88.9% | 98.8 | 98.9 |
| | Residual Bead # | <=100 beads/ 3 × $10^6$ Cells | 3.95 | 1 | 4 |
| | Endotoxin | <=3.5 EU/mL | <0.5 EU/mL | <0.5 EU/mL | <0.5 EU/mL |
| | Mycoplasma | Negative | Negative | Negative | Negative |
| | Sterility (Bactec) | No Growth | No Growth | No Growth | No Growth |
| | Fungal Culture | No Growth | No Growth | No Growth | No Growth |
| | BSA ELISA | <=1 µg/mL | <0.5 ng/mL | <0.5 ng/mL | <0.5 ng/mL |
| | Replication Competent Lentivirus (RCL) | RCL Not Detectable | Not Detectable | Inconclusive$^2$ | Inconclusive$^2$ |
| | Transduction Efficiency (scFv Expression) | >=20% | 22.6% | 23% | 4.74%$^4$ |
| | Vector DNA Sequence (CART19 PCR) | 0.2-3 copies/cell | 0.15$^3$ | 0.275 | 0.101 |

$^1$ = Dose #2.
$^2$ = Assay value at Day 12 below LOQ and had been decreasing from earlier in expansion consistent with carryover of plasmid DNA from vector generation.
Submitted to the FDA as an informational amendment.
$^3$ = Product release based on surface staining by FACS.
$^4$ = Treatment exception granted for release criteria by external DSMC and IRB.

In Vivo Expansion and Persistence of CART19 and Trafficking to Bone Marrow

Figure 2D:
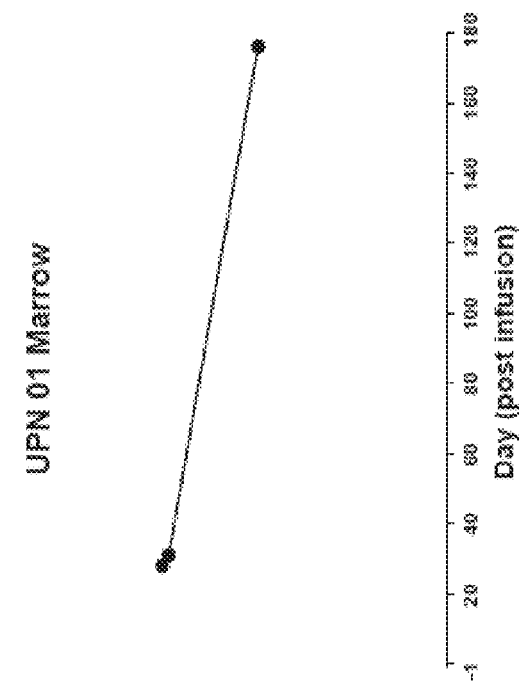
Figure 2C:
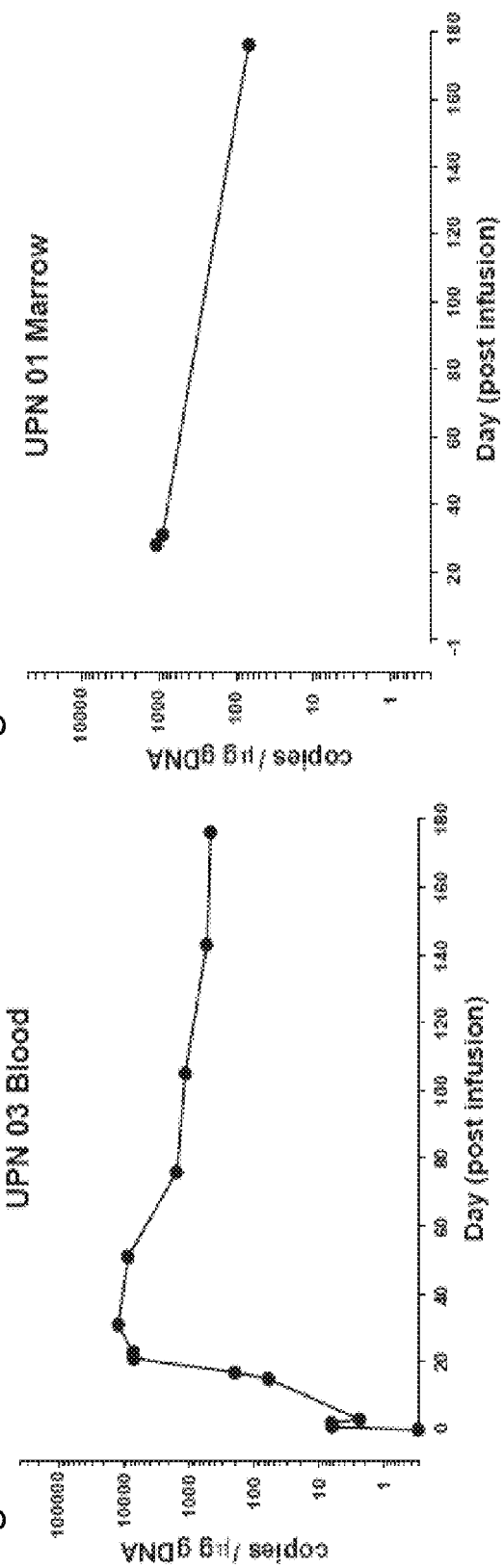
Figure 2E:
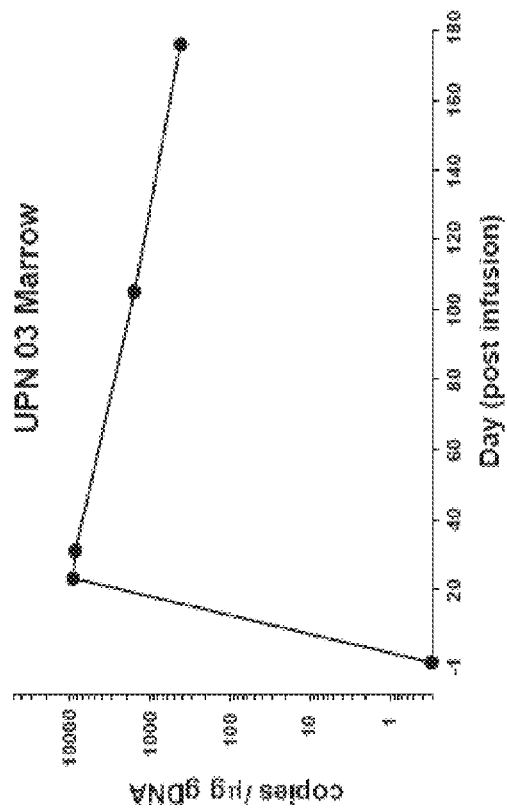
Figure 2F:
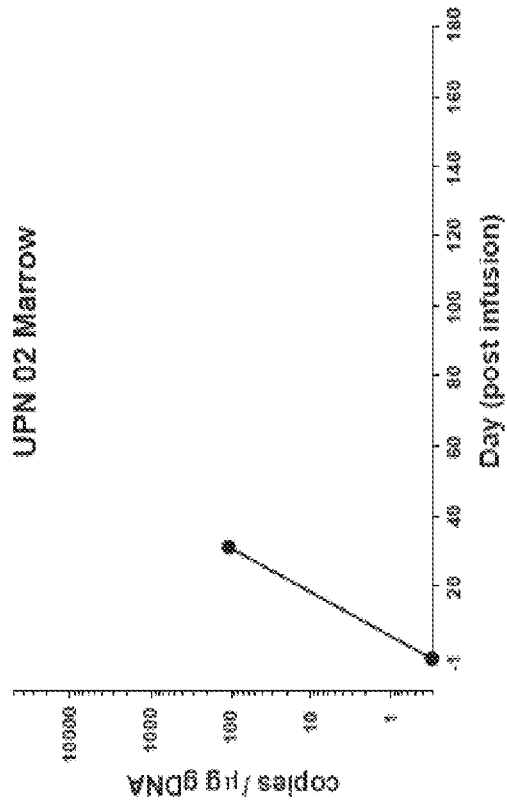

CAR+ T cells expanded using CD3/CD28 beads and expressing a 4-1BB signaling domain is believed to be in improvement to CARs lacking 4-1BB. A Q-PCR assay was developed to enable quantitative tracking of CART19 cells in blood and bone marrow. All patients had expansion and persistence of the CART19-cells in blood for at least 6 months as depicted in FIGS. 2A and 2C. Notably, patients UPN 01 and UPN 03 had a 1,000 to 10,000 fold expansion of CAR+ T cells in blood during the first month post infusion. The peak expansion levels coincided with onset of the post-infusion clinical symptoms in patient UPN 01 (day 15) and patient UPN 03 (day 23). Furthermore, following an initial decay that can be modeled with first order kinetics, the CART19 T cell levels stabilized in all 3 patients from day 90 to 180 post infusion. Significantly, the CART19 T cells also trafficked to bone marrow in all patients, albeit at 5- to 10-fold lower levels than observed in blood as depicted in FIGS. 2D through 2F. Patients UPN 01 and 03 had a log linear decay in the marrow, with a disappearance T½ of ~35 days.

Figure 3D:
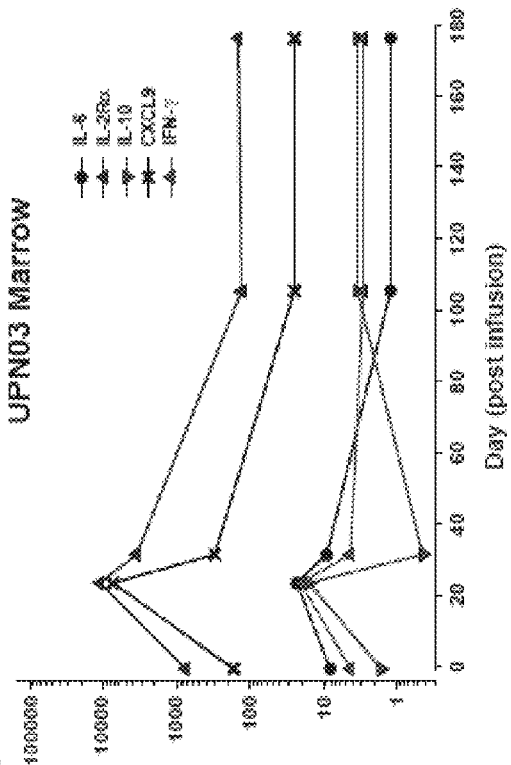
Figure 3C:
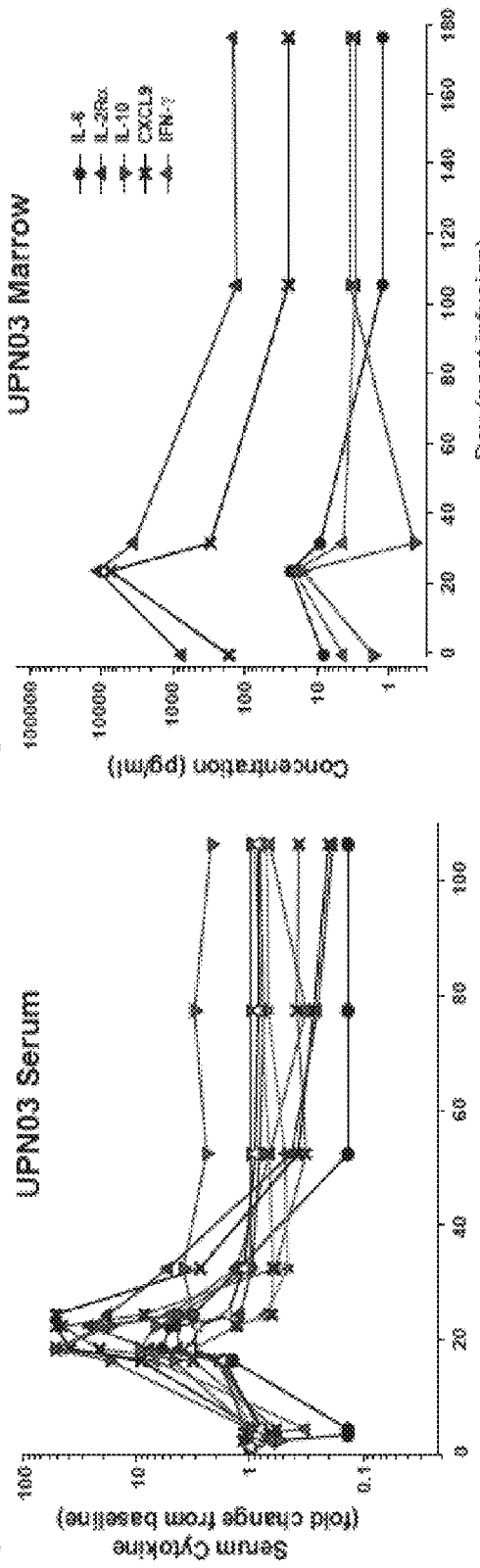

Induction of Specific Immune Responses in the Blood and Bone Marrow Compartments Following CART19 Infusion Serum samples from all patients were collected and batch analyzed to quantitatively determine cytokine levels, assessing a panel of cytokines, chemokines, and other soluble factors to assess potential toxicities and to provide evidence of CART19 cell function as depicted in FIG. 3. Of thirty analytes tested, eleven had a 3-fold or more change from baseline, including 4 cytokines (IL-6, INF-γ, IL-8 and IL-10), 5 chemokines (MIP-1α, MIP-1β, MCP-1, CXCL9, CXCL10) and soluble receptors for IL-1Rα and IL-2Rα. Of these, interferon-γ had the largest relative change from baseline. Interestingly, the peak time of cytokine elevation in UPN 01 and UPN 03 correlated temporally with the previously described clinical symptoms and the peak levels of CART19 cells in the blood in each patient. Only modest changes were noted in patient UPN 02, perhaps as a result of corticosteroid treatment given to this patient. Elevation of soluble IL-2 was not detected in the serum of the patients, even though one of the pre-clinical rationales for developing CAR+ T cells with 4-1BB signaling domains was the reduced propensity to trigger IL-2 secretion compared to CD28 signaling domains (Milone et al., 2009, Mol. Ther. 17:1453-1464). This may be relevant to sustained clinical activity as previous studies have shown that CAR+ T cells are potentially suppressed by regulatory T cells (Lee et al., 2011, Cancer Res 71:2871-2881), cells that could be elicited by CARs that secrete substantial amounts of IL-2 or by the provision of exogenous IL-2 post-infusion. Finally, a robust induction of cytokine secretion in the supernatants from bone marrow aspirates of UPN 03 was observed as depicted in FIG. 3D that also coincided with the development of tumor lysis syndrome and complete remission.

Prolonged Expression and Establishment of a Population of Memory CART19 Cells in Blood A central question in CAR-mediated cancer immunotherapy is whether optimized cell manufacturing and costimulation domains enhance the persistence of genetically modified T cells and permit the establishment of CAR+ memory T cells in patients. Previous studies have not demonstrated robust expansion, prolonged persistence and/or expression of CARs on T cells after infusion (Kershaw et al., 2006, Clin Cancer Res 12:6106-6115; Lamers et al., 2006, J Clin Oncol 24:e20-e22; Till et al., 2008, Blood, 112, 2261-2271; Savoldo et al., 2011, J Clin Invest doi:10.1172/JCI46110). Flow-cytometric analysis of samples from both blood and marrow at 169 days post infusion revealed the presence of CAR19 expressing cells in UPN 03 (FIGS. 4A and 4B), and an absence of B cells as depicted in FIG. 4A. Notably, by Q-PCR assay, all three patients have persisting CAR+ cells at 4 months and beyond as depicted in FIG. 2 and FIG. 6. The in vivo frequency of CAR+ cells by flow cytometry closely matched the values obtained from the PCR assay for the CART19 transgene. Importantly, in patient UPN 03, only CD3+ cells expressed the CAR19, as CAR19+ cells were not detectable in CD16- or CD14-positive subsets as depicted in FIG. 4A. CAR expression was also detected on the surface of 4.2% of T cells in the blood of patient UPN 01 on day 71 post infusion as depicted in FIG. 7.

Next, polychromatic flow cytometry was used to perform detailed studies to further characterize the expression, phenotype, and function of CART19 cells in UPN 03 using an anti-CAR idiotype antibody (MDA-647) and a gating strategy shown in FIG. 8. Notable differences in the expression of memory and activation markers in both CD8+ and CD4+ cells based on CAR19 expression was observed. At day 56, CART19 CD8+ cells displayed primarily an effector memory phenotype (CCR7–CD27–CD28–) consistent with prolonged and robust exposure to antigen as depicted in FIG. 4C. In contrast, CAR-negative CD8+ cells consisted of mixtures of effector and central memory cells, with CCR7 expression in a subset of cells, and substantial numbers in the CD27+/CD28– and CD27+/CD28+ fractions. While both CART19 and CAR-negative cell populations substantially expressed CD57, this molecule was uniformly co-expressed with PD-1 in the CART19 cells, a possible reflection of the extensive replicative history of these cells. In contrast to the CAR-negative cell population, the entirety of the CART19 CD8+ population lacked expression of both CD25 and CD127. By day 169, while the phenotype of the CAR-negative cell population remained similar to the day 56 sample, the CART19 population had evolved to contain a minority population with features of central memory cells, notably expression of CCR7, higher levels of CD27 and CD28, as well as CAR+ cells that were PD-1-negative, CD57-negative and CD127-positive.

In the CD4+ compartment, at day 56 CART19 cells were characterized by uniform lack of CCR7 and a predominance of CD27+/CD28+/PD-1+ cells distributed within both CD57+ and –compartments, and an essential absence of CD25 and CD127 expression as depicted in FIG. 4B. In contrast, CAR-negative cells at this time-point were heterogeneous in CCR7, CD27 and PD-1 expression, expressed CD127 and also contained a substantial CD25+/CD127-(potential regulatory T cell) population. By day 169, while CD28 expression remained uniformly positive in all CAR+CD4+ cells, a fraction of the CART19 CD4+ cells had evolved toward a central memory phenotype with expression of CCR7, a higher percentage of CD27-cells, the appearance of a PD-1-negative subset, and acquisition of CD127 expression. CAR-negative cells remained reasonably consistent with their day 56 counterparts, with the exception of a reduction in CD27 expression a decrease in the percentage of CD25+/CD127-cells.

CART19 Cells can Retain Effector Function after 6 Months in Blood

In addition to short persistence and inadequate in vivo proliferation, a limitation of previous trials with CAR+ T cells has been the rapid loss of functional activity of the infused T cells in vivo. The high level CART19 cell persistence and surface expression of the CAR19 molecule in patient UPN 01 and 03 provided the opportunity to directly test anti-CD19-specific effector functions in cells recovered from cryopreserved peripheral blood samples. PBMC from patient UPN 03 were cultured with target cells that were either positive or negative for CD19 expression (FIG. 4d). Robust CD19-specific effector function of CART19 T cells was demonstrated by specific degranulation against CD19-positive but not CD19-negative target cells, as assessed by surface CD107a expression. Notably, exposure of the CART19 population to CD19-positive targets induced a rapid internalization of surface CAR-19 as depicted in FIG. 8 for surface expression of CAR19 in the same effector cells in standard flow-cytometric staining. The presence of costimulatory molecules on target cells was not required for triggering CART19 cell degranulation because the NALM-6 line does not express CD80 or CD86 (Brentjens et al., 2007, Clin Cancer Res 13:5426-5435). Effector function was evident at day 56 post infusion and was retained at the day 169 time-point. Robust effector function of CAR+ and CAR-T cells could also be demonstrated by pharmacologic stimulation.

Clinical Activity of CART19 Cells

There were no significant toxicities observed during the four days following the infusion in any patient, other than transient febrile reactions. However, all patients subsequently developed significant clinical and laboratory toxicities between day 7 and 21 following the first infusion. These toxicities were short-term and reversible. Of the three patients treated to date, there are 2 CRs and 1 PR at >6 months post CART19 infusion according to standard criteria (Hallek et al., 2008, Blood 111:5446). Details of past medical history and response to therapy for each patient are depicted in FIG. 10.

In brief, patient UPN 01 developed a febrile syndrome, with rigors and transient hypotension beginning 10 days after infusion. The fevers persisted for approximately 2 weeks and resolved; the patient has had no further constitutional symptoms. The patient achieved a rapid and complete response as depicted in FIG. 5. Between 1 and 6 months after infusion, no circulating CLL cells have been detected in the blood by flow cytometry. Bone marrow at 1, 3, and 6 months after CART19 cell infusions shows sustained absence of the lymphocytic infiltrate by morphology and flow cytometric analysis as depicted in FIG. 5B. CT scans at 1 and 3 months after infusion show resolution of adenopathy as depicted in FIG. 5C. Complete remission was sustained for 10+ months at the time of this report.

Patient UPN 02 was treated with 2 cycles of bendamustine with rituximab resulting in stable disease as depicted in FIG. 5A. The patient received a third dose of bendamustine as lymphodepleting chemotherapy prior to CART19 T cell infusion. The patient developed fevers to 40° C., rigors and dyspnea requiring a 24 hour hospitalization on day 11 after the first infusion and on the day of the second CART19 cell boost. Fevers and constitutional symptoms persisted and on day 15, the patient had transient cardiac dysfunction; all symptoms resolved after corticosteroid therapy was initiated on day 18. Following CART19 infusion, and coincident with the onset of high fevers, the patient had rapid clearance of the p53-deficient CLL cells from peripheral blood as depicted in FIG. 5A and a partial reduction of adenopathy, bone marrow showed persistent extensive infiltration of CLL one month after therapy despite dramatic peripheral blood cytoreduction. The patient remains asymptomatic.

Patient UPN 03 received pentostatin and cyclophosphamide as lymphodepleting chemotherapy prior to CART19 cell infusion. Three days after chemotherapy but prior to cell infusion, bone marrow was hypercellular (60%) with approximately 50% involvement by CLL. The patient received a low dose of CART19 cells ($1.5 \times 10^5$ CAR+ T cells/kg divided over 3 days). Again, there were no acute infusional toxicities. However, 14 days after the first infusion, the patient began having rigors, fevers, nausea and diarrhea. By day 22 after infusion, tumor lysis syndrome was diagnosed requiring hospitalization. The patient had resolution of constitutional symptoms, and within 1 month of CART19 infusions, the patient had clearance of circulating CLL from the blood and bone marrow by morphology, flow cytometry, cytogenetic, and FISH analysis. CT scans showed resolution of abnormal adenopathy as depicted in FIGS. 5B and 5C. Complete remission was sustained beyond 8 months from the initial CART19 cell infusion.

Considerations of In Vivo CART19 Effector to CLL Target Cell Ratio

Pre-clinical studies showed that large tumors could be ablated, and that the infusion of $2.2 \times 10^7$ CARs could eradicate tumors comprised of $1 \times 10^9$ cells, for an in vivo E:T ratio of 1:42 in humanized mice (Carpenito et al., 2009, Proc Natl Acad Sci USA 106:3360-3365), although these calculations did not take into account the expansion of T cells after injection. Estimation of CLL tumor burden over time permitted the calculation of tumor reduction and the estimated CART19 E:T ratios achieved in vivo in the three subjects based on number of CAR+ T cells infused. Tumor burdens were calculated by measuring CLL load in bone marrow, blood and secondary lymphoid tissues. The baseline tumor burdens as shown in FIG. 10 indicate that each patient had on the order of $10^{12}$ CLL cells (i.e. 1 kilogram tumor load) before CART19 infusion. Patient UPN 03 had an estimated baseline tumor burden of $8.8 \times 10^{11}$ CLL cells in the bone marrow on day −1 (i.e. post chemotherapy and pre-CART19 infusion), and a measured tumor mass in secondary lymphoid tissues of 3.3–$5.5 \times 10^{11}$ CLL cells, depending on the method of volumetric CT scan analysis. Given that UPN 03 was infused with only $1.4 \times 10^7$ CART19 cells, using the estimate of initial total tumor burden ($1.3 \times 10^{12}$ CLL cells), and that no CLL cells are detectable post treatment, a striking 1:93,000 E:T ratio was achieved. By similar calculations, an effective E:T ratio in vivo of 1:2200 and 1:1000 was calculated for UPN 01 and UPN 02 as shown in Table 3). In the end, a contribution of serial killing by CART19 T cells, combined with in vivo CART19 expansion of >1.000-fold likely contributed to the powerful anti-leukemic effects mediated by CART19 cells.

T Cells Expressing Chimeric Receptors Establish Memory and Potent Antitumor Effects in Patients with Advanced Leukemia Limited in vivo expression and effector function of CARs has been a central limitation in the trials testing first generation CARs (Kershaw et al., 2006, Clin Cancer Res 12:6106-6115; Lamers et al., 2006, J Clin Oncol 24:e20-e22; Till et al., 2008, Blood, 112, 2261-2271; Park et al., 2007, Mol Ther 15:825833; Pule et al., 2008, Nat Med 14:1264-1270). Based on pre-clinical modeling demonstrating enhanced persistence of CARs containing a 4-1BB signaling module (Milone et al., 2009, Mol. Ther. 17:1453-1464; Carpenito et al., 2009, Proc Natl Acad Sci USA 106:3360-3365), experiments were designed to develop a second generation of CARs engineered with lentiviral vector technology. This second generation of CARs was found to be safe in the setting of chronic HIV infection (Levine et al., 2006, Proc Natl Acad Sci USA 103: 17372-17377). The present results show that when this second generation CAR was expressed in T cells and cultured under conditions designed to promote engraftment of central memory T cells (Rapoport et al., 2005, Nat Med 11:1230-1237; Bondanza et al., 2006, Blood 107:1828-1836), improved expansion of CART cells after infusion was observed compared to previous reports. CART19 cells established CD19-specific cellular memory, and killed tumor cells at E:T ratios in vivo not previously achieved.

CART19 is the first CAR trial to incorporate a 4-1BB signaling domain and the first to use lentiviral vector technology. The present results demonstrate efficient tracking of CARs to sites of tumor, with the de facto establishment of "tumor infiltrating lymphocytes" that exhibited CD19 specificity. The pronounced in vivo expansion permitted the first demonstration that CARs directly recovered from patients can retain effector function in vivo for months. A previous study had suggested that introduction of a first generation CAR into virus specific T cells is preferable to primary T cells (Pule et al., 2008, Nat Med 14:1264-1270), however the results with second generation CARs introduced into optimally costimulated primary T cells calls this notion into question. Without wishing to be bound by any particular theory, a cautionary note is raised that the clinical effects were profound and unprecedented with the lysis of kilogram sized tumor burdens in all three patients accompanied with the delayed release of potentially dangerously high levels of cytokines in two of the patients. Classical cytokine storm effects were not observed. However, the present study was designed to mitigate this possibility by deliberate infusion of CART19 over a period of three days.

It was found that very low doses of CARs can elicit potent clinical responses. This was a pilot study that demonstrated safety of the CART19 vector design. The observation that doses of CART19 cells several orders of magnitude below those tested in previous trials can have clinical benefit may have important implications for future implementation of CAR therapy on a wider scale, and for the design of trials testing CARs directed against targets other than CD19.

The present studies further indicate that CART19 is expressed in both central memory and effector T cells, and this likely contributes to their long term survival compared to previous reports. Without wishing to be bound by any particular theory, CAR T cells may differentiate in vivo into a central memory-like state upon encounter and subsequent elimination of target cells (e.g. CLL tumor cells or normal B cells) expressing the surrogate antigen. Indeed signaling of 4-1BB has been reported to promote the development of memory in the context of TCR signaling (Sabbagh et al., 2007, Trends Immunol 28:333-339).

The extended proliferation and survival of CART19 has revealed aspects of the pharmacokinetics of CAR T cells that have not previously been reported. It was observed that the kinetics of cytokine release in serum and marrow correlated with peak CART19 levels, so that it is possible that the decay is initiated when cellular targets expressing CD19 become limiting. The mechanism of the extended survival of CART19 may relate to the aforementioned incorporation of the 4-1BB domain or to signaling through the natural TCR and/or CAR. An intriguing possibility is that the extended survival is related to the population of CART19 that has been identified in marrow specimens, raising the hypothesis that CD19 CARs could be maintained by encounter with B cell progenitors in the bone marrow. Related to this question is what drives the initial expansion of CART19 cells in vivo? With rare exceptions (Savoldo et al., 2011, J Clin Invest doi: 10.1172/JCI46110; Pule et al., 2008, Nat Med 14:1264-1270), the present study is the only trial to have omitted IL-2 infusions, so that the CART19 cells likely either expanded in response to homeostatic cytokines or more likely, to CD19 expressed on leukemic targets and/or normal B cells. In the latter case, this could be an attractive feature for CARs directed against targets on normal APCs such as CD19 and CD20, as it is possible that self renewal of CART19 occurs on the normal cells, providing a mechanism for CAR memory by means of "self vaccination/boosting" and therefore, long term tumor immunosurveillance. The mechanisms of CART19 homeostasis may require further study to elucidate cell intrinsic and extrinsic mechanisms of persistence. Previous to these results, most investigators have viewed CAR therapy as a transient form of immunotherapy, however CARs with optimized signaling domains may have a role in both remission induction and consolidation as well as for long term immunosurveillance.

Potent anti-leukemic effects have been observed in all three patients, including two patients with p53 deficient leukemia. Previous studies with CARs have had difficulty separating antitumor effects from lymphodepleting chemotherapy. However, the delayed cytokine release combined with the kinetics of tumor lysis in fludarabine-refractory patients that was coincident, and possibly dependent on in vivo CAR expansion in the present study, indicate that CART19 mediates potent antitumor effects. The present results do not exclude a role for chemotherapy in potentiating the effects of CARs.

A thorough comparison of the vector, transgene and cell manufacturing procedures with results from ongoing studies at other centers may be required to gain a full understanding of the key features required to obtain sustained function of CAR T cells in vivo. Unlike antibody therapies, CAR-modified T cells have the potential to replicate in vivo, and long-term persistence could lead to sustained tumor control. The availability of an off the shelf therapy comprised of non-cross resistant killer T cells has the potential to improve the outcome of patients with B cell malignancies. A limitation of antibody therapy, as for example, with agents such as rituximab and bevicizumab, is that the therapy requires repeated antibody infusions, that is inconvenient and costly. The delivery of prolonged antibody therapy (in this case for at least 6 months in 3 of 3 patients treated to date) with anti-CD19 scFv expressed on T cells following a single infusion of CART19 cells has a number of practical advantages, including conveniences and cost savings.

Example 2

Chimeric Antigen Receptor-Modified T Cells in Chronic Lymphoid Leukemia

A lentiviral vector expressing a chimeric antigen receptor with specificity for the B-cell antigen CD19, coupled with CD137 (a costimulatory receptor in T cells [4-1BB]) and CD3-zeta (a signal-transduction component of the T-cell antigen receptor) signaling domains, was designed. It was observed that a low dose (approximately $1.5 \times 10^5$ cells per kilogram of body weight) of autologous chimeric antigen receptor-modified T cells reinfused into a patient with refractory chronic lymphocytic leukemia (CLL) expanded to a level that was more than 1000 times as high as the initial engraftment level in vivo. It was also observed that the patient exhibited delayed development of the tumor lysis syndrome and with complete remission.

Apart from the tumor lysis syndrome, the only other grade ¾ toxic effect related to chimeric antigen receptor T cells was lymphopenia. Engineered cells persisted at high levels for at least 6 months in the blood and bone marrow and continued to express the chimeric antigen receptor. A specific immune response was detected in the bone marrow, accompanied by loss of normal B cells and leukemia cells that express CD19. Remission was ongoing 10 months after treatment. Hypogammaglobulinemia was an expected chronic toxic effect.

The materials and methods employed in these experiments are now described.

Materials and Methods

Study Procedures

A self-inactivating lentiviral vector (GeMCRIS 0607-793) was designed, which was subjected to preclinical safety testing, as reported previously (Milone et al., 2009, Mol Ther, 17: 1453-64). Methods of T-cell preparation have also been described previously (Porter et al, 2006, Blood, 107:1325-31). Quantitative polymerase-chain-reaction (PCR) analysis was performed to detect chimeric antigen receptor T cells in blood and bone marrow. The lower limit of quantification was determined from the standard curve; average values below the lower limit of quantification (i.e., reportable but not quantifiable) are considered approximate. The lower limit of quantification of the assay was 25 copies per microgram of genomic DNA.

Soluble-factor analysis was performed with the use of serum from whole blood and bone marrow that was separated into aliquots for single use and stored at $-80°$ C. Quantification of soluble cytokine factors was performed with the use of Luminex bead-array technology and reagents (Life Technologies).

Apheresis #1

A 12-15 liter apheresis procedure is carried out at the apheresis center. Peripheral blood mononuclear cells (PBMC) are obtained for CART-19 T cell generation during this procedure. From a single leukapheresis, at least $50 \times 10^9$ white blood cells are harvested to manufacture CART-19 T cells. Baseline blood leukocytes are also obtained and cryopreserved.

Cytoreductive Chemotherapy

Chemotherapy is started approximately 5-10 days before infusion so that CART-19 cells may be given 1-2 days after completion of the chemotherapy. The timing of chemotherapy initiation therefore depends on the length of the regimen. The purpose of the chemotherapy is to induce lymphopenia in order to facilitate engraftment and homeostatic expansion of CART-19 cells. The chemotherapy may be chosen also to reduce disease tumor burden. The cytoreductive chemotherapy is chosen and administered by community oncologists. The choice of chemotherapy depends on the patients underlying disease and prior therapies. Fludarabine (30 mg/m2/day×3 days) and cyclophosphamide (300 mg/m2/day×3 days) are the agents of choice, as there is the most experience with the use of these agents in facilitating adoptive immunotherapy. Several other acceptable regimens using FDA-approved drugs are appropriate, including CHOP, HyperCVAD, EPOCH, DHAP, ICE or other regimens.

Restaging Assessment

A limited restaging is performed at the completion of chemotherapy in order to provide baseline tumor burden measurements. This includes imaging, physical examination, and minimal residual disease (MRD) assessments. Subjects undergo the following for pre-infusing testing: physical exam, documentation of adverse events and blood draws for hematology, chemistry and pregnancy testing (if applicable).

Preparation of CART-19 T Cells

Autologous T cells are engineered to express an extracellular single chain antibody (scFv) with specificity for CD19. The extracellular scFv can redirect specificity of the transduced T cells for cells that express CD19, a molecule that is restricted in expression on the surface of the malignant cells and on normal B cells. In addition to CD19 scFv, the cells are transduced to express an intracellular signaling molecule comprised of either the TCR4 chain or a tandem signaling domain comprised of 4-1BB and TCR4 signaling modules. The scFv is derived from a mouse monoclonal antibody, and thus contains mouse sequences, and the signaling domains are entirely of the native human sequences. CART-19 T cells are manufactured by isolating the T cells by apheresis, and using lentiviral vector technology (Dropulic et al., 2006, Human Gene Therapy, 17: 577-88; Naldini et al., 1996, Science, 272: 263-7; Dull et al., 1998, J Virol, 72: 8463-71) to introduce the scFv:TCRζ4:4-1BB into CD4 and CD8 T cells. In some patients, a control scFv:TCR4: is introduced into a portion of the cells for a competitive repopulation experiment. These receptors are "universal" in that they bind antigen in an MHC-independent fashion, thus, one receptor construct can be used to treat a population of patients with CD19 antigen-positive tumors.

Figure 11:
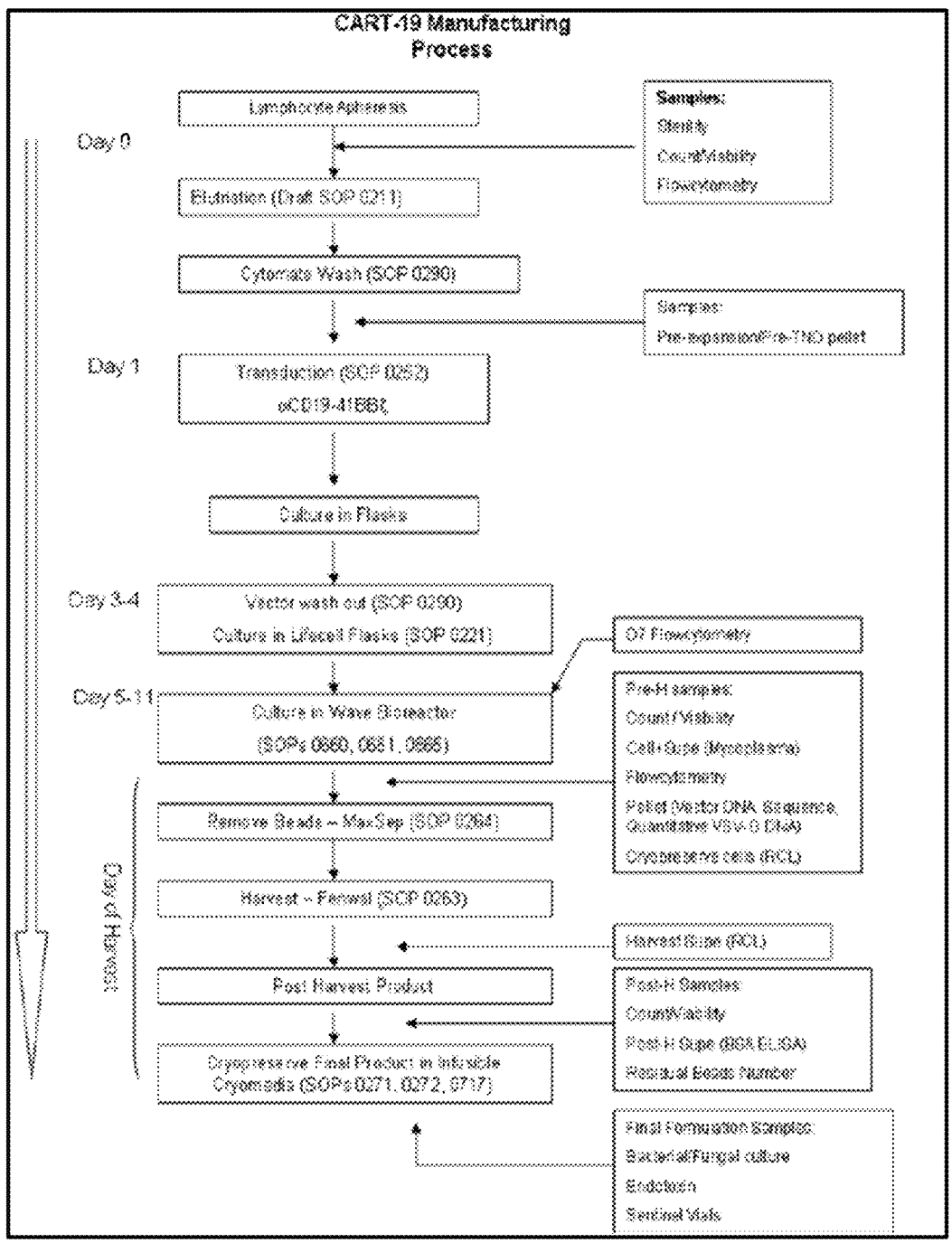
FIG. 11 depicts the manufacturing process of CART-19 cells.

The CAR constructs were developed at the University of Pennsylvania, and the clinical grade vector was manufactured at Lentigen Corporation. The CART-19 cells are manufactured in the Clinical Cell and Vaccine Production Facility at the University of Pennsylvania according to the process shown in FIG. 11. At the end of cell cultures, the cells are cryopreserved in infusible cryomedia. A single dose of CART-19 transduced T cells comprising of the infusion of $2.5 \times 10^9$ to $5 \times 10^9$ total cells, are administered in either 1 or 2 bags. Each bag contains an aliquot (volume dependent upon dose) of cryomedia containing the following infusible grade reagents (% v/v): 31.25 plasmalyte-A, 31.25 dextrose (5%), 0.45 NaCl, up to 7.50 DMSO, 1.00 dextran 40, 5.00 human serum albumin with approximately $2.5-5 \times 10^9$ autologous T cells per bag. For increased safety, the first dose is given as a split dose on days 0, 1 and 2, with ~10% of the cells on day 0, 30% on day 1, and 60% on day 2.

Storage

Bags (10 to 100 ml capacity) containing CART-19-transduced T cells are stored in blood bank conditions in a monitored −135° C. freezer. Infusion bags are stored in the freezer until needed.

Cell Thawing

After logging the cells in the investigational pharmacy, frozen cells are transported in dry ice to the subject's bedside. The cells are thawed at the bedside one bag at a time using a water bath maintained at 36° C. to 38° C. The bag is gently massaged until the cells have just thawed. There should be no frozen clumps left in the container. If the CART-19 cell product appears to have a damaged or leaking bag, or otherwise appears to be compromised, it should not be infused.

Premedication

Side effects following T cell infusions may include transient fever, chills, and/or nausea. It is recommended that the subject be pre-medicated with acetaminophen 650 mg by mouth and diphenhydramine hydrochloride 25-50 mg by mouth or IV, prior to the infusion of CART-19 cells. These medications may be repeated every six hours as needed. A course of non-steroidal anti-inflammatory medication may be prescribed if the patient continues to have fever not relieved by acetaminophen. It is recommended that patients not receive systemic corticosteroids such as hydrocortisone, prednisone, prednisolone (Solu-Medrol) or dexamethasone (Decadron) at any time, except in the case of a life-threatening emergency, since this may have an adverse effect on T cells. If corticosteroids are required for an acute infusional reaction, an initial dose of hydrocortisone 100 mg is recommended.

Administration/Infusion

Infusions begin 1 to 2 days after completion of chemotherapy. The day of the first infusions, patients have a CBC with differential, and assessment of CD3, CD4 and CD8 counts since chemotherapy is given in part to induce lymphopenia. Without wishing to be bound by any particular theory, it is believed that an initial i.v. dose of $2.5-5 \times 10^9$ CART-19 cells is optimal for this protocol. Because there are about $1 \times 10^{12}$ T cells in a healthy adult, the proposed total dose is equivalent to about 0.5% of the total body mass of T cells (Roederer, 1995, Nat Med, 1: 621-7; Macallan et al., 2003, Eur J Immunol, 33: 2316-26). The first dose is administered using a split dose on days 0 (10%), 1 (30%) and 2 (60%). Subjects receive infusion in an isolated room. The cells are thawed at the patient's bedside as described elsewhere herein. The thawed cells are given at an infusion rate as quickly as tolerated so that the duration of the infusion is approximately 10-15 minutes. The transduced T cells are administered by rapid intravenous infusion at a flow rate of approximately 10 mL to 20 mL per minute through an 18-gauge latex free Y-type blood set with a 3-way stopcock. The duration of the infusion is approximately 15 minutes. One or two bags of CART-19 modified cells are delivered on ice, and the cells are administered to the subject while cold. In subjects receiving mixtures of CART-19 cells, in order to facilitate mixing, the cells are administered simultaneously using a Y-adapter. Subjects are infused and premedicated as described elsewhere herein. Subjects' vital signs are assessed and pulse oximetry is done prior to dosing, at the end of the infusion and every 15 minutes thereafter for 1 hour and until these are stable and satisfactory. A blood sample for determination of baseline CART-19 level is obtained before infusion and 20 minutes post infusion. Patients experiencing toxicities from their preceding cytoreductive chemotherapy have their infusion schedule delayed until these toxicities have resolved. The specific toxicities warranting delay of T cell infusions include: 1) Pulmonary: Requirement for supplemental oxygen to keep saturation greater than 95% or presence of radiographic abnormalities on chest x-ray that are progressive; 2) Cardiac: New cardiac arrhythmia not controlled with medical management. 3) Hypotension requiring pressor support. 4) Active Infection: Positive blood cultures for bacteria, fungus, or virus within 48-hours of T cell infusion. A serum sample for potassium and uric acid is collected before the first infusion as well as two hours after each subsequent infusion.

Post Infusion Laboratories to Assess Graftment and Persistence

Subjects return at day 4 and 10 after the initial CART-19 cell infusion to have blood drawn for serum cytokine levels, and CART-19 PCR in order to evaluate the presence of CART-19 cells. Subjects return once a week for three weeks to undergo the following: physical exam, documentation of adverse events and blood draws for hematology, chemistry, engraftment and persistence of CART-19 cells and research labs.

Second Infusion

Without wishing to be bound by any particular theory, it is believed that a second dose of CART-19 cells can be given on day 11 to patients, provided that they exhibit adequate tolerance to the first dose and sufficient CART-19 cells were manufactured. The dose is $2-5 \times 10^9$ total cells. A serum sample for potassium and uric acid can be collected two hours after the infusion.

Second Apheresis

A 2 liter apheresis procedure is carried out at the apheresis center. PBMC are obtained for research and cryopreserved. Subjects undergo the following: physical exam, documentation of adverse events and blood draws for hematology, chemistry, engraftment and persistence of CART-19 cells and research labs. In addition restaging is done in order to provide tumor burden measurements. Restaging testing is determined by disease type and includes imaging, MRD assessments, bone marrow aspirate and biopsy and/or lymph node biopsy.

Monthly Evaluations 2 to 6 Months Post Infusion

Subjects return on a monthly basis during months 2 to 6 post CART-19 cell infusion. At these study visits, subjects undergo the following: concomitant medication, physical exam, documentation of adverse events and blood draws for hematology, chemistry, engraftment and persistence of CART-19 cells and research labs. The HIV DNA assay is performed at months 2-6 post CART-19 cell infusion to exclude the presence of detectable RCL.

Quarterly Evaluations Up to 2 Years Post Infusion

Subjects are evaluated on a quarterly basis until 2 years post infusion. At these study visits, subjects undergo the following: concomitant medication, physical exam, documentation of adverse events and blood draws for hematology, chemistry, engraftment and persistence of CART-19 cells and research labs. The HIV DNA assay is performed at months 3 and 6 post CART-19 cell infusion to exclude the presence of detectable RCL.

The results of the experiments are now described

Patient History

The patient received a diagnosis of stage I CLL in 1996. He first required treatment after 6 years of observation for progressive leukocytosis and adenopathy. In 2002, he was treated with two cycles of rituximab plus fludarabine; this treatment resulted in normalization of blood counts and partial resolution of adenopathy. In 2006, he received four cycles of rituximab and fludarabine for disease progression, again with normalization of blood counts and partial regression of adenopathy. This response was followed by a 20-month progression-free interval and a 2-year treatment-free interval. In February 2009, he had rapidly progressive leukocytosis and recurrent adenopathy. His bone marrow was extensively infiltrated with CLL. Cytogenetic analysis showed that 3 of 15 cells contained a deletion of chromosome 17p, and fluorescence in situ hybridization (FISH) testing showed that 170 of 200 cells had a deletion involving TP53 on chromosome 17p. He received rituximab with bendamustine for one cycle and three additional cycles of bendamustine without rituximab (because of a severe allergic reaction). This treatment resulted in only transient improvement in lymphocytosis. Progressive adenopathy was documented by means of computed tomography (CT) after therapy.

Autologous T cells were collected by means of leukapheresis and cryopreserved. The patient then received alemtuzumab (an anti-CD52, mature-lymphocyte, cell-surface antigen) for 11 weeks, with improved hematopoiesis and a partial resolution of adenopathy. Over the next 6 months, he had stable disease with persistent, extensive marrow involvement and diffuse adenopathy with multiple 1- to 3-cm lymph nodes. In July 2010, the patient was enrolled in a phase 1 clinical trial of chimeric antigen receptor-modified T cells.

Cell Infusions

Autologous T cells from the patient were thawed and transduced with lentivirus to express the CD19-specific chimeric antigen receptor (FIG. 12A); sequence identifiers for the lentiviral vector and relevant sequences are depicted in Table 5. Four days before cell infusion, the patient received chemotherapy designed for depletion of lymphocytes (pentostatin at a dose of 4 mg per square meter of body-surface area and cyclophosphamide at a dose of 600 mg per square meter) without rituximab (Lamanna et al., 2006, J Clin Oncol, 24: 1575-81). Three days after chemotherapy but before cell infusion, the bone marrow was hypercellular with approximately 40% involvement by CLL. Leukemia cells expressed kappa light chain and CD5, CD19, CD20, and CD23. Cytogenetic analysis showed two separate clones, both resulting in loss of chromosome 17p and the TP53 locus (46,XY,del(17)(p12)[5]/46,XY,der(17)417;21)(q10;q10)[5]/46,XY[14]). Four days after chemotherapy, the patient received a total of $3 \times 10^8$ T cells, of which 5% were transduced, for a total of $1.42 \times 10^7$ transduced cells ($1.46 \times 10^5$ cells per kilogram) split into three consecutive daily intravenous infusions (10% on day 1, 30% on day 2, and 60% on day 3). No postinfusion cytokines were administered. No toxic effects of infusions were noted.

TABLE 5

Sequence identifiers for pELPS-CD19-BBz transfer vector

| SEQ ID NO: # | IDENTITY |
|---|---|
| SEQ ID NO: 1 | pELPS-CD19-BBZ transfer vector (nucleic acid sequence) |
| SEQ ID NO: 2 | RSV's U3 (nucleic acid sequence) |
| SEQ ID NO: 3 | HIV R repeat (nucleic acid sequence) |
| SEQ ID NO: 4 | HIV U5 Repeat (nucleic acid sequence) |
| SEQ ID NO: 5 | Partial Gag/Pol (nucleic acid sequence) |
| SEQ ID NO: 6 | cPPT (nucleic acid sequence) |
| SEQ ID NO: 7 | EF1 alpha Promoter (nucleic acid sequence) |
| SEQ ID NO: 8 | CD19-BBzeta CAR (nucleic acid sequence) |
| SEQ ID NO: 9 | Hu Woodchuck PRE (nucleic acid sequence) |
| SEQ ID NO: 10 | R Repeat (nucleic acid sequence)t |
| SEQ ID NO: 11 | U5 Repeat (nucleic acid sequence) |
| SEQ ID NO: 12 | CD19-BBzeta CAR (amino acid sequence) |
| SEQ ID NO: 13 | CD8 Leader (nucleic acid sequence) |
| SEQ ID NO: 14 | Anti-CD19scFv (nucleic acid sequence) |
| SEQ ID NO: 15 | CD8 Hinge (nucleic acid sequence) |
| SEQ ID NO: 16 | CD8 Transmembrane (nucleic acid sequence) |
| SEQ ID NO: 17 | 4-1BB (nucleic acid sequence) |
| SEQ ID NO: 18 | CD3zeta (nucleic acid sequence) |
| SEQ ID NO: 19 | CD8 Leader (amino acid sequence) |
| SEQ ID NO: 20 | Anti-CD19scFv (amino acid sequence) |
| SEQ ID NO: 21 | CD8 Hinge (amino acid sequence) |
| SEQ ID NO: 22 | CD8 Transmembrane (amino acid sequence) |
| SEQ ID NO: 23 | 4-1BB (amino acid sequence) |
| SEQ ID NO: 24 | CD3zeta (amino acid sequence) |

Clinical Response and Evaluations

Figure 12B:
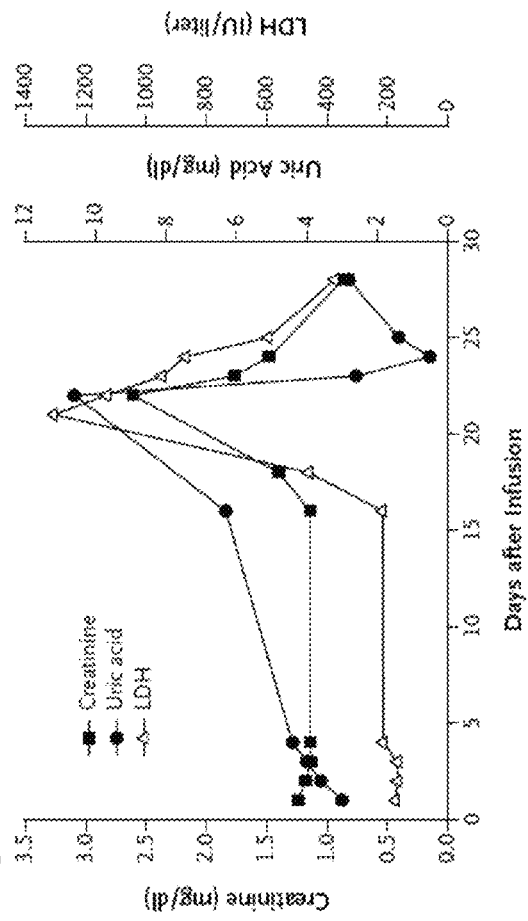
Figure 12A:
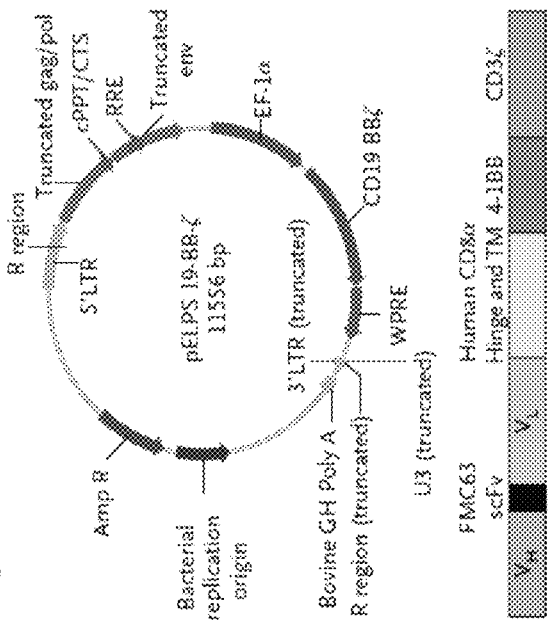

Fourteen days after the first infusion, the patient began having chills and low-grade fevers associated with grade 2 fatigue. Over the next 5 days, the chills intensified, and his temperature escalated to 39.2° C. (102.5° F.), associated with rigors, diaphoresis, anorexia, nausea, and diarrhea. He had no respiratory or cardiac symptoms. Because of the fevers, chest radiography and blood, urine, and stool cultures were performed, and were all negative or normal. The tumor lysis syndrome was diagnosed on day 22 after infusion (FIG. 12B). The uric acid level was 10.6 mg per deciliter (630.5 µmol per liter), the phosphorus level was 4.7 mg per deciliter (1.5 mmol per liter) (normal range, 2.4 to 4.7 mg per deciliter [0.8 to 1.5 mmol per liter]), and the lactate dehydrogenase level was 1130 Upper liter (normal range, 98 to 192). There was evidence of acute kidney injury, with a creatinine level of 2.60 mg per deciliter (229.8 µmol per liter) (baseline level, <1.0 mg per deciliter [<88.4 µmol per liter]). The patient was hospitalized and treated with fluid resuscitation and rasburicase. The uric acid level returned to the normal range within 24 hours, and the creatinine level within 3 days; he was discharged on hospital day 4. The lactate dehydrogenase level decreased gradually, becoming normal over the following month.

By day 28 after CART19-cell infusion, adenopathy was no longer palpable, and on day 23, there was no evidence of CLL in the bone marrow (FIG. 12C). The karyotype was now normal in 15 of 15 cells (46,XY), and FISH testing was negative for deletion TP53 in 198 of 200 cells examined; this is considered to be within normal limits in negative controls. Flow-cytometric analysis showed no residual CLL, and B cells were not detectable (<1% of cells within the CD5+ CD10−CD19+ CD23+ lymphocyte gate). CT scanning performed on day 31 after infusion showed resolution of adenopathy (FIG. 12D).

Three and 6 months after CART19-cell infusion, the physical examination remained unremarkable, with no palpable adenopathy, and CT scanning performed 3 months after CART19-cell infusion showed sustained remission (FIG. 12D). Bone marrow studies at 3 and 6 months also showed no evidence of CLL by means of morphologic analysis, karyotype analysis (46,XY), or flow-cytometric analysis, with a continued lack of normal B cells as well. Remission had been sustained for at least 10 months.

Toxicity of CART19 Cells

The cell infusions had no acute toxic effects. The only serious (grade 3 or 4) adverse event noted was the grade 3 tumor lysis syndrome described above. The patient had grade 1 lymphopenia at baseline and grade 2 or 3 lymphopenia beginning on day 1 and continuing through at least 10 months after therapy. Grade 4 lymphopenia, with an absolute lymphocyte count of 140 cells per cubic millimeter, was recorded on day 19, but from day 22 through at least 10 months, the absolute lymphocyte count ranged between 390 and 780 cells per cubic millimeter (grade 2 or 3 lymphopenia). The patient had transient grade 1 thrombocytopenia (platelet count, 98,000 to 131,000 per cubic millimeter) from day 19 through day 26 and grade 1 or 2 neutropenia (absolute neutrophil count, 1090 to 1630 per cubic millimeter) from day 17 through day 33. Other signs and symptoms that were probably related to the study treatment included grade 1 and 2 elevations in aminotransferase and alkaline phosphatase levels, which developed 17 days after the first infusion and resolved by day 33. Grade 1 and 2 constitutional symptoms consisted of fevers, chills, diaphoresis, myalgias, headache, and fatigue. Grade 2 hypogammaglobulinemia was corrected with infusions of intravenous immune globulin.

Analysis of Serum and Bone Marrow Cytokines

The patient's clinical response was accompanied by a delayed increase in levels of inflammatory cytokines (FIG. 13A through FIG. 13D), with levels of interferon-γ, the interferon-γ-responsive chemokines CXCL9 and CXCL10, and interleukin-6 that were 160 times as high as baseline levels. The temporal rise in cytokine levels paralleled the clinical symptoms, peaking 17 to 23 days after the first CART19-cell infusion.

Figure 13E:
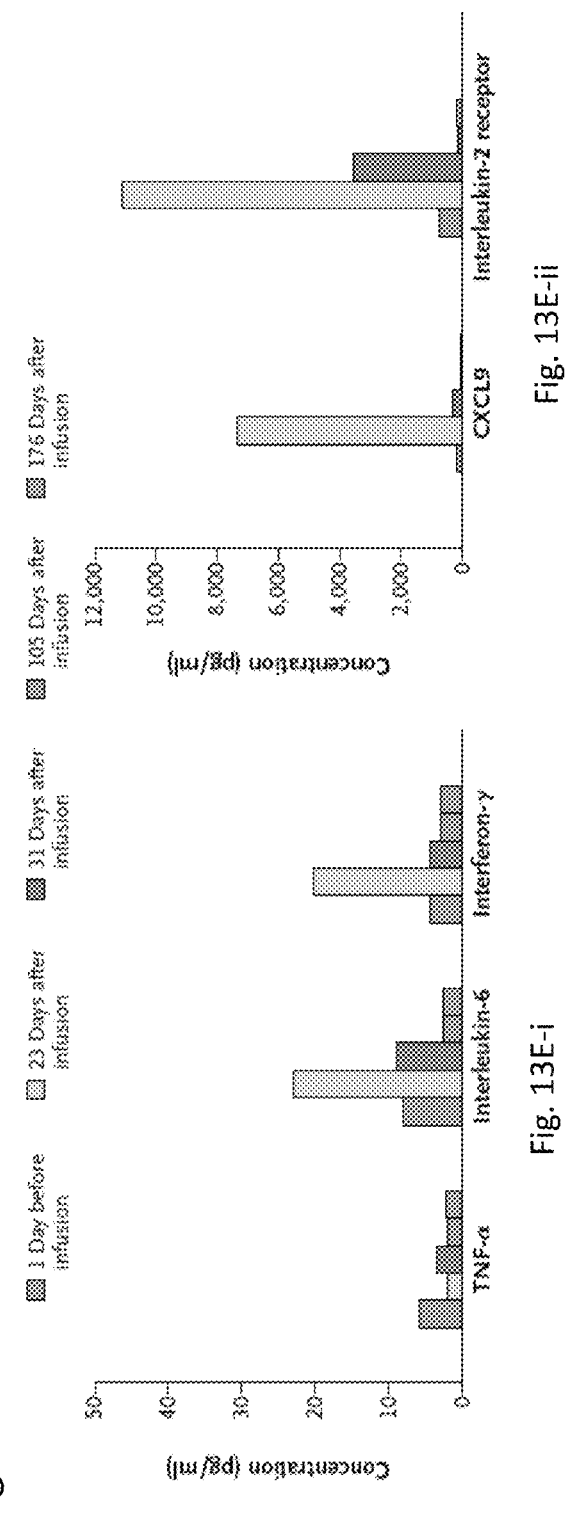

The supernatants from serial bone marrow aspirates were measured for cytokines and showed evidence of immune activation (FIG. 13E). Significant increases in interferon-γ, CXCL9, interleukin-6, and soluble interleukin-2 receptor were noted, as compared with the baseline levels on the day before T-cell infusion; the values peaked on day 23 after the first CART19-cell infusion. The increase in bone marrow cytokines coincided with the elimination of leukemia cells from the marrow. Serum and marrow tumor necrosis factor α remained unchanged.

Expansion and Persistence of Chimeric Antigen Receptor T Cells

Figure 14B:
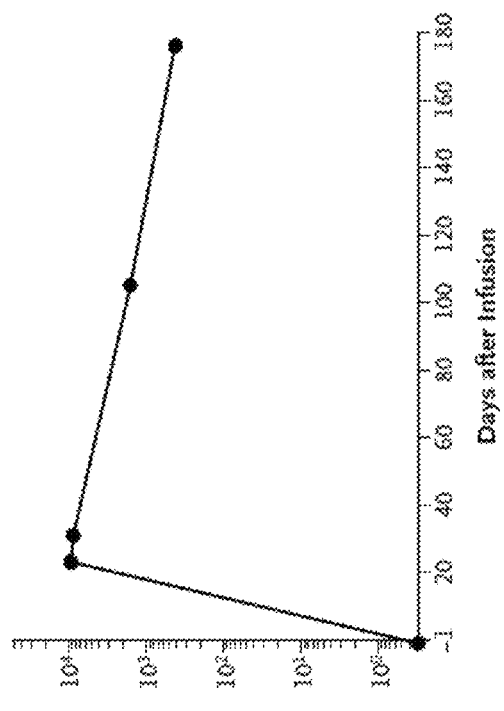
Figure 14A:
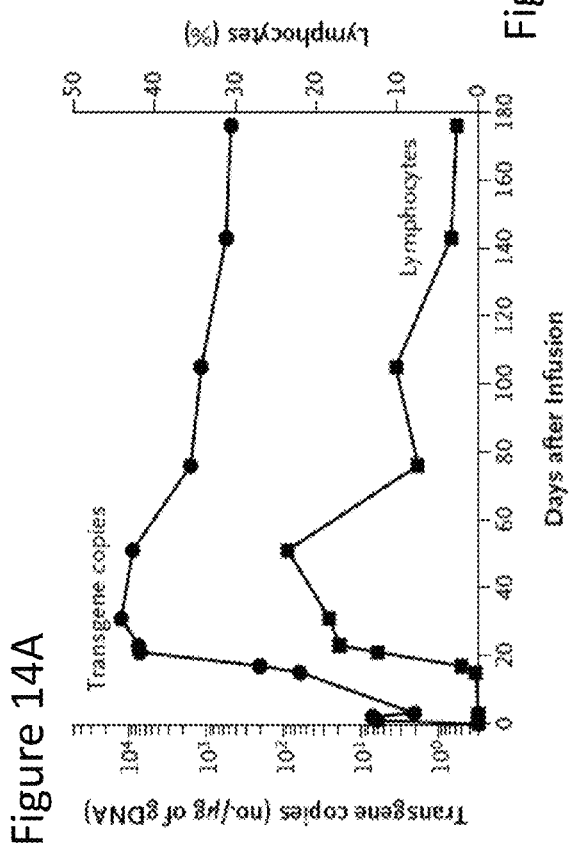

Real-time PCR detected DNA encoding anti-CD19 chimeric antigen receptor (CAR19) beginning on day 1 after the first infusion (FIG. 14A). More than a 3-log expansion of the cells in vivo was noted by day 21 after infusion. At peak levels, CART19 cells in blood accounted for more than 20% of circulating lymphocytes; these peak levels coincided with the occurrence of constitutional symptoms, the tumor lysis syndrome (FIG. 12B), and elevations in serum cytokine levels (FIG. 13A through FIG. 13D). CART19 cells remained detectable at high levels 6 months after the infusions, though the values decreased by a factor of 10 from peak levels. The doubling time of chimeric antigen receptor T cells in blood was approximately 1.2 days, with an elimination half-life of 31 days.

Chimeric Antigen Receptor T Cells in Bone Marrow

CART19 cells were identified in bone marrow specimens beginning 23 days after the first infusion (FIG. 14B) and persisted for at least 6 months, with a decay half-life of 34 days. The highest levels of CART19 cells in the bone marrow were identified at the first assessment 23 days after the first infusion and coincided with induction of an immune response, as indicated by cytokine-secretion profiles (FIG. 13E). Flow-cytometric analysis of bone marrow aspirates indicated a clonal expansion of CD5+CD19+ cells at baseline that was absent 1 month after infusion and in a sample obtained 3 months after infusion (data not shown). Normal B cells were not detected after treatment (FIG. 14C).

Treatment with Autologous Genetically Modified CART19 Cells

Described herein is the delayed development of the tumor lysis syndrome and a complete response 3 weeks after treatment with autologous T cells genetically modified to target CD19 through transduction with a lentivirus vector expressing anti-CD19 linked to CD3-zeta and CD137 (4-1BB) signaling domains. Genetically modified cells were present at high levels in bone marrow for at least 6 months after infusion. The generation of a CD19-specific immune response in bone marrow was demonstrated by temporal release of cytokines and ablation of leukemia cells that coincided with peak infiltration of chimeric antigen receptor T cells. Development of the tumor lysis syndrome after cellular immunotherapy has not been reported previously (Baeksgaard et al., 2003, Cancer Chemother Pharacol, 51: 187-92).

Genetic manipulation of autologous T cells to target specific tumor antigens is an attractive strategy for cancer therapy (Sadelain et al., 2009, Curr Opin Immunol, 21: 215-23; Jena et al., 2010, Blood, 116: 1035-44). An important feature of the approach described herein is that chimeric antigen receptor T cells can recognize tumor targets in an HLA-unrestricted manner, so that "off-the-shelf" chimeric antigen receptors can be constructed for tumors with a wide variety of histologic features. HIV-derived lentiviral vectors were used for cancer therapy, an approach that may have some advantages over the use of retroviral vectors (June et al., 2009, Nat Rev Immunol, 9: 704-16).

In previous trials of chimeric antigen receptor T cells, objective tumor responses have been modest, and in vivo proliferation of modified cells has not been sustained (Kershaw et al., 2006, Clin Cancer Res, 12: 6106-15; Till et al., 2008, Blood, 112: 2261-71; Pule et al., 2008, Nat Med, 14: 1264-70). Brentjens and colleagues reported preliminary results of a clinical trial of CD19-targeted chimeric antigen receptors linked to a CD28 signaling domain and found transient tumor responses in two of three patients with advanced CLL (Brentjens et al., 2010, Mol Ther, 18: 666-8); however, the chimeric antigen receptors rapidly disappeared from the circulation.

It was unexpected that the very low dose of chimeric antigen receptor T cells that were infused would result in a clinically evident antitumor response. Indeed, the infused dose of $1.5 \times 10^5$ chimeric antigen receptor T cells per kilogram was several orders of magnitude below doses used in previous studies of T cells modified to express chimeric antigen receptors or transgenic T-cell receptors (Kershaw et al., 2006, Clin Cancer Res, 12: 6106-15; Brentjens et al., 2010, Mol Ther, 18: 666-8; Morgan et al., 2010, Mol Ther, 18: 843-51; Johnson et al., 2009, Blood, 114: 535-46). Without being held to any particular theory, it is speculated that the chemotherapy may potentiate the effects of chimeric antigen receptor.

The prolonged persistence of CART19 cells in the blood and bone marrow of the patient results from inclusion of the 4-1BB signaling domain. It is likely that the CART19-cell-mediated elimination of normal B cells facilitated the induction of immunologic tolerance to the chimeric antigen receptor, since the CART19 cells that express the single-chain Fv antibody fragment containing murine sequences were not rejected. Given the absence of detectable CD19-positive leukemia cells in this patient, and without being held to any particular theory, it is possible that homeostasis of the chimeric antigen receptor T cells was achieved at least in part from stimulation delivered by early B-cell progenitors as they began to emerge in the bone marrow. The invention relates to the discovery that a new mechanism may exist to maintain "memory" chimeric antigen receptor T cells.

Although CD19 is an attractive tumor target, with expression limited to normal and malignant B cells, there is concern that persistence of the chimeric antigen receptor T cells may mediate long-term B-cell deficiency. In fact, in the patient, B cells were absent from the blood and bone marrow for at least 6 months after infusion. This patient did not have recurrent infections. Targeting B cells through CD20 with rituximab is an effective and relatively safe strategy for patients with B-cell neoplasms, and long-term B-cell lymphopenia is manageable (Molina, 2008, Ann Rev Med, 59: 237-50). Patients treated with rituximab have been reported to have a return of B cells within months after discontinuation of therapy. It is not yet clear whether such recovery occurs in patients whose anti-B-cell T cells persist in vivo.

Patients who have CLL with TP53 deletions have short remissions after standard therapies (Dohner et al., 1995, Blood, 85: 1580-9). Allogeneic bone marrow transplantation has been the only approach that has induced long-term remissions in patients with advanced CLL (Gribben et al., 2011, Biol Blood Marrow Transplant, 17: Suppl:S63-S70). However, the resulting potent graft-versus-tumor effect is associated with considerable morbidity because of the high frequency of chronic graft-versus-host disease, which is often especially severe in older patients—those who are typically affected by CLL (Gribben et al., 2011, Biol Blood Marrow Transplant, 17: Suppl:S63-S70; Sorror or et al., 2008, Blood, 111: 446-52). The data presented herein suggests that genetically modified autologous T cells may circumvent this limitation.

The delayed onset of the tumor lysis syndrome and cytokine secretion, combined with vigorous in vivo chimeric antigen receptor T-cell expansion and prominent antileukemia activity, points to substantial and sustained effector functions of the CART19 cells. Experiments described herein highlights the potency of this therapy and provides support for the detailed study of autologous T cells genetically modified to target CD19 (and other targets) through transduction of a chimeric antigen receptor linked to potent signaling domains. Unlike antibody-mediated therapy, chimeric antigen receptor-modified T cells have the potential to replicate in vivo, and long-term persistence could lead to sustained tumor control. Two other patients with advanced CLL have also received CART19 infusions according to this protocol, and all three have had tumor responses. These findings warrant continued study of CD19-redirected T cells for B-cell neoplasms.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating leukemia in a human patient, the method comprising administering to the human patient a pharmaceutical composition comprising an anti-tumor effective amount of a population of human T cells, wherein the T cells comprise a nucleic acid sequence that encodes a chimeric antigen receptor (CAR), wherein the CAR comprises a CD19 antigen binding domain comprising the amino acid sequence of SEQ ID NO:20, a CD8α hinge domain, a CD8α transmembrane domain, a 4-1 BB costimulatory signaling region, and a CD3 zeta signaling domain comprising the amino acid sequence of SEQ ID NO:24, wherein the T cells are T cells of the human patient having leukemia.

2. The method of claim 1, wherein the anti-tumor effective amount of T cells is $10^4$ to $10^9$ cells per kg body weight of the human patient.

3. The method of claim 1, wherein the anti-tumor effective amount of T cells is $10^5$ to $10^6$ cells per kg body weight of the human patient.

4. The method of claim 1, wherein the CD8α transmembrane domain comprises the amino acid sequence of SEQ ID NO: 22.

5. The method of claim 1, wherein the CD8α hinge domain comprises the amino acid sequence of SEQ ID NO: 21.

6. The method of claim 1, wherein the 4-1BB costimulatory signaling region comprises the amino acid sequence of SEQ ID NO: 23.

7. The method of claim 1, wherein the CD19 binding domain is encoded by a nucleic acid sequence comprising SEQ ID NO: 14.

8. The method of claim 4, wherein the CD8α transmembrane domain is encoded by a nucleic acid sequence comprising SEQ ID NO: 16.

9. The method of claim 5, wherein the CD8α hinge domain is encoded by a nucleic acid sequence comprising SEQ ID NO: 15.

10. The method of claim 6, wherein the 4-1BB costimulatory signaling region is encoded by a nucleic acid sequence comprising SEQ ID NO: 17.

11. The method of claim 1, wherein the CD3 zeta signaling domain is encoded by a nucleic acid sequence comprising SEQ ID NO: 18.

12. The method of claim 1, wherein the T cells replicate in vivo in the human patient.

13. The method of claim 1, wherein the T cells form memory T cells in the human patient.

14. The method of claim 1, wherein the T cells are administered intravenously to the human patient.

15. The method of claim 1, wherein the T cells persist in the human patient.

16. The method of claim 15, wherein the T cells persist in the human patient for a period selected from the group consisting of at least three months, at least four months, at last five months, at least six months and at least seven months after administration.

17. The method of claim 15, wherein the T cells persist in the human patient for at least eight months after administration.

18. The method of claim 15, wherein the T cells persist in the human patient for at least nine months after administration.

19. The method of claim 15, wherein the T cells persist in the human patient for at least ten months after administration.

20. The method of claim 15, wherein the T cells persist in the human patient for at least eleven months after administration.

21. The method of claim 15, wherein the T cells persist in the human patient for at least twelve months after administration.

22. The method of claim 15, wherein the T cells persist in the human patient for at least two years after administration.

23. The method of claim 15, wherein the T cells persist in the human patient for at least three years after administration.

24. A method of treating leukemia in a human patient, the method comprising administering to the human patient a pharmaceutical composition comprising an anti-tumor effective amount of a population of human T cells, wherein the T cells comprise a nucleic acid sequence that encodes a chimeric antigen receptor (CAR), wherein the CAR comprises a CD19 antigen binding domain comprising the amino acid sequence of SEQ ID NO:20, a CD8α hinge domain comprising the amino acid sequence of SEQ ID NO:21, a CD8α transmembrane domain comprising the amino acid sequence of SEQ ID NO:22, a 4-1 BB costimulatory signaling region comprising the amino acid sequence of SEQ ID NO:23, and a CD3 zeta signaling domain comprising the amino acid sequence of SEQ ID NO:24, wherein the T cells are T cells of the human patient having leukemia.

25. The method of claim 24, wherein the CD19 antigen binding domain of the CAR is encoded by a nucleic acid sequence comprising SEQ ID NO:14, the CD8α hinge domain of the CAR is encoded by a nucleic acid sequence comprising SEQ ID NO:15, the CD8α transmembrane domain of the CAR is encoded by a nucleic acid sequence comprising SEQ ID NO:16, the 4-1BB costimulatory signaling region of the CAR is encoded by a nucleic acid sequence comprising SEQ ID NO:17, and the CD3 zeta signaling domain of the CAR is encoded by a nucleic acid sequence comprising SEQ ID NO:18.

26. A method of treating chronic lymphocytic leukemia (CLL) in a human patient, the method comprising administering to the human patient a pharmaceutical composition comprising an anti-tumor effective amount of a population of human T cells, wherein the T cells comprise a nucleic acid sequence that encodes a chimeric antigen receptor (CAR), wherein the CAR comprises a CD19 antigen binding domain comprising the amino acid sequence of SEQ ID NO:20, a CD8α hinge domain comprising the amino acid sequence of SEQ ID NO:21, a CD8α transmembrane domain comprising the amino acid sequence of SEQ ID NO:22, a 4-1 BB costimulatory signaling region comprising the amino acid sequence of SEQ ID NO:23, and a CD3 zeta signaling domain comprising the amino acid sequence of SEQ ID NO:24, wherein the T cells are T cells of the human patient having CLL.

27. The method of claim 26, wherein the CD19 antigen binding domain of the CAR is encoded by a nucleic acid sequence comprising SEQ ID NO:14, the CD8α hinge domain of the CAR is encoded by a nucleic acid sequence comprising SEQ ID NO:15, the CD8α transmembrane domain of the CAR is encoded by a nucleic acid sequence comprising SEQ ID NO:16, the 4-1BB costimulatory signaling region of the CAR is encoded by a nucleic acid sequence comprising SEQ ID NO:17, and the CD3 zeta signaling domain of the CAR is encoded by a nucleic acid sequence comprising SEQ ID NO:18.

28. A method of treating acute lymphocytic leukemia (ALL) in a human patient, the method comprising administering to the human patient a pharmaceutical composition comprising an anti-tumor effective amount of a population of human T cells, wherein the T cells comprise a nucleic acid sequence that encodes a chimeric antigen receptor (CAR), wherein the CAR comprises a CD19 antigen binding domain comprising the amino acid sequence of SEQ ID NO:20, a CD8α hinge domain comprising the amino acid sequence of SEQ ID NO:21, a CD8α transmembrane domain comprising the amino acid sequence of SEQ ID NO:22, a 4-1 BB costimulatory signaling region comprising the amino acid sequence of SEQ ID NO:23, and a CD3 zeta signaling domain comprising the amino acid sequence of SEQ ID NO:24, wherein the T cells are T cells of the human patient having ALL.

29. The method of claim 28, wherein the CD19 antigen binding domain of the CAR is encoded by a nucleic acid sequence comprising SEQ ID NO:14, the CD8α hinge domain of the CAR is encoded by a nucleic acid sequence comprising SEQ ID NO:15, the CD8α transmembrane domain of the CAR is encoded by a nucleic acid sequence comprising SEQ ID NO:16, the 4-1BB costimulatory signaling region of the CAR is encoded by a nucleic acid sequence comprising SEQ ID NO:17, and the CD3 zeta signaling domain of the CAR is encoded by a nucleic acid sequence comprising SEQ ID NO:18.

30. The method of claim 1, wherein the leukemia is chronic myelogenous leukemia (CML).

\* \* \* \* \*

SEQUENCE LISTING

```
<160> NUMBER OF SEQ ID NOS: 27

<210> SEQ ID NO 1
<211> LENGTH: 9174
<212> TYPE: DNA
<213> ORGANISM: Artificial Sequence
<220> FEATURE:
<223> OTHER INFORMATION: Chemically Synthesized

<400> SEQUENCE: 1
gcgcgctcac tggccgtcgt tttacaacgt cgtgactggg aaaaccctgg cgttacccaa      60
cttaatcgcc ttgcagcaca tccccctttc gccagctggc gtaatagcga agaggcccgc     120
accgatcgcc cttcccaaca gttgcgcagc ctgaatggcg aatgggacgc gccctgtagc     180
ggcgcattaa gcgcggcggg tgtggtggtt acgcgcagcg tgaccgctac acttgccagc     240
gccctagcgc ccgctccttt cgctttcttc ccttcctttc tcgccacgtt cgccggcttt     300
ccccgtcaag ctctaaatcg ggggctccct ttagggttcc gatttagtgc tttacggcac     360
ctcgacccca aaaaacttga ttagggtgat ggttcacgta gtgggccatc gccctgatag     420 acggttttc gccctttgac gttggagtcc acgttcttta atagtggact cttgttccaa     480
actggaacaa cactcaaccc tatctcggtc tattcttttg atttataagg gattttgccg     540
atttcggcct attggttaaa aaatgagctg atttaacaaa aatttaacgc gaattttaac     600
```

```
aaaatattaa cgcttacaat ttaggtggca cttttcgggg aaatgtgcgc ggaacccta       660 tttgtttatt tttctaaata cattcaaata tgtatccgct catgagacaa taaccctgat       720
aaatgcttca ataatattga aaaggaaga gtatgagtat tcaacatttc cgtgtcgccc        780
ttattccctt ttttgcggca ttttgccttc ctgttttttgc tcacccagaa acgctggtga     840
aagtaaaaga tgctgaagat cagttgggtg cacgagtggg ttacatcgaa ctggatctca      900
acagcggtaa gatccttgag agttttcgcc ccgaagaacg ttttccaatg atgagcactt      960
ttaaagttct gctatgtggc gcggtattat cccgtattga cgccgggcaa gagcaactcg     1020
gtcgccgcat acactattct cagaatgact tggttgagta ctcaccagtc acagaaaagc     1080
atcttacgga tggcatgaca gtaagagaat tatgcagtgc tgccataacc atgagtgata    1140
acactgcggc caacttactt ctgacaacga tcggaggacc gaaggagcta accgcttttt    1200
tgcacaacat gggggatcat gtaactcgcc ttgatcgttg ggaaccggag ctgaatgaag    1260
ccataccaaa cgacgagcgt gacaccacga tgcctgtagc aatggcaaca acgttgcgca    1320
aactattaac tggcgaacta cttactctag cttcccggca acaattaata gactggatgg    1380
aggcggataa agttgcagga ccacttctgc gctcggccct tccggctggc tggtttattg    1440
ctgataaatc tggagccggt gagcgtgggt ctcgcggtat cattgcagca ctggggccag    1500
atggtaagcc ctcccgtatc gtagttatct acacgacggg gagtcaggca actatggatg    1560
aacgaaatag acagatcgct gagataggtg cctcactgat taagcattgg taactgtcag    1620
accaagttta ctcatatata ctttagattg atttaaaact tcattttttaa tttaaaagga    1680 tctaggtgaa gatcctttt gataatctca tgaccaaaat cccttaacgt gagttttcgt     1740
tccactgagc gtcagacccc gtagaaaaga tcaaaggatc ttcttgagat cctttttttc    1800
tgcgcgtaat ctgctgcttg caaacaaaaa aaccaccgct accagcggtg gtttgtttgc    1860
cggatcaaga gctaccaact cttttttccga aggtaactgg cttcagcaga gcgcagatac   1920
caaatactgt tcttctagtg tagccgtagt taggccacca cttcaagaac tctgtagcac    1980
cgcctacata cctcgctctg ctaatcctgt taccagtggc tgctgccagt ggcgataagt    2040
cgtgtcttac cgggttggac tcaagacgat agttaccgga taaggcgcag cggtcgggct    2100 gaacggggg ttcgtgcaca cagcccagct tggagcgaac gacctacacc gaactgagat     2160
acctacagcg tgagctatga gaaagcgcca cgcttcccga aggagaaag gcggacaggt      2220 atccggtaag cggcagggtc ggaacaggag agcgcacgag ggagcttcca gggggaaacg     2280
cctggtatct ttatagtcct gtcgggtttc gccacctctg acttgagcgt cgatttttgt    2340
gatgctcgtc agggggggcgg agcctatgga aaaacgccag caacgcggcc ttttacggt     2400 tcctggcctt ttgctggcct tttgctcaca tgttctttcc tgcgttatcc cctgattctg    2460
tggataaccg tattaccgcc tttgagtgag ctgataccgc tcgccgcagc cgaacgaccg    2520
agcgcagcga gtcagtgagc gaggaagcgg aagagcgccc aatacgcaaa ccgcctctcc    2580
ccgcgcgttg gccgattcat taatgcagct ggcacgacag gtttcccgac tggaaagcgg    2640
gcagtgagcg caacgcaatt aatgtgagtt agctcactca ttaggcaccc caggctttac    2700
actttatgct tccggctcgt atgttgtgtg gaattgtgag cggataacaa tttcacacag    2760
gaaacagcta tgaccatgat tacgccaagc gcgcaattaa ccctcactaa agggaacaaa    2820
agctggagct gcaagcttaa tgtagtctta tgcaatactc ttgtagtctt gcaacatggt    2880
aacgatgagt tagcaacatg ccttacaagg agagaaaaag caccgtgcat gccgattggt    2940
```

```
ggaagtaagg tggtacgatc gtgccttatt aggaaggcaa cagacgggtc tgacatggat    3000
tggacgaacc actgaattgc cgcattgcag agatattgta tttaagtgcc tagctcgata    3060
cataaacggg tctctctggt tagaccagat ctgagcctgg gagctctctg gctaactagg    3120
gaacccactg cttaagcctc aataaagctt gccttgagtg cttcaagtag tgtgtgcccg    3180
tctgttgtgt gactctggta actagagatc cctcagaccc ttttagtcag tgtggaaaat    3240
ctctagcagt ggcgcccgaa cagggacttg aaagcgaaag ggaaaccaga ggagctctct    3300
cgacgcagga ctcggcttgc tgaagcgcgc acggcaagag gcgaggggcg cgactggtg    3360
agtacgccaa aaattttgac tagcggaggc tagaaggaga gagatgggtg cgagagcgtc    3420
agtattaagc gggggagaat tagatcgcga tgggaaaaaa ttcggttaag ccagggggga    3480
aagaaaaaat ataaattaaa acatatagta tgggcaagca gggagctaga acgattcgca    3540
gttaatcctg gcctgttaga aacatcagaa ggctgtagac aaatactggg acagctacaa    3600
ccatcccttc agacaggatc agaagaactt agatcattat ataatacagt agcaaccctc    3660
tattgtgtgc atcaaaggat agagataaaa gacaccaagg aagctttaga caagatagag    3720
gaagagcaaa acaaaagtaa gaccaccgca cagcaagcgg ccgctgatct tcagacctgg    3780
aggaggagat atgagggaca attggagaag tgaattatat aaatataaag tagtaaaaat    3840
tgaaccatta ggagtagcac ccaccaaggc aaagagaaga gtggtgcaga gagaaaaaag    3900
agcagtggga ataggagctt tgttccttgg gttcttggga gcagcaggaa gcactatggg    3960
cgcagcgtca atgacgctga cggtacaggc cagacaatta ttgtctggta tagtgcagca    4020
gcagaacaat ttgctgaggg ctattgaggc gcaacagcat ctgttgcaac tcacagtctg    4080
gggcatcaag cagctccagg caagaatcct ggctgtggaa agatacctaa aggatcaaca    4140
gctcctgggg atttggggtt gctctggaaa actcatttgc accactgctg tgccttggaa    4200
tgctagttgg agtaataaat ctctggaaca gatttggaat cacacgacct ggatggagtg    4260
ggacagagaa attaacaatt acacaagctt aatacactcc ttaattgaag aatcgcaaaa    4320
ccagcaagaa aagaatgaac aagaattatt ggaattagat aaatgggcaa gtttgtggaa    4380
ttggtttaac ataacaaatt ggctgtggta tataaaatta ttcataatga tagtaggagg    4440
cttggtaggt ttaagaatag ttttgctgt actttctata gtgaatagag ttaggcaggg    4500
atattcacca ttatcgtttc agacccacct cccaaccccg aggggacccg acaggcccga    4560
aggaatagaa gaagaaggtg gagagagaga cagagacaga tccattcgat tagtgaacgg    4620
atctcgacgg tatcgattag actgtagccc aggaatatgg cagctagatt gtacacattt    4680
agaaggaaaa gttatcttgg tagcagttca tgtagccagt ggatatatag aagcagaagt    4740
aattccagca gagacagggc aagaaacagc atacttcctc ttaaaattag caggaagatg    4800
gccagtaaaa acagtacata cagacaatgg cagcaatttc accagtacta cagttaaggc    4860
cgcctgttgg tgggcgggga tcaagcagga atttggcatt ccctacaatc cccaaagtca    4920
aggagtaata gaatctatga ataaagaatt aagaaaatt ataggacagg taagagatca    4980
ggctgaacat cttaagacag cagtacaaat ggcagtattc atccacaatt ttaaaagaaa    5040
agggggggatt ggggggtaca gtgcagggga agaatagta gacataatag caacagacat    5100
acaaactaaa gaattacaaa aacaaattac aaaaattcaa aattttcggg tttattacag    5160
ggacagcaga gatccagttt ggctgcattg atcacgtgag gctccggtgc ccgtcagtgg    5220
gcagagcgca catcgcccac agtccccgag aagttggggg gaggggtcgg caattgaacc    5280
ggtgcctaga gaaggtggcg cggggtaaac tgggaaagtg atgtcgtgta ctggctccgc    5340
```

```
cttttttcccg agggtgggggg agaaccgtat ataagtgcag tagtcgccgt gaacgttctt    5400
tttcgcaacg ggtttgccgc cagaacacag gtaagtgccg tgtgtggttc ccgcgggcct    5460
ggcctcttta cgggttatgg cccttgcgtg ccttgaatta cttccacctg gctgcagtac    5520
gtgattcttg atcccgagct tcgggttgga agtgggtggg agagttcgag gccttgcgct    5580
taaggagccc cttcgcctcg tgcttgagtt gaggcctggc ctgggcgctg ggccgccgc    5640 gtgcgaatct ggtggcacct tcgcgcctgt ctcgctgctt tcgataagtc tctagccatt    5700
taaaattttt gatgacctgc tgcgacgctt tttttctggc aagatagtct tgtaaatgcg    5760
ggccaagatc tgcacactgg tatttcggtt tttggggccg cgggcggcga cggggcccgt    5820
gcgtcccagc gcacatgttc ggcgaggcgg ggcctgcgag cgcggccacc gagaatcgga    5880 cggggggtagt ctcaagctgg ccggcctgct ctggtgcctg gcctcgcgcc gccgtgtatc    5940
gccccgccct gggcggcaag gctggcccgg tcggcaccag ttgcgtgagc ggaaagatgg    6000
ccgcttcccg gccctgctgc agggagctca aaatggagga cgcggcgctc gggagagcgg    6060
gcgggtgagt cacccacaca aggaaaagg gcctttccgt cctcagccgt cgcttcatgt    6120
gactccactg agtaccgggc gccgtccagg cacctcgatt agttctcgag cttttggagt    6180
acgtcgtctt taggttgggg ggaggggttt tatgcgatgg agtttcccca cactgagtgg    6240
gtggagactg aagttaggcc agcttggcac ttgatgtaat tctccttgga atttgccctt    6300
tttgagtttg gatcttggtt cattctcaag cctcagacag tggttcaaag ttttttttctt    6360 ccatttcagg tgtcgtgatc tagaggatcc atggccttac cagtgaccgc cttgctcctg    6420
ccgctggcct tgctgctcca cgccgccagg ccggacatcc agatgacaca gactacatcc    6480
tccctgtctg cctctctggg agacagagtc accatcagtt gcagggcaag tcaggacatt    6540
agtaaatatt taaattggta tcagcagaaa ccagatggaa ctgttaaact cctgatctac    6600
catacatcaa gattacactc aggagtccca tcaaggttca gtggcagtgg gtctggaaca    6660
gattattctc tcaccattag caacctggag caagaagata ttgccactta cttttgccaa    6720
cagggtaata cgcttccgta cacgttcgga ggggggacca agctggagat cacaggtggc    6780
ggtggctcgg gcggtggtgg gtcgggtggc ggcggatctg aggtgaaact gcaggagtca    6840
ggacctggcc tggtggcgcc ctcacagagc ctgtccgtca catgcactgt ctcaggggtc    6900
tcattacccg actatggtgt aagctggatt cgccagcctc cacgaaaggg tctggagtgg    6960
ctgggagtaa tatggggtag tgaaaccaca tactataatt cagctctcaa atccagactg    7020
accatcatca aggacaactc caagagccaa gttttcttaa aaatgaacag tctgcaaact    7080
gatgacacag ccatttacta ctgtgccaaa cattattact acggtggtag ctatgctatg    7140
gactactggg gccaaggaac ctcagtcacc gtctcctcaa ccacgacgcc agcgccgcga    7200
ccaccaacac cggcgcccac catcgcgtcg cagcccctgt ccctgcgccc agaggcgtgc    7260
cggccagcgg cgggggggcgc agtgcacacg aggggggctgg acttcgcctg tgatatctac    7320
atctgggcgc ccttggccgg gacttgtggg gtccttctcc tgtcactggt tatcaccctt    7380
tactgcaaac ggggcagaaa gaaactcctg tatatattca acaaccatt tatgagacca    7440 gtacaaacta ctcaagagga agatggctgt agctgccgat ttccagaaga agaagaagga    7500
ggatgtgaac tgagagtgaa gttcagcagg agcgcagacg ccccgcgta caagcagggc    7560 cagaaccagc tctataacga gctcaatcta ggacgaagag aggagtacga tgttttggac    7620
aagagacgtg gccgggaccc tgagatgggg ggaaagccga gaaggaagaa ccctcaggaa    7680
```

```
ggcctgtaca atgaactgca gaaagataag atggcggagg cctacagtga gattgggatg    7740
aaaggcgagc gccggagggg caaggggcac gatggccttt accagggtct cagtacagcc    7800
accaaggaca cctacgacgc ccttcacatg caggccctgc cccctcgcta agtcgacaat    7860
caacctctgg attacaaaat tgtgaaaga ttgactggta ttcttaacta tgttgctcct    7920
tttacgctat gtggatacgc tgctttaatg cctttgtatc atgctattgc ttcccgtatg    7980
gctttcattt tctcctcctt gtataaatcc tggttgctgt ctctttatga ggagttgtgg    8040
cccgttgtca ggcaacgtgg cgtggtgtgc actgtgtttg ctgacgcaac ccccactggt    8100
tggggcattg ccaccacctg tcagctcctt tccgggactt tcgctttccc cctccctatt    8160
gccacggcgg aactcatcgc cgcctgcctt gcccgctgct ggacaggggc tcggctgttg    8220
ggcactgaca attccgtggt gttgtcgggg aagctgacgt cctttccatg gctgctcgcc    8280
tgtgttgcca cctggattct gcgcgggacg tccttctgct acgtcccttc ggccctcaat    8340
ccagcggacc ttccttcccg cggcctgctg ccggctctgc ggcctcttcc gcgtcttcgc    8400
cttcgccctc agacgagtcg gatctccctt gggccgcct cccgcctgg aattcgagct    8460 cggtaccttt aagaccaatg acttacaagg cagctgtaga tcttagccac ttttttaaaag    8520 aaaaggggg actggaaggg ctaattcact cccaacgaag acaagatctg cttttttgctt    8580 gtactgggtc tctctggtta gaccagatct gagcctggga gctctctggc taactaggga    8640
acccactgct taagcctcaa taaagcttgc cttgagtgct tcaagtagtg tgtgcccgtc    8700
tgttgtgtga ctctggtaac tagagatccc tcagacccctt ttagtcagtg tggaaaatct    8760
ctagcagtag tagttcatgt catcttatta ttcagtattt ataacttgca aagaaatgaa    8820
tatcagagag tgagaggaac ttgtttattg cagcttataa tggttacaaa taaagcaata    8880
gcatcacaaa tttcacaaat aaagcatttt tttcactgca ttctagttgt ggtttgtcca    8940
aactcatcaa tgtatcttat catgtctggc tctagctatc ccgcccctaa ctccgcccat    9000 cccgcccta actccgccca gttccgccca ttctccgccc catggctgac taatttttttt    9060 tatttatgca gaggccgagg ccgcctcggc ctctgagcta ttccagaagt agtgaggagg    9120
cttttttgga ggcctaggga cgtacccaat tcgccctata gtgagtcgta ttac          9174
```

```
<210> SEQ ID NO 2
<211> LENGTH: 228
<212> TYPE: DNA
<213> ORGANISM: Artificial Sequence
<220> FEATURE:
<223> OTHER INFORMATION: Chemically Synthesized

<400> SEQUENCE: 2
atgtagtctt atgcaatact cttgtagtct tgcaacatgg taacgatgag ttagcaacat    60
gccttacaag gagagaaaaa gcaccgtgca tgccgattgg tggaagtaag gtggtacgat    120
cgtgccttat taggaaggca acagacgggt ctgacatgga ttggacgaac cactgaattg    180
ccgcattgca gagatattgt atttaagtgc ctagctcgat acataaac                 228
```

```
<210> SEQ ID NO 3
<211> LENGTH: 98
<212> TYPE: DNA
<213> ORGANISM: Artificial Sequence
<220> FEATURE:
<223> OTHER INFORMATION: Chemically Synthesized

<400> SEQUENCE: 3
gggtctctct ggttagacca gatctgagcc tgggagctct ctggctaact agggaaccca    60
```

```
ctgcttaagc ctcaataaag cttgccttga gtgcttca                              98
```

<210> SEQ ID NO 4
<211> LENGTH: 85
<212> TYPE: DNA
<213> ORGANISM: Artificial Sequence
<220> FEATURE:
<223> OTHER INFORMATION: Chemically Synthesized

<400> SEQUENCE: 4

```
agtagtgtgt gcccgtctgt tgtgtgactc tggtaactag agatccctca gacccttta     60 gtcagtgtgg aaaatctcta gcagt                                          85
```

<210> SEQ ID NO 5
<211> LENGTH: 1377
<212> TYPE: DNA
<213> ORGANISM: Artificial Sequence
<220> FEATURE:
<223> OTHER INFORMATION: Chemically Synthesized

<400> SEQUENCE: 5

```
cgaacaggga cttgaaagcg aaagggaaac cagaggagct ctctcgacgc aggactcggc     60
ttgctgaagc gcgcacggca agaggcgagg ggcggcgact ggtgagtacg ccaaaaattt    120
tgactagcgg aggctagaag gagagagatg ggtgcgagag cgtcagtatt aagcggggga    180
gaattagatc gcgatgggaa aaaattcggt taaggccagg gggaagaaaa aatataaat    240 taaaacatat agtatgggca agcagggagc tagaacgatt cgcagttaat cctggcctgt    300
tagaaacatc agaaggctgt agacaaatac tgggacagct acaaccatcc cttcagacag    360
gatcagaaga acttagatca ttatataata cagtagcaac cctctattgt gtgcatcaaa    420
ggatagagat aaaagacacc aaggaagctt tagacaagat agaggaagag caaaacaaaa    480
gtaagaccac cgcacagcaa gcggccgctg atcttcagac ctggaggagg agatatgagg    540
gacaattgga gaagtgaatt atataaatat aaagtagtaa aaattgaacc attaggagta    600
gcacccacca aggcaaagag aagagtggtg cagagagaaa aaagagcagt gggaatagga    660
gctttgttcc ttgggttctt gggagcagca ggaagcacta tgggcgcagc gtcaatgacg    720
ctgacggtac aggccagaca attattgtct ggtatagtgc agcagcagaa caatttgctg    780
agggctattg aggcgcaaca gcatctgttg caactcacag tctggggcat caagcagctc    840
caggcaagaa tcctggctgt ggaaagatac ctaaaggatc aacagctcct ggggatttgg    900
ggttgctctg gaaaactcat ttgcaccact gctgtgcctt ggaatgctag ttggagtaat    960
aaatctctgg aacagatttg gaatcacacg acctggatgg agtgggacag agaaattaac   1020
aattacacaa gcttaataca ctccttaatt gaagaatcgc aaaaccagca agaaaagaat   1080
gaacaagaat tattggaatt agataaatgg gcaagtttgt ggaattggtt taacataaca   1140
aattggctgt ggtatataaa attattcata atgatagtag gaggcttggt aggtttaaga   1200 atagttttg ctgtactttc tatagtgaat agagttaggc agggatattc accattatcg   1260
tttcagaccc acctcccaac cccgagggga cccgacaggc ccgaaggaat agaagaagaa   1320
ggtggagaga gagacagaga cagatccatt cgattagtga acggatctcg acggtat      1377
```

<210> SEQ ID NO 6
<211> LENGTH: 547
<212> TYPE: DNA
<213> ORGANISM: Artificial Sequence
<220> FEATURE:

<223> OTHER INFORMATION: Chemically Synthesized

<400> SEQUENCE: 6

```
tagactgtag cccaggaata tggcagctag attgtacaca tttagaagga aaagttatct      60
tggtagcagt tcatgtagcc agtggatata tagaagcaga agtaattcca gcagagacag     120
ggcaagaaac agcatacttc ctcttaaaat tagcaggaag atggccagta aaaacagtac     180
atacagacaa tggcagcaat ttcaccagta ctacagttaa ggccgcctgt tggtgggcgg     240
ggatcaagca ggaatttggc attccctaca atccccaaag tcaaggagta atagaatcta     300
tgaataaaga attaaagaaa attataggac aggtaagaga tcaggctgaa catcttaaga     360
cagcagtaca aatggcagta ttcatccaca attttaaaag aaaagggggg attggggggt     420
acagtgcagg ggaaagaata gtagacataa tagcaacaga catacaaact aaagaattac     480
aaaaacaaat tacaaaaatt caaaattttc gggtttatta cagggacagc agagatccag     540
tttggct                                                                547
```

<210> SEQ ID NO 7
<211> LENGTH: 1178
<212> TYPE: DNA
<213> ORGANISM: Artificial Sequence
<220> FEATURE:
<223> OTHER INFORMATION: Chemically Synthesized

<400> SEQUENCE: 7

```
gctccggtgc ccgtcagtgg cagagcgca catcgcccac agtccccgag aagttgggggg      60
gaggggtcgg caattgaacc ggtgcctaga aaggtggcg cggggtaaac tgggaaagtg     120
atgtcgtgta ctggctccgc cttttttcccg agggtgggg agaaccgtat ataagtgcag     180
tagtcgccgt gaacgttctt tttcgcaacg ggtttgccgc cagaacacag gtaagtgccg     240
tgtgtggttc ccgcgggcct ggcctcttta cgggttatgg cccttgcgtg ccttgaatta     300
cttccacctg gctgcagtac gtgattcttg atcccgagct tcgggttgga agtgggtggg     360
agagttcgag gccttgcgct taaggagccc cttcgcctcg tgcttgagtt gaggcctggc     420
ctgggcgctg gggccgccgc gtgcgaatct ggtggcacct tcgcgcctgt ctcgctgctt     480
tcgataagtc tctagccatt taaaatttt gatgacctgc tgcgacgctt ttttctggc     540
aagatagtct tgtaaatgcg ggccaagatc tgcacactgg tatttcggtt tttggggccg     600
cgggcggcga cggggcccgt gcgtcccagc gcacatgttc ggcgaggcgg ggcctgcgag     660
cgcggccacc gagaatcgga cggggtagt ctcaagctgg ccggcctgct ctggtgcctg     720
gcctcgcgcc gccgtgtatc gccccgccct gggcggcaag gctggcccgg tcggcaccag     780
ttgcgtgagc ggaaagatgg ccgcttcccg gccctgctgc agggagctca aaatggagga     840
cgcggcgctc gggagagcgg gcgggtgagt cacccacaca aaggaaaagg gcctttccgt     900
cctcagccgt cgcttcatgt gactccactg agtaccgggc gccgtccagg cacctcgatt     960
agttctcgag cttttggagt acgtcgtctt taggttgggg ggagggggttt tatgcgatgg    1020
agtttcccca cactgagtgg gtggagactg aagttaggcc agcttggcac ttgatgtaat    1080
tctccttgga atttgccctt tttgagtttg gatcttggtt cattctcaag cctcagacag    1140
tggttcaaag ttttttttctt ccatttcagg tgtcgtga                            1178
```

<210> SEQ ID NO 8
<211> LENGTH: 1459
<212> TYPE: DNA
<213> ORGANISM: Artificial Sequence
<220> FEATURE:
<223> OTHER INFORMATION: Chemically Synthesized

<400> SEQUENCE: 8

| | | | | | |
|---|---|---|---|---|---|
| atggccttac | cagtgaccgc | cttgctcctg | ccgctggcct | tgctgctcca | cgccgccagg | 60 |
| ccggacatcc | agatgacaca | gactacatcc | tccctgtctg | cctctctggg | agacagagtc | 120 |
| accatcagtt | gcagggcaag | tcaggacatt | agtaaatatt | taaattggta | tcagcagaaa | 180 |
| ccagatggaa | ctgttaaact | cctgatctac | catacatcaa | gattacactc | aggagtccca | 240 |
| tcaaggttca | gtggcagtgg | gtctggaaca | gattattctc | tcaccattag | caacctggag | 300 |
| caagaagata | ttgccactta | cttttgccaa | cagggtaata | cgcttccgta | cacgttcgga | 360 |
| gggggaccca | agctggagat | cacaggtggc | ggtggctcgg | gcggtggtgg | gtcgggtggc | 420 |
| ggcggatctg | aggtgaaact | gcaggagtca | ggacctggcc | tggtggcgcc | ctcacagagc | 480 |
| ctgtccgtca | catgcactgt | ctcagggtc | tcattacccg | actatggtgt | aagctggatt | 540 |
| cgccagcctc | cacgaaaggg | tctggagtgg | ctgggagtaa | tatgggggtag | tgaaaccaca | 600 |
| tactataatt | cagctctcaa | atccagactg | accatcatca | aggacaactc | caagagccaa | 660 |
| gttttcttaa | aaatgaacag | tctgcaaact | gatgacacag | ccatttacta | ctgtgccaaa | 720 |
| cattattact | acggtggtag | ctatgctatg | gactactggg | gccaaggaac | ctcagtcacc | 780 |
| gtctcctcaa | ccacgacgcc | agcgccgcga | ccaccaacac | cggcgcccac | catcgcgtcg | 840 |
| cagccctgt | ccctgcgccc | agaggcgtgc | cggccagcgg | cggggggcgc | agtgcacacg | 900 |
| aggggggctgg | acttcgcctg | tgatatctac | atctgggcgc | ccttggccgg | acttgtgggg | 960 |
| gtccttctcc | tgtcactggt | tatcacccct | tactgcaaac | ggggcagaaa | gaaactcctg | 1020 |
| tatatattca | acaaccatt | tatgagacca | gtacaaacta | ctcaagagga | agatggctgt | 1080 |
| agctgccgat | ttccagaaga | agaagaagga | ggatgtgaac | tgagagtgaa | gttcagcagg | 1140 |
| agcgcagacg | cccccgcgta | caagcagggc | cagaaccagc | tctataacga | gctcaatcta | 1200 |
| ggacgaagag | aggagtacga | tgttttggac | aagagacgtg | gccgggaccc | tgagatgggg | 1260 |
| ggaaagccga | aaggaagaa | ccctcaggaa | ggcctgtaca | atgaactgca | gaaagataag | 1320 |
| atggcggagg | cctacagtga | gattgggatg | aaaggcgagc | gccggagggg | caaggggcac | 1380 |
| gatggccttt | accagggtct | cagtacagcc | accaaggaca | cctacgacgc | ccttcacatg | 1440 |
| caggccctgc | ccctcgct | | | | | 1459 |

<210> SEQ ID NO 9
<211> LENGTH: 591
<212> TYPE: DNA
<213> ORGANISM: Artificial Sequence
<220> FEATURE:
<223> OTHER INFORMATION: Chemically Synthesized

<400> SEQUENCE: 9

| | | | | | |
|---|---|---|---|---|---|
| atcaacctct | ggattacaaa | atttgtgaaa | gattgactgg | tattcttaac | tatgttgctc | 60 |
| cttttacgct | atgtggatac | gctgctttaa | tgcctttgta | tcatgctatt | gcttcccgta | 120 |
| tggctttcat | tttctcctcc | ttgtataaat | cctggttgct | gtctctttat | gaggagttgt | 180 |
| ggcccgttgt | caggcaacgt | ggcgtggtgt | gcactgtgtt | tgctgacgca | accccactg | 240 |
| gttggggcat | tgccaccacc | tgtcagctcc | tttccgggac | tttcgctttc | cccctcccta | 300 |
| ttgccacggc | ggaactcatc | gccgcctgcc | ttgcccgctg | ctggacaggg | gctcggctgt | 360 |
| tgggcactga | caattccgtg | gtgttgtcgg | ggaagctgac | gtccttccca | tggctgctcg | 420 |

```
cctgtgttgc cacctggatt ctgcgcggga cgtccttctg ctacgtccct tcggccctca    480
atccagcgga ccttccttcc cgcggcctgc tgccggctct gcggcctctt ccgcgtcttc    540
gccttcgccc tcagacgagt cggatctccc tttgggccgc tccccgcct g              591
```

```
<210> SEQ ID NO 10
<211> LENGTH: 98
<212> TYPE: DNA
<213> ORGANISM: Artificial Sequence
<220> FEATURE:
<223> OTHER INFORMATION: Chemically Synthezied

<400> SEQUENCE: 10
gggtctctct ggttagacca gatctgagcc tgggagctct ctggctaact agggaaccca    60
ctgcttaagc ctcaataaag cttgccttga gtgcttca                            98
```

```
<210> SEQ ID NO 11
<211> LENGTH: 84
<212> TYPE: DNA
<213> ORGANISM: Artificial Sequence
<220> FEATURE:
<223> OTHER INFORMATION: Chemically Synthesized

<400> SEQUENCE: 11
agtagtgtgt gcccgtctgt tgtgtgactc tggtaactag agatccctca gacccttta     60 gtcagtgtgg aaaatctcta gcag                                           84
```

```
<210> SEQ ID NO 12
<211> LENGTH: 486
<212> TYPE: PRT
<213> ORGANISM: Artificial Sequence
<220> FEATURE:
<223> OTHER INFORMATION: Chemically Synthesized

<400> SEQUENCE: 12

Met Ala Leu Pro Val Thr Ala Leu Leu Pro Leu Ala Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190
```

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
        210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 13
<211> LENGTH: 63
<212> TYPE: DNA
<213> ORGANISM: Artificial Sequence
<220> FEATURE:
<223> OTHER INFORMATION: Chemically Synthesized

<400> SEQUENCE: 13
atggccttac cagtgaccgc cttgctcctg ccgctggcct tgctgctcca cgccgccagg    60
ccg                                                                 63

<210> SEQ ID NO 14
<211> LENGTH: 726
<212> TYPE: DNA
<213> ORGANISM: Artificial Sequence
<220> FEATURE:
<223> OTHER INFORMATION: Chemically Synthesized

<400> SEQUENCE: 14

```
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggaccaagc tggagatcac aggtggcggt ggctcgggcg gtggtgggtc gggtggcggc   360
ggatctgagg tgaaactgca ggagtcagga cctggcctgg tggcgccctc acagagcctg   420
tccgtcacat gcactgtctc aggggtctca ttacccgact atggtgtaag ctggattcgc   480
cagcctccac gaaagggtct ggagtggctg gagtaatat ggggtagtga aaccacatac   540
tataattcag ctctcaaatc cagactgacc atcatcaagg acaactccaa gagccaagtt   600
ttcttaaaaa tgaacagtct gcaaactgat gacacagcca tttactactg tgccaaacat   660
tattactacg gtggtagcta tgctatggac tactggggcc aaggaacctc agtcaccgtc   720
tcctca                                                              726
```

<210> SEQ ID NO 15
<211> LENGTH: 135
<212> TYPE: DNA
<213> ORGANISM: Artificial Sequence
<220> FEATURE:
<223> OTHER INFORMATION: Chemically Synthesized

<400> SEQUENCE: 15

```
accacgacgc cagcgccgcg accaccaaca ccggcgccca ccatcgcgtc gcagcccctg    60
tccctgcgcc cagaggcgtg ccggccagcg gcgggggggcg cagtgcacac gagggggctg   120
gacttcgcct gtgat                                                    135
```

<210> SEQ ID NO 16
<211> LENGTH: 72
<212> TYPE: DNA
<213> ORGANISM: Artificial Sequence
<220> FEATURE:
<223> OTHER INFORMATION: Chemically Synthesized

<400> SEQUENCE: 16

```
atctacatct gggcgcccctt ggccgggact tgtggggtcc ttctcctgtc actggttatc    60
accctttact gc                                                        72
```

<210> SEQ ID NO 17
<211> LENGTH: 126
<212> TYPE: DNA
<213> ORGANISM: Artificial Sequence
<220> FEATURE:
<223> OTHER INFORMATION: Chemically Synthesized

<400> SEQUENCE: 17

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 18
<211> LENGTH: 336
<212> TYPE: DNA

```
<213> ORGANISM: Artificial Sequence
<220> FEATURE:
<223> OTHER INFORMATION: Chemically Synthesized

<400> SEQUENCE: 18
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggg aaagccgaga aggaagaacc ctcaggaagg cctgtacaat    180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

```
<210> SEQ ID NO 19
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 19

Met Ala Leu Pro Val Thr Ala Leu Leu Leu Pro Leu Ala Leu Leu Leu
1               5                   10                  15

His Ala Ala Arg Pro
            20
```

```
<210> SEQ ID NO 20
<211> LENGTH: 242
<212> TYPE: PRT
<213> ORGANISM: Artificial Sequence
<220> FEATURE:
<223> OTHER INFORMATION: Chemically Synthesized

<400> SEQUENCE: 20

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190
```

```
Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 21
<211> LENGTH: 47
<212> TYPE: PRT
<213> ORGANISM: Artificial Sequence
<220> FEATURE:
<223> OTHER INFORMATION: Chemically Synthesized

<400> SEQUENCE: 21

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr
            35                  40                  45

<210> SEQ ID NO 22
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 22

Ile Trp Ala Pro Leu Ala Gly Thr Cys Gly Val Leu Leu Leu Ser Leu
1               5                   10                  15

Val Ile Thr Leu Tyr Cys
                20

<210> SEQ ID NO 23
<211> LENGTH: 42
<212> TYPE: PRT
<213> ORGANISM: Artificial Sequence
<220> FEATURE:
<223> OTHER INFORMATION: Chemically Synthesized

<400> SEQUENCE: 23

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 24
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 24

Arg Val Lys Phe Ser Arg Ser Ala Asp Ala Pro Ala Tyr Lys Gln Gly
1               5                   10                  15
```

```
Gln Asn Gln Leu Tyr Asn Glu Leu Asn Leu Gly Arg Arg Glu Glu Tyr
                20                  25                  30

Asp Val Leu Asp Lys Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
 65              70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 25
gaaagctgac tgcccctatt tg                                          22

<210> SEQ ID NO 26
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 26
gagaggaagt gctgggaaca at                                          22

<210> SEQ ID NO 27
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 27
ctccccagtc tcttt                                                  15
```